US007745691B2

(12) United States Patent
Farese, Jr. et al.

(10) Patent No.: US 7,745,691 B2
(45) Date of Patent: Jun. 29, 2010

(54) GENETICALLY MODIFIED MOUSE LACKING DIACYLGLYCEROL ACYLTRANSFERASE-1 (DGAT-1) ACTIVITY

(75) Inventors: Robert V. Farese, Jr., Kentfield, CA (US); Hubert C. Chen, Newbury Parl, CA (US); Steven J. Smith, San Francisco, CA (US); Sylvaine Cases, Belmont, CA (US); Sandra K. Erickson, San Francisco, CA (US)

(73) Assignees: The Regents of the University of California, Oakland, CA (US); The United States of America as represented by the Department of Veterans Affairs, Washington, DC (US); The J. David Gladstone Institutes, San Francisco, CA (US)

( * ) Notice: Subject to any disclaimer, the term of this patent is extended or adjusted under 35 U.S.C. 154(b) by 184 days.

(21) Appl. No.: 11/609,810

(22) Filed: Dec. 12, 2006

(65) Prior Publication Data

US 2007/0123463 A1    May 31, 2007

Related U.S. Application Data

(60) Division of application No. 10/289,172, filed on Nov. 5, 2002, now abandoned, which is a continuation-in-part of application No. 10/040,315, filed on Oct. 29, 2001, now abandoned, which is a continuation-in-part of application No. 09/339,472, filed on Jun. 23, 1999, now abandoned, said application No. 10/040,315 is a continuation-in-part of application No. PCT/US98/17883, filed on Aug. 28, 1998, which is a continuation-in-part of application No. 09/103,754, filed on Jun. 24, 1998, now Pat. No. 6,344,548.

(60) Provisional application No. 60/107,771, filed on Nov. 9, 1998.

(51) Int. Cl.
*A01K 67/027* (2006.01)
*A01K 67/00* (2006.01)
*G01N 33/00* (2006.01)

(52) U.S. Cl. .................... 800/18; 800/8; 800/3
(58) Field of Classification Search .............. 800/8, 800/18, 3
See application file for complete search history.

(56) References Cited

U.S. PATENT DOCUMENTS

| 4,770,781 | A | 9/1988 | Schmidt et al. |
| 4,801,686 | A | 1/1989 | Kronheim |
| 4,894,333 | A | 1/1990 | Cerretti et al. |
| 5,017,692 | A | 5/1991 | Zurawski et al. |
| 5,266,311 | A | 11/1993 | Cerretti et al. |
| 5,702,698 | A | 12/1997 | Nakai et al. |
| 6,100,077 | A | 8/2000 | Sturley et al. |
| 6,552,250 | B1 | 4/2003 | Nykiforuk et al. |
| 6,607,893 | B2 | 8/2003 | Ramharack et al. |
| 7,015,373 | B1 | 3/2006 | Zou et al. |
| 2005/0193446 | A1 | 9/2005 | Zou et al. |
| 2006/0090222 | A1 | 4/2006 | Zou et al. |
| 2007/0166748 | A1* | 7/2007 | Gimeno et al. .......... 435/6 |

FOREIGN PATENT DOCUMENTS

| EP | 0 188 920 A2 | 7/1986 |
| EP | 0 200 986 A1 | 11/1986 |
| EP | 0 324 447 A2 | 1/1988 |
| EP | 0 327 360 A2 | 8/1989 |

OTHER PUBLICATIONS

Denning and Priddle. Reproduction 126:1-11. 2003.*
Scanlon. Cur Pharm Biotech 5:415-420, 2004.*
"Rodent". (2009). In Encyclopædia Britannica. Retrieved Apr. 22, 2009, from Encyclopædia Britannica Online: http://www.search.eb.com/eb/article-9105980.*
Reichhardt, Donald. Scientific Method Uses Experiments and Controls. May 26, 2009 from http:/scientificinquiry.suite101.com/article.cfm/scientific_method_uses_experiments_and_controls. printout Oct. 27, 2009, pp. 1-4.*
Masuzaki et al. Diabetes 48:1615-1622, 1999.*
Andersson M. et al., "Purification of Diacylglycerol: Acyltransferase from rat liver to near homogeneity", Journal of Lipid Research, Bethesda MD, US. vol. 35, 1994, pp. 535-545.
Buhman Kimberly K. et al., DGAT1 is not essential for intestinal traicyglycerol absorption or chlomicron synthesis "The Journal of Biological Chemistry", U.S. Jul. 12, 2002, vol. 277, No. 28, Jul. 12, 2002, pp. 25474-25479.
Cases S. et al., "Identification of Gene Encoding an acyl CoA: Diacyglycerol Acyltransferase, a Key Enzyme in Triacyglycerol Synthesis" Proceedings of the National Academy of Sciences of USA, National Academy of Science, Washington, US, vol. 985, No. 22, Oct. 27, 1998.
Chen HC et al., Increased insulin and leptin sensitivity in mice lacking acyl CoA: diacylyglycerol acyltransferase I "The Journal of Clinical Investigation" vol. 109, No. 8, Apr. 2002, pp. 1049-1055.

(Continued)

*Primary Examiner*—Thaian N Ton
*Assistant Examiner*—Marcia S Noble
(74) *Attorney, Agent, or Firm*—Paula A. Borden; Bozicevic, Field & Francis LLP

(57) ABSTRACT

Methods and compositions for modulating carbohydrate metabolism in a host are provided. In the subject methods, diacylglycerol acyltransferase (DGAT) activity (specifically DGAT1 activity) is modulated, e.g., reduced or enhanced, to achieve a desired insulin and/or leptin sensitivity, thereby modulating carbohydrate metabolism, e.g., increasing or decreasing blood glucose levels, glucose uptake into cells and assimilation into glycogen. Also provided are pharmaceutical compositions for practicing the subject methods. The subject methods and compositions find use in a variety of applications, including the treatment of hosts suffering conditions associated with abnormal carbohydrate metabolism, such as obesity or diabetes.

5 Claims, 6 Drawing Sheets

OTHER PUBLICATIONS

Database Genbank [Online] Sep. 19, 1997 Newman et al., 24635 CE4-13 *Arabidopsis thaliana* cDNA clone E6B2T7,RMA seqiemce. Database Accession No. AA042298.

Database Genbank [Online] Oct. 15, 1998, Oelkers et al., "*Homo sapiens* ACAT related gene product 1 mRNA, complete CDs". Database Accession No. AF059202.

Farese, FV Jr., "Acyl CoA: cholesterol acyltransferase genes and knockout mice" Current Opinion in Lipidology, vol. 9, No. 2, Apr. 1998, pp. 119-123.

Frentzen M. "Acyltransferases from basic science to modified seed oils", Fett-Lipid, Wiley—VCH Verlag, Weinham, DE, vol. 100, No. 4/5, May 1998, pp. 161-166.

Katavic V et al., "Alteration of Seed Fatty Acid Composition by an Ethyl Mathanesulfonate-Induced Mutation in *Arabidopsis thaliana* Affecting Diacylglycerol Acyltransferase Activity" Plant Physiology, American Society of Plant Physiologists, Rockville, MD, US, vol. 108, 1995, pp. 399-409.

Kwanyuen P. et al., "Subunit and Amino Acid Composition of Diacylglycerol Acyltransferase from Germinating Soybean Cotyledons" Biochimica et Biophysica ACTA, Amsterdam, NL, vol. 1039, No. 1, May 31, 1990.

Kwanyuen P; Wilson RF: "N-Terminal Sequence of the 40.8 kDa Subunit of Diacylglycerol Acyltransferase from Soybean" Plant Physiology, vol. 96, No. 1 Suppl., May 1991, p. 125.

Oelkers et al., "Characterization of two human genes encoding acyl coenzyme A:cholesterol acyltransferase-related enzymes." Journal of Biological Chemistry, vol. 273, No. 41, Oct. 1998, pp. 26765-26771, XP002122746.

Schoonderwoerd et al., "Properties of phosphatidate phosphohydrolase and dicylglycerol acyltransferase activities in the isolated rat heart" Biochem J 268:487-492, 1990.

Smith S J et al., "Obesity resistance and multiple mechanisms of triglyceride synthesis in mice lacking Dgat", Nature America, New York, US, vol. 25, No. 1, May 2000, pp. 87-90.

Tabata et al., "Xanthohumols, diacylglycerol acyltransferase inhibitors, from *Humulus lupulus*" Phytochemistry, Pergamon Press, GB, vol. 46, No. 4, Oct. 1997, pp. 683-687, XP004293462 ISSN: 0031-9422.

Thyagaran et al., "Genetically Altered Mouse Models: The Good, the Bad, and the Ugly", Crit Rev Oral Biol Med 14(3): 154-174, 2003.

Wilson, R. F. et al., "Recent Developments in the molecular biochemistry and genetics of diacyglycerol acyltransferase from soybean" Seed Oils for the Future, AOCS press, Champaign, IL, US, 1992, pp. 116-135.

Zou et al., "The *Arabidopsis thaliana* TAG1 mutant has a mutation in a diacylglycerol acyltransferase gene", Plant Journal, Blackwell Scientific Publications, Oxford GB, vol. 19, No. 6, Sep. 1999, pp. 645-653.

Aiko, et al. Effects of nitric oxide synthase inhibition or sulfasalazine on the spontaneous colitis observed in HLA-B27 transgenic rats. J Pharmacol Exp Ther. Feb. 1998;284(2):722-7.

Bohlender, et al. Mouse and rat plasma renin concentration and gene expression in (mRen2) 27 transgenic rats. Am J Physiol Heart Circ Physiol, 1998, 274:1450-1456.

Fan, et al. Overexpression of hepatic lipase in transgenic rabbits leads to a marked reduction of plasma high density lipoproteins and intermediate density lipoproteins. Proc. Natl. Acad. Sci. 1994, vol. 91, pp. 8724-8728.

Huang, et al. Apolipoprotein E2 transgenic rabbits. Modulation of the type III hyperlipoproteinemic phenotype by estrogen and occurence of spontaneous atherosclerosis. The Journal of Biological Chemistry, 1997, vol. 272, No. 36, 22685-22694.

Korhonen, et al. Expression of bovine beta-lactoglobulin/human erythropoietin fusion protein in the milk of transgenic mice and rabbits. Eur. J. Biochem. 1997, vol. 245, pp. 482-489.

Krebs, et al. The DNA damaging drug cyproterone acetate causes gene mutations and induces glutathione-S-transferase P in the liver of female Big Blue transgenic F344 rats. Carcinogenesis, 1998, vol. 19, No. 2, pp. 241-245.

Venkatesh, et al. Transgenic rats reveal functional conservation of regulatory controls between the Fugu isotocin and rat oxytocin genes. Proc. Natl. Acad. Sci. 1997, vol. 94, pp. 12462-12466.

Wolf, et al. Human insulin-like growth factor I (IGF-I) produced in the mammary glands of transgenic rabbits: yield, receptor binding, mitogenic activity, and effects on IGF-binding proteins. Endocrinology, 1997, vol. 138, No. 1, pp. 307.

* cited by examiner

GENETICALLY MODIFIED MOUSE LACKING DIACYLGLYCEROL ACYLTRANSFERASE-1 (DGAT-1) ACTIVITY

CROSS REFERENCE TO RELATED APPLICATIONS

This application is a divisional patent application of application Ser. No. 10/289,172, filed Nov. 5, 2002, which is a continuation-in-part of application Ser. No. 10/040,315 filed Oct. 29, 2001; which application is: (a) a continuation-in-part of application Ser. No. 09/339,472 filed on Jun. 23, 1999, which application claims priority to the filing date of U.S. Provisional Patent Application Ser. No. 60/107,771 filed Nov. 9, 1998; and (b) a continuation-in-part of PCT application serial no. PCT/US98/17883, filed Aug. 28, 1998, which application is a continuation in part of application Ser. No. 09/103,754, now U.S. Pat. No. 6,344,548, filed Jun. 24, 1998; the disclosures of which applications are herein incorporated by reference.

ACKNOWLEDGEMENT OF GOVERNMENT SUPPORT

This invention was made with Government support under Grant Nos. DK-56084 and DK-26356 awarded by the National Institutes of Health. The Government has certain rights in this invention.

INTRODUCTION

1. Field of the Invention

The invention relates generally to methods of treating conditions associated with abnormal carbohydrate metabolism, such as obesity and diabetes. Specifically, the invention relates to methods of modulating insulin and/or leptin sensitivity in a host.

2. Background of the Invention

A human that weighs greater than about 20% more than an ideal weight is considered obese, and, as such, is highly susceptible the health problems including coronary artery disease, stroke, and certain cancers. Within the United States about 24% of men and 27% of women are considered mildly to severely obese. While partially effective treatments for obesity based on diet, lifestyle and surgery have been developed, no effective drug-based treatment for human obesity is currently available.

Obesity in humans is commonly associated with altered sensitivity to insulin and/or leptin, which are circulatory hormones that modulate energy homeostasis. In general, leptin, the product of the obese gene, acts in the central nervous system to regulate food intake, energy metabolism and body weight. Insulin, however, mainly functions to regulate the concentration of blood sugar and blood lipids through the promotion of glucose and lipid intake into cells for utilization and storage.

Leptin is secreted by adipocytes and acts in the hypothalamus through the leptin receptor (OB-R). Despite the fact that rodents with mutations in either the leptin or OB-R genes are profoundly obese and diabetic (Coleman et al., Diabetologia 14, 141-148, 1978), most obese humans do not have mutations in these genes (Considine et al., Diabetes 19, 992-994, 1996). The observation that the vast majority of obese humans have chronically elevated serum leptin levels (Maffei, et al. (1995) Nature Med. 1, 1155-1161) has led to proposal that a primary cause of obesity is "leptin resistance" in that obese individuals, while capable of generating a large amount of circulatory leptin, are unable to properly respond to it. The mechanisms by which a subject becomes leptin resistant are not understood.

Insulin is secreted by the pancreas in response to an increase in blood glucose, for example after glucose has entered the bloodstream from the intestine after a carbohydrate-rich meal. Insulin stimulates glucose uptake by muscle tissue, where the glucose is converted to glucose 6-phosphate, which is then used to make glycogen. As a consequence of the accelerated uptake of glucose from the blood, blood glucose concentration falls to the normal level, slowing insulin release from the pancreas. There is a closely adjusted feedback relationship between the rate of insulin secretion and blood glucose concentration, which holds blood glucose concentration nearly constant despite large fluctuations in dietary intake.

In addition to stimulating glucose uptake, insulin also stimulates the storage of excess carbohydrates as fat. It activates both the oxidation of glucose 6-phosphate to pyruvate via glycolysis and the oxidation of pyruvate to acetyl-CoA. If not oxidized further for energy production, this acetyl-CoA is used for fatty acid synthesis in the liver, and these fatty acids are exported as triglycerols of plasma lipoproteins (VLDLs) to adipose tissue. Insulin stimulates triacylglycerol (TAG) synthesis in adipocytes, using fatty acids released from the VLDL TAGs. The fatty acids are ultimately derived from the glucose taken from the blood by the liver.

As such, insulin regulates the conversion of excess blood glucose into two storage forms: glycogen (in liver and muscle) and TAG (in adipose tissue).

Many obese individuals have elevated levels of insulin as well as elevated levels of blood sugar and/or blood lipid, and, as such, are thought to be "insulin resistant" in that these individuals, while capable of generating a large amount of circulatory insulin, are unable to respond properly to the insulin. The causative mechanisms of insulin resistance have not yet been fully elucidated, and examples of diseases caused by insulin resistance include diabetes, obesity, diabetic microangiopathies (diabetic nephropathy, diabetic neuropathy, and diabetic retinopathy), impaired glucose tolerance, hyperinsulinemia, hyperlipemia, arteriosclerosis, hypertension, obesity, ischemic heart diseases, ischemic brain disorders, and peripheral arterial embolism (Tamio Teramoto, et al., (1995) Biomedicine & Therapeutics 29, 8-96).

It is clear that insulin and leptin signaling play key roles in maintaining energy homeostasis in normal individuals and that most obese individuals have altered sensitivity to these hormones, leading to excessive food consumption, low energy usage and weight gain. A need therefore exists for therapies based on modulating the sensitivity of a subject to leptin and/or insulin. This invention meets these, and other, needs.

SUMMARY OF THE INVENTION

Methods and compositions for modulating carbohydrate metabolism in a host are provided. In the subject methods, diacylglycerol acyltransferase (DGAT) activity (specifically DGAT1 activity) is modulated, e.g., reduced or enhanced, to achieve a desired insulin and/or leptin sensitivity, thereby modulating carbohydrate metabolism, e.g., increasing or decreasing blood glucose levels, glucose uptake into cells and assimilation into glycogen. Also provided are pharmaceutical compositions for practicing the subject methods, etc. The subject methods and compositions find use in a variety of applications, including the treatment of hosts suffering conditions associated with abnormal carbohydrate metabolism, such as obesity or diabetes.

BRIEF DESCRIPTION OF THE FIGURES

(FIG. 2a) Glucose tolerance test. (FIG. 2b) Insulin tolerance test. (FIG. 2c) Hyperinsulinemic-euglycemic clamp study. n=5-6 chow-fed male mice per genotype in each experiment. *P<0.05 versus Dgat1$^{+/+}$ mice.

(FIG. 3a and FIG. 3b) Body weight. (FIG. 3c and FIG. 3d) Food intake. Sex-, age-, and weight-matched mice were used. n=6-8 chow-fed mice per genotype. Error bars represent SEM. **P<0.01 versus Dgat1$^{+/+}$ mice receiving the same dose of leptin.

DEFINITIONS

Figure 1:
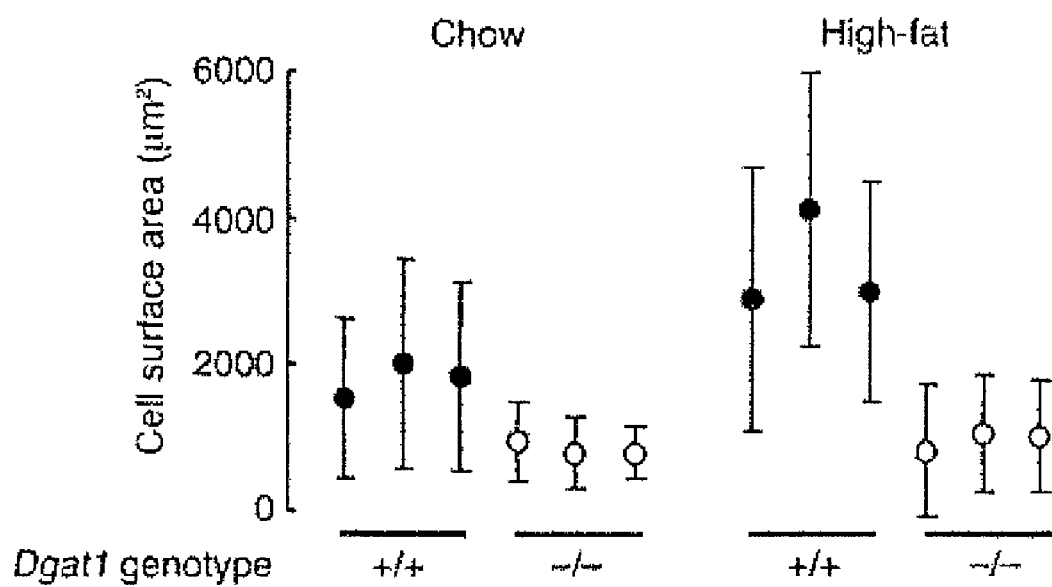
FIG. 1 is a graph showing decreased adipocyte size in Dgat1$^{-/-}$ mice. Each circle represents the mean adipocyte surface area of one female mouse. More than 100 adipocytes were measured per mouse. For high-fat experiments, mice were fed a high-fat diet for 10 weeks.

Unless defined otherwise, all technical and scientific terms used herein have the same meaning as commonly understood by one of ordinary skill in the art to which this invention belongs. Still, certain elements are defined below for the sake of clarity and ease of reference.

As used herein, the terms "condition associated with abnormal carbohydrate metabolism" and "disorder associated with abnormal carbohydrate metabolism" are used interchangeably to refer to any disorder that is caused by an alteration in carbohydrate metabolism. Such disorders include, but are not limited to: blood glucose-related disorders, including diabetic microangiopathies (diabetic nephropathy, diabetic neuropathy, and diabetic retinopathy), impaired glucose tolerance, hyperinsulinemia, hyperlipemia, arteriosclerosis, hypertension, obesity, ischemic heart diseases, ischemic brain disorders, peripheral arterial embolism, diabetes mellitus, diabetes insipidus, gestational diabetes, diabetes innocens, diabetes insipidus, nephrogenic diabetes insipidus, diabetes intermittens, diabetes mellitus, insulin-dependent diabetes mellitus, lipoatrophic diabetes mellitus, non-insulin-dependent diabetes mellitus, type 1 diabetes and type 2 diabetes; and disorders relating to obesity, including diabetes, type 2 diabetes, hypertension, stroke, myocardial infarction or congestive heart failure, prostate and colon cancer, gallstones, cholecystitis, gout, gouty arthritis, osteoarthritis, degenerative arthritis of the knees, hips, or the lower back, apnea, and pickwickian syndrome. In general, a condition associated with abnormal carbohydrate metabolism is caused, or is otherwise associated with, an abnormal, e.g., decreased sensitivity to insulin and/or leptin. In certain embodiments, a condition associated with leptin and/or insulin over-activity, e.g., anorexia, is also encompassed by this term.

The term "phenomenon associated with carbohydrate metabolism" as used herein refers to a structural, molecular, or functional characteristic associated with carbohydrate metabolism, particularly such a characteristic that is readily assessable in a mammalian host. Such characteristics include, but are not limited to: increased or decreased lipid levels, adipocyte size, blood glucose levels, glucose disposal, glucose tolerance, glucose uptake, glycogen synthesis rate, insulin tolerance, weight loss, food intake, triacylglycerol levels, energy expenditure, weight levels, weight gain, activity levels or an alteration in lipid content and the like.

The term "phenomenon associated with sensitivity to insulin and/or leptin" as used herein refers to a structural, molecular, or functional characteristic associated with carbohydrate metabolism, particularly such a characteristic that is readily assessable in a mammalian host. Such characteristics include, but are not limited to: increased or decreased lipid levels, adipocyte size, blood glucose levels, glucose disposal, glucose tolerance, glucose uptake, glycogen synthesis rate, insulin tolerance, weight loss, food intake, triacylglycerol levels, energy expenditure, weight levels, weight gain, activity levels or an alteration in lipid content and the like.

As used herein, the terms "determining," "measuring," and "assessing," and "assaying" are used interchangeably and include both quantitative and qualitative determinations.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "polynucleotide" and "nucleic acid molecule" are used interchangeably herein to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes single-, double-stranded and triple helical molecules. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially pure" refers to a compound that is removed from its natural environment and is at least 60% free, preferably 75% free, and most preferably 90% free from other components with which it is naturally associated.

By "transgenic animal" is meant a non-human animal, usually a mammal, having a non-endogenous (i.e., heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal according to methods well known in the art. A "transgene" is meant to refer to such heterologous nucleic acid, e.g., heterologous nucleic acid in the form of an expression construct (e.g., for the production of a "knock-in" transgenic animal) or a heterologous nucleic acid that upon insertion within or adjacent a target gene results in a decrease in target gene expression (e.g., for production of a "knock-out" transgenic animal).

A "knock-out" of a gene means an alteration in the sequence of the gene that results in a decrease of function of the target gene, preferably such that target gene expression is undetectable or insignificant. Transgenic knock-out animals can comprise a heterozygous knock-out of a target gene, or a homozygous knock-out of a target gene. "Knock-outs" as used herein also include conditional knock-outs, where alteration of the target gene can occur upon, for example, exposure of the animal to a substance that promotes target gene alteration, introduction of an enzyme that promotes recombination at the target gene site (e.g., Cre in the Cre-lox system), or other method for directing the target gene alteration postnatally.

A "knock-in" of a target gene means an alteration in a host cell genome that results in altered expression (e.g., increased (including ectopic) or decreased expression) of a target gene, e.g., by introduction of an additional copy of the target gene, or by operatively inserting a regulatory sequence that provides for enhanced expression of an endogenous copy of the target gene. "Knock-in" transgenics can comprise a heterozygous knock-in of the target gene or a homozygous knock-in of a target gene. "Knock-ins" also encompass conditional knock-ins.

By "operably linked" is meant that a DNA sequence and a regulatory sequencers) are connected in such a way as to permit gene expression when the appropriate molecules (e.g., transcriptional activator proteins) are bound to the regulatory sequencers).

By "operatively inserted" is meant that a nucleotide sequence of interest is positioned adjacent a nucleotide sequence that directs transcription and translation of the introduced nucleotide sequence of interest.

The term "therapeutic agent" as used herein refers to any molecule, e.g., protein or small molecule, pharmaceutical compound, antibody, antisense molecule, ribozyme, and the like, useful in the treatment of a disease or condition, e.g., a condition associated with abnormal carbohydrate metabolism. For example, therapeutic agents of the invention include molecules that inhibit, ameliorate, or relieve symptoms of a condition associated with abnormal carbohydrate metabolism.

The term "unit dosage form" as used herein refers to physically discrete units suitable as unitary dosages for subjects (e.g., animals, usually humans), each unit containing a predetermined quantity of agent(s) in an amount sufficient to produce the desired effect in association with a pharmaceutically acceptable diluent, carrier or vehicle. The specifications for the novel unit dosage forms of the present invention will depend on a variety of factors including, but not necessarily limited to, the particular agent employed and the effect to be achieved, and the pharmacodynamics associated with each compound in the host.

The terms "treatment treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease.

The terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

DETAILED DESCRIPTION OF THE INVENTION

Methods and compositions for modulating carbohydrate metabolism in a host are provided. In the subject methods, diacylglycerol acyltransferase (DGAT) activity (specifically DGAT1 activity) is modulated, e.g., reduced or enhanced, to achieve a desired insulin and/or leptin sensitivity, thereby modulating carbohydrate metabolism, e.g., increasing or decreasing blood glucose levels, glucose uptake into cells and assimilation into glycogen, etc. Also provided are pharmaceutical compositions for practicing the subject methods. The subject methods and compositions find use in a variety of applications, including the treatment of hosts suffering conditions associated with abnormal carbohydrate metabolism, such as obesity or diabetes.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

In further describing the invention, representative methods of modulating sensitivity of a host to insulin and/or leptin and compositions for performing the methods are described first. Following this, a detailed description of representative applications in which the subject methods find use is provided. Next, representative kits that find use in practicing the subject methods are further described.

Methods of Modulating Sensitivity to Insulin and/or Leptin

The invention provides methods of modulating sensitivity to insulin and/or leptin in a host. In general, the methods involve administering to a host an effective amount of one or more active agents that modulate DGAT1 activity in the host to modulate sensitivity to insulin and/or leptin in the host.

By DGAT1 activity is meant the activity of a DGAT1 protein, where representative DGAT1 proteins are disclosed in Cases et al., Proc. Nat'l Acad. Sci. USA (1998) 95:13018-13023 and Genbank Accession Nos.: AAC63997, AF059202; as well as U.S. Pat. Nos. 6,100,077 and 6,344,548 and the priority applications to the present application (listed above); the disclosures of which are herein incorporated by reference.

As DGAT1 activity is modulated in certain embodiments of the invention, DGAT1 activity is increased or decreased in these embodiments. In many embodiments, DGAT1 activity is increased or decreased by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, as compared to a baseline DGAT1 activity level, e.g., that observed in the host prior to administration of the active agent. In certain embodiments, DGAT1 activity may be decreased by at least about 100%, by at least about 300%, by at least about 5-fold, by at least about 10-fold, by at least about 50-fold, or by at least about 100-fold, or more, as compared to a baseline DGAT1 activity level, e.g., that observed in the host prior to administration of the active agent.

Upon administration of a DGAT1 modulatory agent to a host, insulin and/or leptin activity is usually increased or decreased by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to a control in the absence of an effective amount of the active agent. In certain embodiments, upon administration of a DGAT1 modulatory agent, especially a DGAT1 inhibitory agent, to a host, insulin and/or leptin activity may be increased by at least about 100%, by at least about 300%, by at least about 5-fold, by at least about 10-fold, by at least 50-fold, or by at least 100-fold as compared to a control in the absence of an effective amount of the active agent.

Sensitivity to insulin and/or leptin is usually measured in terms of an assessment of a phenomenon associated with carbohydrate metabolism of a host, e.g., levels of blood glucose or fatty acids, in response to a specific dose of insulin and/or leptin, especially after consumption of carbohydrates.

In some embodiments where the desired modulation of sensitivity to insulin and/or leptin is an increase in sensitivity to insulin and/or leptin, one or more agents that decreases DGAT1 activity is administered to the host. For example, in certain embodiments, one or more agents that decreases DGAT1 activity is administered to the host. In these embodiments, the agent is typically a DGAT1 inhibitor.

In some embodiments where the desired modulation of sensitivity to insulin and/or leptin is a decrease in sensitivity to insulin and/or leptin, one or more agents that increase DGAT1 activity is administered to the host. For example, in certain embodiments, one or more agents that increases DGAT1 activity is administered to the host.

For the modulation of DGAT1 activity in a host, an effective amount of an active agent(s) that modulates the activity, e.g., reduces the activity of DGAT1 in vivo, is administered to the host. The active agent may be one or a mixture of a variety of different compounds, including: polynucleotide compositions (e.g., coding sequences, antisense compositions, siRNA compositions, etc.), polypeptide, including antibody, compositions, naturally occurring or synthetic small molecule compounds, etc.

In certain embodiments, the active agents administered to the host are polynucleotide or nucleic acid compositions. The nucleic acids may be coding sequences, e.g., genes, gene fragments etc., which may be present in expression vectors, where such vectors generally have convenient restriction sites located near the promoter sequence to provide for the insertion of nucleic acid sequences. Transcription cassettes may be prepared that include a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

In yet other embodiments of the invention, the active agent is an agent that modulates, and generally decreases or down regulates, the expression of DGAT1 in the host. Antisense molecules can be used to down-regulate expression of a gene in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840-844).

A specific region or regions of the endogenous sense strand mRNA sequence is chosen to be complemented by the anti-sense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH$_2$-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225 and Beigelman et al. (1995), *Nucl. Acids Res.* 23:4434-42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43-56

Alternatively, gene expression can be modified by gene silencing using double-strand RNA (Sharp (1999) Genes and Development 13: 139-141). RNAi, otherwise known as double-stranded RNA interference (dsRNAi) or small interfering RNA (siRNA), has been extensively documented in the nematode *C. elegans* (Fire, A., et al, Nature, 391, 806-811, 1998) and an identical phenomenon occurs in plants, in which it is usually referred to as post-transcriptional gene silencing (PTGS) (Van Blokland, R., et al., Plant J., 6: 861-877, 1994; deCarvalho-Niebel, F., et al., Plant Cell, 7: 347-358, 1995; Jacobs, J. J. M. R. et al., Plant J., 12: 885-893, 1997; reviewed in Vaucheret, H., et al., Plant J., 16: 651-659, 1998). The phenomenon also occurs in fungi (Romano, N. and Masino, G., Mol. Microbiol., 6: 3343-3353, 1992, Cogoni, C., et al., EMBO J., 15: 3153-3163; Cogoni, C. and Masino, G., Nature, 399: 166-169, 1999), in which it is often referred to as "quelling". RNAi silencing can be induced many ways in plants, where a nucleic acid encoding an RNA that forms a "hairpin" structure is employed in most embodiments. Alternative strategies include expressing RNA from each end of the encoding nucleic acid, making two RNA molecules that will hybridize. Current strategies for RNAi induced silencing in plants are reviewed by Carthew et al (Curr Opin Cell Biol. 2001 13:244-8). RNAi is also described in WO 02/44321 and WO 01/68836; the priority documents of which are herein incorporated by reference.

Also of interest are polypeptide, e.g., proteinaceous, active agents. Specific polypeptide agents include proteins or active fragments thereof, e.g., DGAT1 proteins, etc.

A specific type of polypeptide active agent of interest is an antibody agent that modulates DGAT1 activity in the host. The antibodies may be monoclonal or polyclonal, and produced according to methods known in the art. Antibody fragments, such as Fv, F(ab')$_2$ and Fab may be prepared by cleavage of the intact protein, e.g. by protease or chemical cleavage.

Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc.

Naturally occurring or synthetic small molecule compounds of interest as active agents include numerous chemical classes, though typically they are organic molecules, preferably small organic compounds having a molecular weight of more than 50 and less than about 2,500 daltons. Candidate agents include functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Of particular interest are those agents identified by the screening assays of the subject invention, as described above.

In certain embodiments, in addition to the DGAT1 modulatory active agent, a leptin and/or insulin modulatory active agent, e.g., an agent that enhances or inhibits leptin and/or insulin activity, is administered. For example, in certain embodiments where a DGAT1 inhibitory agent is administered, a leptin activity enhancing agent (e.g. leptin or an activity mimetic thereof) may also be administered, such that both a DGAT1 inhibitory agent and a leptin activity enhancing agent are administered to the host. In certain other embodiments where a DGAT1 inhibitory agent is administered, an insulin activity enhancing agent (e.g. insulin or an activity mimetic thereof) may also be administered, such that both a DGAT1 inhibitory agent and an insulin activity enhancing agent are administered to the host. Such embodiments include those embodiments where one wishes to modulate sensitivity to insulin and/or leptin in way that modulates a phenomenon associated with carbohydrate metabolism, e.g., blood glucose levels.

In practicing the subject methods, an effective amount of the active agent is administered to a host, where the term "effective amount" means a dosage sufficient to produce a desired result, where the desired result is the desired modulation, e.g., enhancement, reduction, of DGAT1 activity and a desired modulation in sensitivity to insulin and or leptin.

In practicing the subject methods, the active agent or agents are typically administered to the host in a physiologically acceptable delivery vehicle, e.g., as a pharmaceutical preparation. A variety of representative formulations, dosages, routes of administration for candidate agents, nucleic acid delivery vehicles and nucleic acid formulations for nucleic acid delivery are described below.

Formulations, Dosages, and Routes of Administration

The invention provides formulations, including pharmaceutical formulations, that include an agent which modulates sensitivity to insulin and/or leptin in a host. In general, a formulation comprises an effective amount of an agent that modulates DGAT1 (and/or leptin) activity in a host. An "effective amount" refers to an amount that is sufficient to produce a desired result, e.g., reduction of weight to normal levels, reduction of blood glucose levels, stabilization of blood glucose levels etc. In many embodiments, the desired result is at least a reduction or increase in a phenotype as compared to a control such that the phenotype is more similar to normal.

In certain embodiments, the agent that modulates sensitivity to insulin and/or leptin is administered before, with, or after administration of insulin and/or leptin, or mimetics thereof. Mimetics of insulin and of leptin activity are well known the art (see, for example, U.S. Pat. Nos. 6,444,641, 6,335,316, 5,952,297, 5,700,662, 5,698,669, 6,420,340, 7 6,355,635 and 3 6,420,339; the disclosures of which are herein incorporated by reference).

Formulations

In the subject methods, the active agent(s) may be administered to the host using any convenient means capable of resulting in the desired reduction in of a carbohydrate metabolism-related phenotype.

Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Other modes of administration will also find use with the subject invention. For instance, an agent of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

An agent of the invention can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985; Remington: The Science and Practice of Pharmacy, A. R. Gennaro, (2000) Lippincott, Williams & Wilkins. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

Although the dosage used will vary depending on the clinical goals to be achieved, a suitable dosage range is one which provides up to about 1 µg to about 1,000 µg or about 10,000 µg of an agent that modulates insulin and/or leptin resistance in a host, and in embodiments, modulates carbohydrate metabolism or treats a host suffering from a condition associated with abnormal carbohydrate metabolism.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

Routes of Administration

Conventional and pharmaceutically acceptable routes of administration include intranasal, intramuscular, intratracheal, intratumoral, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as a obesity and psychological trauma associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A subject polynucleotide can be delivered as a naked polynucleotide, or associated with (complexed with) a delivery vehicle. "Associated with", or "complexed with", encompasses both covalent and non-covalent interaction of a polynucleotide with a given delivery vehicle.

Nucleic Acid Delivery Vehicles

In certain embodiment, an agent is a nucleic acid. Nucleic acids may be delivered using several different vehicles, including viral and non-viral delivery vehicles.

Viral Delivery Vehicles

A subject polynucleotide can be associated with viral delivery vehicles. As used herein, a "viral delivery vehicle" intends that the polynucleotide to be delivered is encapsidated in a viral particle.

Numerous viral genomes useful in in vivo transformation and gene therapy are known in the art, or can be readily constructed given the skill and knowledge in the art. Included are replication competent, replication deficient, and replication conditional viruses. Viral vectors include adenovirus, mumps virus, a retrovirus, adeno-associated virus, herpes simplex virus (HSV), cytomegalovirus (CMV), vaccinia virus, and poliovirus, and non-replicative mutants/variants of the foregoing. In some embodiments, a replication-deficient virus is capable of infecting slowly replicating and/or terminally differentiated cells, since the respiratory tract is primarily composed of these cell types. For example, adenovirus efficiently infects slowly replicating and/or terminally differentiated cells. In some embodiments, the viral genome itself, or a protein on the viral surface, is specific or substantially specific for cells of the targeted cell. A viral genome can be designed to be target cell-specific by inclusion of cell type-specific promoters and/or enhancers operably linked to a gene(s) essential for viral replication.

Where a replication-deficient virus is used as the viral genome, the production of virus particles containing either DNA or RNA corresponding to the polynucleotide of interest can be produced by introducing the viral construct into a recombinant cell line which provides the missing components essential for viral replication and/or production. Preferably, transformation of the recombinant cell line with the recombinant viral genome will not result in production of replication-competent viruses, e.g., by homologous recombination of the viral sequences of the recombinant cell line into the introduced viral genome. Methods for production of replication-deficient viral particles containing a nucleic acid of interest are well known in the art and are described in, for example, Rosenfeld et al., Science 252:431-434, 1991 and Rosenfeld et al., Cell 68:143-155, 1992 (adenovirus); U.S. Pat. No. 5,139,941 (adeno-associated virus); U.S. Pat. No. 4,861,719 (retrovirus); and U.S. Pat. No. 5,356,806 (vaccinia virus). Methods and materials for manipulation of the mumps virus genome, characterization of mumps virus genes responsible for viral fusion and viral replication, and the structure and sequence of the mumps viral genome are described in Tanabayashi et al., J. Virol. 67:2928-2931, 1993; Takeuchi et al., Archiv. Virol., 128:177-183, 1993; Tanabayashi et al., Virol. 187:801-804, 1992; Kawano et al., Virol, 179:857-861, 1990; Elango et al., J. Gen. Virol. 69:2893-28900, 1988.

Non-Viral Delivery Vehicles

A subject polynucleotide can be administered using a non-viral delivery vehicle. "Non-viral delivery vehicle" (also referred to herein as "non-viral vector") as used herein is meant to include chemical formulations containing naked or condensed polynucleotides (e.g., a formulation of polynucleotides and cationic compounds (e.g., dextran sulfate)), and naked or condensed polynucleotides mixed with an adjuvant such as a viral particle (i.e., the polynucleotide of interest is not contained within the viral particle, but the transforming formulation is composed of both naked polynucleotides and viral particles (e.g., adenovirus particles) (see, e.g., Curiel et al. 1992 Am. J. Respir. Cell Mol. Biol. 6.247-52)). Thus "non-viral delivery vehicle" can include vectors composed of polynucleotides plus viral particles where the viral particles do not contain the polynucleotide of interest. "Non-viral delivery vehicles" include bacterial plasmids, viral genomes or portions thereof, wherein the polynucleotide to be delivered is not encapsidated or contained within a viral particle, and constructs comprising portions of viral genomes and portions of bacterial plasmids and/or bacteriophages. The term also encompasses natural and synthetic polymers and co-polymers. The term further encompasses lipid-based vehicles. Lipid-based vehicles include cationic liposomes such as disclosed by Felgner et al (U.S. Pat. Nos. 5,264,618 and 5,459,127; PNAS 84:7413-7417, 1987; Annals N.Y. Acad. Sci. 772:126-139, 1995); they may also consist of neutral or negatively charged phospholipids or mixtures thereof including artificial viral envelopes as disclosed by Schreier et al. (U.S. Pat. Nos. 5,252,348 and 5,766,625).

Non-viral delivery vehicles include polymer-based carriers. Polymer-based carriers may include natural and synthetic polymers and co-polymers. Preferably, the polymers are biodegradable, or can be readily eliminated from the subject. Naturally occurring polymers include polypeptides and polysaccharides. Synthetic polymers include, but are not limited to, polylysines, and polyethyleneimines (PEI; Boussif et al., PNAS 92:7297-7301, 1995) which molecules can also serve as condensing agents. These carriers may be dissolved, dispersed or suspended in a dispersion liquid such as water, ethanol, saline solutions and mixtures thereof. A wide variety of synthetic polymers are known in the art and can be used.

"Non-viral delivery vehicles" further include bacteria. The use of various bacteria as delivery vehicles for polynucleotides has been described. Any known bacterium can be used as a delivery vehicle, including, but not limited to non-pathogenic strains of Staphylococcus, Salmonella, and the like.

Formulations for Nucleic Acid Delivery

The polynucleotide to be delivered can be formulated as a DNA- or RNA-liposome complex formulation. Such complexes comprise a mixture of lipids which bind to genetic material (DNA or RNA) by means of cationic charge (electrostatic interaction). Cationic liposomes which may be used in the present invention include $3\beta$-[N-(N',N'-dimethyl-aminoethane)-carbamoyl]-cholesterol (DC-Chol), 1,2-bis(oleoyloxy-3-trimethylammonio-propane (DOTAP) (see, for example, WO 98/07408), lysinylphosphatidylethanolamine (L-PE), lipopolyamines such as lipospermine, N-(2-hydroxyethyl)-N,N-dimethyl-2,3-bis(dodecyloxy)-1-propanaminium bromide, dimethyl dioctadecyl ammonium bromide (DDAB), dioleoylphosphatidyl ethanolamine (DOPE), dioleoylphosphatidyl choline (DOPC), N(1,2,3-dioleyloxy)propyl-N,N,N-triethylammonium (DOTMA), DOSPA, DMRIE, GL-67, GL-89, Lipofectin, and Lipofectamine (Thiery et al. (1997) Gene Ther. 4:226-237; Felgner et al., Annals N.Y. Acad. Sci. 772:126-139, 1995; Eastman et al.; Hum. Gene Ther. 8:765-773, 1997). Polynucleotide/lipid formulations described in U.S. Pat. No. 5,858,784 can also be used in the methods described herein. Many of these lipids are commercially available from, for example, Boehringer-Mannheim, and Avanti Polar Lipids (Birmingham, Ala.). Also encompassed are the cationic phospholipids found in U.S. Pat. Nos. 5,264,618, 5,223,263 and 5,459,127. Other suitable phospholipids which may be used include phosphatidylcholine, phosphatidylserine, phosphatidylethanolamine, sphingomyelin, phosphatidylinositol, and the like. Cholesterol may also be included.

Utility

The subject compositions and methods of modulating sensitivity to insulin and/or leptin in a host find use in a variety of protocols. In some embodiment, these protocols involve administering to a host an effective amount of one or more active agents that alter DGAT1 activity in the host and thereby modulate carbohydrate metabolism in the host. In other embodiments, these protocols involve administering to a host suffering from a condition associated with abnormal carbohydrate metabolism an effective amount of one or more active agents that modulate DGAT activity in the host and treat the host for the condition.

By treatment is meant at least an amelioration of a symptom associated with the pathological condition afflicting the host, where amelioration is used in a broad sense to refer to at least a reduction in the magnitude of a parameter, e.g., symptom, associated with the pathological condition being treated. Treatment also includes outcomes where the pathological condition, or at least symptoms associated therewith, are completely inhibited, e.g. prevented from happening, or stopped, e.g., terminated, such that the host no longer suffers from the pathological condition, or at least the symptoms that characterize the pathological condition. For example, where the disease condition is marked by the presence of variable blood glucose levels, treatment includes at least a reduction in the variability of blood glucose levels, including a restoration of stable blood glucose levels of a normal host.

In certain other embodiments, insulin, leptin or a mimetic thereof is administered before, at the same time as, or after the DGAT activity modulating agent in order to modulate carbohydrate metabolism or treat a condition associated with abnormal carbohydrate metabolism. It is expected that such combinations, e.g., a formulation including insulin and/or leptin and a DGAT modulatory agent will be efficacious in treating a disease relating to abnormal carbohydrate metabolism.

A variety of hosts may be used in the subject methods. Generally such hosts are mammals or mammalian, where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Of particular interest is treatment and prevention of diseases relating to abnormal carbohydrate metabolism associated with increased sensitivity to insulin and/or leptin. Such diseases include blood glucose-related disorders (diabetes) and obesity, including, blood glucose-related disorders, including diabetic microangiopathies (diabetic nephropathy, diabetic neuropathy, and diabetic retinopathy), impaired glucose tolerance, hyperinsulinemia, hyperlipemia, arteriosclerosis, hypertension, obesity, ischemic heart diseases, ischemic brain disorders, peripheral arterial embolism, diabetes mellitus, diabetes insipidus, gestational diabetes, diabetes innocens, diabetes insipidus, nephrogenic diabetes insipidus, diabetes intermittens, diabetes mellitus; insulin-dependent diabetes mellitus, lipoatrophic diabetes mellitus, non-insulin-dependent diabetes mellitus, type 1 diabetes and type 2 diabetes; and disorders relating to obesity, including diabetes, type 2 diabetes, hypertension, stroke, myocardial infarction or congestive heart failure, prostate and colon cancer, gallstones, cholecystitis, gout, gouty arthritis osteoarthritis, degenerative arthritis of the knees, hips, or the lower back, apnea, and pickwickian syndrome.

The subject methods also find use in the modulation of carbohydrate metabolism in hosts not suffering from a particular condition but in which the modulation of carbohydrate metabolism is nonetheless desired. Subject treatment methods are typically performed on hosts with such disorders or on hosts with a desire to avoid contracting such disorders. As such, the invention also contemplates preventing or reducing the risk of a disease relating to abnormal carbohydrate metabolism in a host by administering a pharmaceutical composition, and for achieving a desired outcome that is not abnormal, but otherwise desirable, for example weight loss of a non-obese host, or a decrease in blood glucose levels in a non-diabetic host.

In particular, modulation of glucose uptake and glycogen synthesis in muscle or liver cells, or lipid (e.g. triacylglycerol) transport, synthesis, and storage e.g. in adipocyte cells is of interest.

Kits

Also provided by the subject invention are kits for practicing the subject methods, as described above. The subject kits at least include one or more of a pharmaceutical preparation comprising at least one active agent that modulates DGAT activity, such as those representative DGAT1 modulatory agents described above. Other optional components of the kit include: a syringe or another administration device, and glucose-monitoring devices such as glucose test strips, etc. Also included in the kit may be insulin, leptin, or an activity mimetic thereof. The various components of the kit may be present in separate containers or certain compatible components may be pre-combined into a single container, as desired. In many embodiments, kits with unit doses of the active agent, e.g., in oral or injectable doses, are provided. In many embodiments the subject composition is contained within a media, such as a media suitable for injection into a human bloodstream.

In addition to above-mentioned components, the subject kits typically further include instructions for using the components of the kit to practice the subject methods treating a host suffering from a disease relating to abnormal carbohydrate metabolism by administering to said host an effective amount of one or more active agents that modulate DGAT in the host to modulate sensitivity to insulin and/or leptin sensitivity in the host and treat the host for the condition. The instructions for practicing the subject methods are generally recorded on ah suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Animal Models for Modulated Sensitivity to Insulin and/or Leptin

The invention further provides a non-human animal model for modulated sensitivity to insulin and/or leptin. In general, the non-human animal model is characterized by having abnormal DGAT activity.

A non-human animal may be any animal, e.g., a mammal or avian species that can serve as an animal model for testing therapies sensitivity to insulin and/or leptin. In many embodiments the non-human animal is a laboratory animal, usually a rodent, e.g., mouse, rat, hamster, guinea pig or the like. Other suitable laboratory animals are rabbits, cats, dogs, small monkeys, and apes. In addition, certain farm animals are also often employed as laboratory animals, notably chickens, goats, sheep, and pigs. Mice suitable for use in the present invention can be produced from any of a variety of background strains including, but not necessarily limited to, the strains C.B-17, C3H, BALB/c, C57131/6, AKR, BA, B10, 129, etc. Non-human animals are readily available from researchers or commercial suppliers, such as Jackson Laboratories (Bar Harbor, Me.), Charles River Breeding Laboratories (Wilmington, Mass.), Taconic Farms (Germantown, N.Y.), to mention a few such suppliers.

DGAT activity, including DGAT1 and/or DGAT2 activity, may be modified in animals by a variety of methods. In many embodiments, these methods involve modifying the expression of DGAT in a transgenic animal. In many embodiments, the expression of a DGAT endogenous to the animal is reduced in an animal. This may be accomplished through knockout strategies, where an nucleic acid insertion into an endogenous gene inactivates the gene (described in U.S. Pat. Nos. 5,487,992; 5,627,059; 5,631,153; and 6,204,061), or by other methods e.g. antisense, inhibitory RNA (RNAi), ribozyme or co-supression technologies, as is known in the art (e.g. Hannon et al., Nature 418:244-51, 2002; Ueda, J Neurogenet. 15:193-204, 2001; Review. Lindenbach et al., Mol Cell. 9:925-7, 2002; Brantl, Biochim Biophys Acta. 1575:15-25, 2002; Zhang et al., Ann N Y Acad Sci. 923:210-33, 2000). In other embodiments, an endogenous or exogenous DGAT is over-expressed in an animal. In these embodiments, a DGAT, leptin or leptin receptor coding sequence (for example, a coding sequence provided by one of the following NCBI accession: NM_010046 (SEQ ID NO:1), XM_035370 (SEQ ID NO:2), NM_053437 (SEQ ID NO:3), AJ318490 (SEQ ID NO:4), AF221132 (SEQ ID NO:5), AF468649 (SEQ ID NO:6), AY093657 (SEQ ID NO:7), AF384161 (SEQ ID NO:8), NM_012079 (SEQ ID NO:9), AF384163 (SEQ ID NO:10), AF384162 (SEQ ID NO:11), AF078752 (SEQ ID NO:12), is cloned into an expression cassette in an appropriate vector, and transferred into the genome of an animal to make a transgenic animal. In certain embodiments, the animal is homozygous for a defect in a DGAT gene (DGAT1 or DGAT2), and in many embodiments, the subject animal is homozygous for a knockout in one of these genes.

Cloning technology, cloning strategies, expression cassettes, and suitable vectors for performing animal transformation are well known in the art (Ausubel, et al, *Short Protocols in Molecular Biology*, 3rd ed., Wiley & Sons, 1995; Sambrook, et al., *Molecular Cloning: A Laboratory Manual*, Second Edition, (1989) Cold Spring Harbor, N.Y.). Methods of generating transgenic, non-human animals, particularly transgenic, non-human mammals, are also known in the art. See, e.g., U.S. Pat. Nos. 6,268,545; 6,255,554; 6,222,094; 5,387,742, 4,736,866 and 5,565,186 and 6,204,43; "Transgenic Animal Technology" C. A. Pinkert, ed. (1997) Acad. Press; "Gene Knockout Protocols" M. J. Tymms, et al., eds. (2001) Humana Press; and "Gene Targeting: A Practical Approach" A. L. Joyner, ed. (2000) Oxford Univ. Press.

One method for producing a transgenic animal employs embryonic stem (ES) cells obtained from an animal to be transformed, e.g. mouse, rat, guinea pig, etc. In these methods, ES cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected. Progeny of transgenic animals may be screened for the presence of the modified gene and males and females having appropriate modified genomes are mated to produce homozygous progeny.

In certain embodiments, transgenic animals may be intercrossed or may contain more than one genetic modification in order to produce a subject animal model. For example, an animal overexpressing DGAT1 may be bred with an animal knockout of a leptin-encoding gene to produce an subject animal model containing an increase in DGAT activity and a decrease in leptin activity and an animal overexpressing leptin may also be bred with an animal knockout of a DGAT-encoding gene to produce an a subject animal model containing a decrease in DGAT activity and an increase in leptin activity, etc. Animals with abnormal DGAT expression may be intercrossed with animals containing abnormal expression of other genes (e.g. obese, agouti yellow) in order to produce a subject animal model.

In embodiments where DGAT is over-expressed in a subject animal, DGAT activity is increased more than about 1.5-fold, more than about 2-fold, more than about 3-fold, more than about 5-fold, more than about 10-fold or even more than about 100-fold in a subject animal, as compared to an animal in which DGAT expression is not increased.

In embodiments where DGAT expression is decreased in a subject animal, DGAT expression is decreased by more than about 30%, more than about 50%, more than about 70%, more than about 90%, more than about 95% or even more than about 98%, about 99% or 99.5% in a subject animal, as compared to an animal in which DGAT is not decreased.

The subject animals have abnormal sensitivity to insulin and/or leptin relative to a normal animal of the same species. In certain embodiments, the features exhibited by the subject animals include, but are not limited to, increased or decreased blood glucose, increased or decreased blood insulin, increased or decreased body weight, increased or decreased physical activity, increased or decreased gat pad content, and increased or decreased sensitivity to insulin and/or leptin. In these embodiment, subject animal features may be increased or decreased by about 10% or more, about 20% or more, about 30% or more, about 50% or more, about 70% or more, about 80% or more, about 90% or more, or even about 95% or more as compared to a normal animal of the same species. Such animals find use in a variety of applications, including the screening methods described below.

Screening Assays

The invention further provides methods of screening a candidate agent for an activity that modulates sensitivity to insulin and/or leptin, e.g. stimulators or inhibitors of sensitivity to insulin and/or leptin. These screening assays typically provide for qualitative/quantitative measurements of a phenomenon associated with sensitivity to insulin and/or leptin in the presence of a particular candidate agent. The screening methods be performed in vivo, in vitro or in a cell free system, which are readily developed by those of skill in the art. Test agents that have a desirable effect in any subject screening assay method find use in a variety of applications, including modulating sensitivity to insulin and/or leptin in a host, modulating carbohydrate metabolism in a host, or treating a disorder associated with carbohydrate metabolism.

Using the above screening methods, a variety of different agents may be identified. Such agents may target the DGAT enzyme itself or an expression regulatory factor thereof. Such agents may be inhibitors or promoters of DGAT activity, where inhibitors are those agents that result in at least a reduction of DGAT activity as compared to a control and enhancers result in at least an increase in DGAT activity as compared to a control. Specific screening assay methods are described below.

In Vivo Assays

The invention provides in vivo methods of screening a candidate agent for an activity that modulates sensitivity to insulin and/or leptin. In general, the method involves administering a candidate agent to an animal, particularly a subject transgenic animal and determining the effect of the candidate agent on sensitivity of the animal to insulin and/or leptin.

The invention further provides in vivo methods of screening a candidate agent for an activity that modulates carbohydrate metabolism. In general, the method involves administering a candidate agent to an animal, particularly a subject transgenic animal and determining the effect of the candidate agent on a phenomenon associated with carbohydrate metabolism.

The invention further provides in vivo methods of screening a candidate agent for an activity that reduces a symptom of a condition associated with abnormal carbohydrate metabolism. In general, the method involves administering a candidate agent to an animal, particularly a subject transgenic animal and determining the effect of the candidate agent on a phenomenon associated with carbohydrate metabolism.

In many embodiments the determining step of the in vivo assay method involves measuring a certain phenomenon associated with sensitivity to insulin and/or leptin or a phenomenon associated with carbohydrate metabolism including, but not limited to: insulin sensitivity or tolerance, leptin sensitivity or tolerance, lipid composition, adipocyte size, blood glucose levels, glucose disposal, glucose tolerance, insulin tolerance, weight loss, food intake, triacylglycerol content or composition, energy expenditure, weight, weight gain, activity or an alteration in lipid content and the like.

In certain embodiments, the subject animals are placed on a high fat diet, or a glucose-rich diet, before, during or after administration of the candidate agent, and compared to similarly fed controls.

In vivo assays of the invention include controls, where suitable controls include a sample in the absence of the test agent. Generally a plurality of assay mixtures is run in parallel with different agent concentrations to obtain a differential response to the various concentrations. Typically, one of these concentrations serves as a negative control, i.e. at zero concentration or below the level of detection.

A candidate agent of interest is one that modulates, i.e., reduces or increases, DGAT activity, DGAT expression, lipid (e.g. TAG) composition, adipocyte size, blood glucose levels, glucose disposal, glucose tolerance, insulin tolerance, weight loss, food intake, triacylglycerol content or composition, energy expenditure, weight, weight gain, activity or alters lipid content etc., by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to a control in the absence of the test agent. In general, a candidate agent will cause a subject animal to be more similar to an equivalent animal that is not altered in DGAT activity.

In Vitro Assays

The invention provides in vitro methods of screening a candidate agent for an activity that modulates sensitivity to insulin and/or leptin. In general, the methods involve contacting a cell with abnormal DGAT activity with a candidate agent and determining the effect of the agent on the cell in order to assess the candidate agent's activity that modulates sensitivity to insulin and/or leptin.

In many embodiments, the cell with abnormal DGAT activity is an in which DGAT gene expression has been modified as compared to an unaltered cell. Methods for altering gene expression in a cell are well known to one of skill in the art (discussed in Ausubel, et al, *Short Protocols in Molecular Biology*, 3rd ed., Wiley & Sons, 1995; Sambrook, et al., *Molecular Cloning: A Laboratory Manual*, Second Edition, (1989) Cold Spring Harbor, N.Y.). These methods may involve DGAT overexpression via introduction of a genetic construct designed to express DGAT coding sequences, or may involve downregulating DGAT expression via knockout strategies (described in U.S. Pat. Nos. 5,487,992; 5,627,059; 5,631,153; and 6,204,061), or by other methods e.g. antisense, inhibitory RNA (RNAi), ribozyme or co-supression technologies, as is known in the art (e.g. Hannon et al., Nature 418:244-51, 2002; Ueda, J Neurogenet. 15:193-204, 2001; Review. Lindenbach et al., Mol Cell. 9:925-7, 2002; Brantl, Biochim Biophys Acta. 1575:15-25, 2002; Zhang et al., Ann N Y Acad Sci. 923:210-33, 2000).

In embodiments where DGAT is overexpressed in a cell, DGAT expression is increased more than about 1.5-fold, more than about 2-fold, more than about 3-fold, more than about 5-fold, more than about 10-fold or even more than about 100-fold in the cell, as compared to an cell in which DGAT is not increased.

In embodiments where DGAT expression is decreased in a cell, DGAT expression is decreased by more than about 30%, more than about 50%, more than about 70%, more than about 90%, more than about 95% or even more than about 98%; about 99% or 99.5% in the, as compared to a cell in which DGAT is not decreased.

Methods for measuring insulin sensitivity in a cell are well known in the art, and generally involve contacting a cell with insulin or a mimetic, and assaying glucose uptake (or, for example, 2-deoxyglucose, 3-O-methylglucose, hexose, methylaminoisobutyric acid etc.), glycogen synthesis, or the expression of certain genes such as glycogen synthase. Many cell lines may be used for these methods, including fibroblast cell lines, muscle cell lines, and hepatoma cell lines. Exemplary publications describing insulin sensitivity assays are: Klein et al. (Bioessays, 24:382-8, 2002), Crook et al, (Diabetes 44:314-20, 1995), Saribia et al. (Biochem Cell Biol 68:536-42, 1990), Meienhofer et al., (Eur J Biochem 169: 237-43, 1987), Grunfeld et al. (Endocrinology 113:1763-70, 1983) and several other assays would be immediately apparent to one of skill in the art.

Methods for measuring leptin sensitivity are also well known the art, and may be performed on a number of cell lines, including human breast cells, pituitary cells, hepatoma cells and pancreatic cells. Exemplary publications describing insulin sensitivity assays are: Smith et al., (Domest Anim Endocrinol. 22:145-54, 2002), Tsumanuma et al., (Pituitary, 3:211-20, 2000), Kaser et al., (Int J Obes Relat Metab Disord. 25:1633-9, 2001), Tanizawa et al., (Endocrinology. 138:4513-6, 1997) and Gainsford et al., (Proc Natl Acad Sci 93: 14564-8, 1996) and several other assays would be immediately apparent to one of skill in the art.

In certain embodiments the subject cell is a cell from a subject model animal. In these embodiments a cell from a subject animal model is isolated and may be cultured to produce a cell that has altered DGAT activity.

In certain embodiments the determining step of the in vitro assay method involves measuring DGAT activity, DGAT expression, lipid (e.g. TAG) biosynthesis, deposition or secretion and the like.

In vitro assays of the invention include controls, where suitable controls include a sample in the absence of the test agent. Generally a plurality of assay mixtures is run in parallel with different agent concentrations to obtain a differential response to the various concentrations. Typically, one of these concentrations serves as a negative control, i.e. at zero concentration or below the level of detection.

A test agent of interest is one that modulates, i.e., reduces or increases, DGAT activity, DGAT expression, lipid (e.g. TAG) biosynthesis, deposition or secretion, or sensitivity to insulin and/or leptin by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to a control in the absence of the test agent. In general, a test agent will cause a subject cell to be more similar to an equivalent cell that is not altered in DGAT activity.

Cell Free Assays

The invention provides cell free methods of screening a candidate agent for an activity that modulates sensitivity to insulin and/or leptin. In general, the methods-involve admixing an extract of a cell (or a synthetic mimetic thereof) with DGAT activity, or isolated DGAT polypeptide, with a candidate agent and determining the effect of the agent on the extract in order to assess the candidate agent's activity that modulates sensitivity to insulin and/or leptin. In many embodiments the assay methods involve measuring DGAT activity, lipid (e.g. TAG) biosynthesis, or and the like, Cell free assays of the invention include controls, where suitable controls include a sample in the absence of the candidate agent. Generally a plurality of assay mixtures is run in parallel with different agent concentrations to obtain a differential response to the various concentrations. Typically, one of these concentrations serves as a negative control, i.e. at zero concentration or below the level of detection.

A test agent of interest is one that modulates, i.e., reduces or increases, DGAT activity, lipid biosynthesis or the like, by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to a control in the absence of the test agent. In general, a candidate agent will cause a subject extract to be more similar to an equivalent extract from a cell that is not altered in DGAT activity.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used.

Candidate Agents

The terms "candidate agent," "test agent", "agent", "substance" and "compound" are used interchangeably herein and describe a variety of agents that may be screened using the above methods.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modeling. For example, numerous means are available for random and directed synthesis of a wide variety of organic compounds and biomolecules, including expression of randomized oligonucleotides and oligopeptides.

Screening may be directed to known pharmacologically active compounds and chemical analogs thereof, or to new agents with unknown properties such as those created through rational drug design.

A variety of other reagents may be included in screening assays. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, anti-microbial agents, etc. may be used. The mixture of components is added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hour will be sufficient.

Candidate agents may also include biopolymers, including nucleic acids (e.g. DNA, RNA, cDNA, plasmids and this like), for example those encoding DGAT1 or DGAT2, or antisense DGAT1 or DGAT2 nucleic acids and the like, carbohydrates, lipids (e.g. lipids that inhibit the activity of DGAT) and proteins and polypeptides, (such as DGAT1 or DGAT2 or an antibody specific for DGAT1 or DGAT2).

In particular embodiments, the candidate agent may be niacin, or other agents known in the art, e.g. those described in Lesnik et al. (Arch Dermatol Res 1992; 284(2):100-5).

Agents that have an effect in an assay method of the invention may be further tested for cytotoxicity, bioavailability, and the like, using well known assays. Agents that have an effect in an assay method of the invention may be subjected to directed or random and/or directed chemical modifications, such as acylation, alkylation, esterification, amidification, etc. to produce structural analogs. Such structural analogs include those that increase bioavailability, and/or reduced cytotoxicity. Those skilled in the art can readily envision and generate a wide variety of structural analogs, and test them for desired properties such as increased bioavailability and/or reduced cytotoxicity and/or ability to cross the blood-brain barrier.

The following examples are presented for purposes of illustration only, and are not to be construed as limiting on the scope of the invention in any way.

EXPERIMENTAL

Materials and Methods

Mice: Dgat1$^{-/-}$ mice (about 95% C57BL/6 and 5% 129/SvJae background) were generated previously (Smith, et al. (2000) Nat. Genet. 25:87-90). A P1 clone containing mouse Dgat (Genome Systems) and subcloned an ~15-kb XbaI fragment into pBSSKII. A sequence replacement vector was constructed in pKSloxPNT by amplifying and subcloning a 0.85-kb upstream short-arm fragment containing 5' coding sequences (primers: 5'-GTTCATCGATCTTTATTCCTAC-CGGGATG-3' (SEQ ID NO:30); and 5'-AGAAGGTCGAC-CACAGCATTGAGACAGGAGTG-3' (SEQ ID NO:31)) and a 12-kb downstream long-arm fragment containing the Dgat stope codon and polyadenylation signal (primers: 5'-tgctt-tagggcgcgccTGAGGTACTGCCAAAGGCCAG-3' (SEQ ID NO:32), lower-case indicates nucleotides added to engineer an AscI site for cloning purposes; and a plasmid T3 primer). This vector was used to generate targeted embryonic stem cells and mice. The disrupted allele was confirmed by hybridizing EcoRI-digested genomic DNA with a $^{32}$P-labelled 0.6-kb fragment located 5' of the short arm of homology. Subsequence genotyping in mice was performed by PCR with primers A (5'-CTCCATGAAGCCCTTCAAGG-3' (SEQ ID NO:33)), B (5'-TGTGCACGGGGATATTCCAG-3' (SEQ ID NO:34)) and C (5'-TACCGGTGGATGTGGAATGTGT-GCG-3' (SEQ ID NO:35)) in a 35-cycle reaction (96° C. for 30 s, 50° C. for 1 min, and 72° C. for 2 min). A and B amplify an ~450-bp fragment from the wild-type allele, and A and C amplify an ~550-bp fragment from the mutant allele. Wild-type (Dgat1$^{+/+}$), ob/+, and A$^Y$/a mice (all in C57BL/6 background) were from The Jackson Laboratory (Bar Harbor, Me., USA). A$^Y$/a mice are obese and insulin resistant, reflecting the antagonism of melanocyte-stimulating hormone in the hypothalamus. They are also severely leptin resistant. Genotyping for Dgat1 and ob was performed as described (Smith et al., supra). A$^Y$/a mice were identified by their yellow fur. Mice were housed in a pathogen-free barrier facility (12-hour light/12-hour dark cycle) and fed rodent chow (Ralston Purina Co., St. Louis, Mo., USA). For high-fat diet experiments, mice were fed a Western-type diet containing 21% fat by weight (Harlan Teklad Laboratory, Madison, Wis., USA) for 4 weeks unless stated otherwise. All experiments were approved by the Committee on Animal Research of the University of California, San Francisco.

Tissue lipid analysis: Tissue lipids were extracted and separated by TLC as described (Smith et al., supra). Triglycerides and diacylglycerol were scraped from the TLC plate, and heptadecanoic acid (about 10% of total fatty acids) was added as an internal standard. Methyl esters were synthesized with the addition of methanolic HCl/toluene (4:1 vol/vol) to the TLC adsorbent for 12 hours at 37° C., extracted with hexane, and analyzed with gas-liquid chromatography (HP6890 Gas Chromatograph; Hewlett-Packard, Palo Alto, Calif., USA). Methyl esters were separated with a 10-ft glass column (10% SP-2330 on 100/120 Chromosorb WAW; Supelco, St. Louis, Mo., USA) at 175° C. for 5 minutes and increasing to 210° C. at a rate of 2.5° C./min. The weight of triglycerides and diacylglycerol in the samples was calculated with reference to the internal standard.

Adipocyte size determination: Adipose tissue was obtained from the reproductive fat pads of 14-week-old male mice. The samples were fixed in paraformaldehyde, embedded in paraffin, cut into 5-μm sections, and stained with hematoxylin and eosin. Images of the histology sections were analyzed with Adobe Photoshop 5.0.1 (Adobe Systems Inc., San Jose, Calif., USA) and Image Process Tool Kit (Reindeer Games, Gainesville, Fla., USA) as described (Chen and Farese, J. Lipid Res. 43:986-9, 2002).

Glucose metabolism studies: Glucose (1 g/kg, body wt) or bovine insulin (1 U/kg body wt; Sigma Chemical Co., St. Louis, Mo., USA) was injected intraperitoneally, and glucose concentrations were measured with a glucometer (Accu-Chek; Roche Diagnostics Corp., Indianapolis, Ind., USA). The hyperinsulinemic-euglycemic clamp studies were performed as described (Ferriera Diabetes. 50:1064-1068, 2001) with slight modifications. Weight-matched 10- to 14-week-old male mice were fasted for 4 hours before the clamp studies. Insulin was infused at 20 mU/kg/min, and plasma glucose concentration was clamped at 120 mg/dl. For ob/ob and A$^Y$/a mice, nonfasting blood samples for glucose and insulin measurements were obtained at noon. Insulin was measured with a rat insulin RIA kit (Linco Research Inc., St. Charles, Mo., USA).

Leptin infusion studies: Mice were infused with recombinant human leptin (gift from F. Chehab, University of California, San Francisco) with a microosmotic pump (Alza model 1002; DURECT Corp., Cupertino, Calif., USA) inserted subcutaneously into the interscapular region. Plasma leptin levels were measured by AniLytics Inc. (Gaithersburg, Md., USA).

Northern blots. White adipose tissue (WAT) was obtained from the reproductive fat pads and brown adipose tissue (BAT) from the interscapular region of 10- to 14-week-old male mice. Total RNA was isolated, and pooled RNA samples (10 μg) were subjected to electrophoresis and blot hybridization with $^{32}$P-labeled cDNA probes. Blots were rehybridized with a β-actin probe (Ambion Inc., Austin, Tex., USA) for loading normalization. Probes for uncoupling protein 2 (UCP-2) and UCP-3 were generated by PCR with WAT cDNA and the following primers: 5'-GTCGATTCCGC-CCTCGGTG-3'(SEQ ID NO:13), 5'-GAGGGAAAGTGAT-GAGATCT-3' (SEQ ID NO:14)(UCP-2); 5'-GTCGGACA-CAGCCTTCTGC-3', (SEQ ID NO:15)5'-ACCTTGGACCGCCAGCCGG-3'(SEQ ID NO:16)(UCP-3). The remaining probes were gifts from M. Reitman, NIH, Bethesda, Md., USA (UCP-1); B. Staels, Institut National de la Santé et de la Recherche Médicale (Lille, France) (acyl CoA oxidase); B. Spiegelman, Dana-Farber Cancer Institutes, Boston, Mass., USA (peroxisome proliferator-activated receptor); and I. Shimomura, M. Brown, and J. Goldstein, University of Texas Southwestern, Dallas, Tex., USA (fatty acid synthase). Signals were quantified with a PhosphorImager (Bio-Rad Laboratories, Hercules, Calif., USA).

Real-time PCR. Tissues were homogenized, and total RNA was extracted. RNA (1 μg) was reverse-transcribed in a 20-μl reaction containing oligo(dT)$_{12-18}$ primer and Superscript II enzyme (Invitrogen Corp., Carlsbad, Calif., USA). Primer and probe sequences (Table 1) were selected with Primer Express (Perkin-Elmer Applied Biosystems, Foster City, Calif., USA). The PCR reaction (50 µl) contained 1 µl of cDNA, 1×Gold buffer, 4 mM $MgCl_2$, 500 µM dNTP, primers (200 nM), 100 nM probe (labeled with 6-carboxyfluorescein), and 1.25 U of AmpliTaq Gold DNA polymerase (Perkin-Elmer Applied Biosystems). Real-time PCR was performed with the ABI Prism 7700 System (Perkin-Elmer Applied Biosystems). Expression levels were calculated by the comparative cycle of threshold detection method, according to the manufacturer. Expression of β-actin was used for loading normalization.

Statistical methods: Data are shown as mean±SD unless stated otherwise. Measurements were compared with the t test or Mann-Whitney rank-sum test. Differences in body weight or food intake were compared with ANOVA, followed by the Tukey-Kramer test.

members is deleted. The gene targeting vector was electroporated into RF8 embryonic stem cells by electroporation, and several targeted clones were identified by Southern blotting (targeting frequency of ~1 in 300).

One of these targeted clones was injected into C57BL/6 blastocysts and chimeras were generated; male chimeras subsequently passed the DGAT knockout mutation through the germline to their offspring. The resultant mice, which were heterozygous for the DGAT gene disruption, were intercrossed to generate mice that were homozygotes.

Inactivation of the DGAT gene in the homozygote knockouts was verified by examining DGAT mRNA which was found to be absent in the knockout mice. In activation of the DGAT gene was also verified by studying DGAT activity in tissues using an assay that measures the incorporation of [14C]oleoyl CoA into triglycerides. The results from the activity assays show that DGAT activity is virtually gone from every nearly every tissue tested.

TABLE 1

Real-time PCR primer and probe sequences

| Gene | Primer pair or probe | Sequence |
|---|---|---|
| Actin | 5' | 5'-CATCTTGGCCTCACTGTCCA-3' SEQ ID NO: 17 |
|  | 3' | 5'-GGGCCGGACTCATCGTACT-3' SEQ ID NO: 18 |
|  | Probe | 5'-CTTCCAGCAGATGTGGATCAGCAAGC-3' SEQ NO: 19 |
| DGAT2 | 5' | 5'-AGTGGCAATGCTATCATCATCGT-3' SEQ ID NO: 20 |
|  | 3' | 5'-AAGGAATAAGTGGGAACCCAGATCA-3' SEQ ID NO: 21 |
|  | Probe | 5'-CCTGGCAAGAACGCAGTCACCCTG-3' SEQ ID NO: 22 |
| Leptin | 5' | 5'-TCTCCGAGACCTCCTCCATCT-3' SEQ ID NO: 23 |
|  | 3' | 5'-TTCCAGGACGCCATCCAG-3' SEQ ID NO: 24 |
|  | Probe | 5'-TCCCTGCCTCAGACCAGTGGCCT-3' SEQ ID NO: 25 |
| PPARα | 5' | 5'-CAGGAGAGCAGGGATTTGCA-3' SEQ ID NO: 26 |
|  | 3' | 5'-CCTACGCTCAGCCCTCTTCAT-3' SEQ ID NO: 27 |
|  | Probe | 5'-AGAGGGCCTCCCTCCTACGCTTGG-3' SEQ ID NO: 28 |

Example I

Preparation and Characterization of DGAT Knockout Mice

DGAT knockout mice were generated using standard techniques of gene targeting. A mouse P1 clone containing the mouse DGAT gene was isolated from a genomic 129/Sv library. Short and long arms of homologous sequences were amplified by PCR from this clone and subcloned intopNTK-LoxP to generate a gene targeting vector. The vector contained a neomycin resistance gene for positive selection and a thymidine kinase gene for negative selection. Upon homologous recombination, the vector was designed to interrupt the DGAT coding sequences at amino acid 360 of the 498-amino acid murine protein. The entire C-terminus, including a highly conserved region common to all ACAT gene family Example II Altered Lipid Composition in Tissues of Dgat1$^{-/-}$ Mice Dgat1$^{-/-}$ mice had a 30-40% reduction of triglyceride levels in WAT and skeletal muscle (Table 2). Liver triglyceride levels trended lower in chow-fed Dgat1$^{-/-}$ mice. On a high-fat diet, however, Dgat1$^{-/-}$ mice had significantly lower liver triglyceride levels than Dgat1$^{+/+}$ mice (28±16 versus 157±28 mg/g tissue weight, P<0.05). Unexpectedly, levels of diacylglycerol, a substrate for the DGAT reaction, were not elevated, and in fact tended to be lower in Dgat1$^{-/-}$ tissues (Table 2). DGAT1 deficiency also altered the fatty acid composition of triglycerides in WAT and skeletal muscle, resulting in a relative decrease in monounsaturated (16:1 and 18:1) fatty acids and a relative increase in saturated (16:0 and 18:0) fatty acids (Table 2).

mice (0.7±0.1 versus 0.5±0.2 ng/ml for 6 µg/day, P>0.05). In young (10- to 14-week-old) Dgat1$^{+/+}$ mice, leptin administration suppressed the normal weight gain seen in control

TABLE 2

Lipid composition of tissues in Dgat1$^{-/-}$ and Dgat1$^{+/+}$ mice

|  | Triglycerides | Diacylglycerol | \multicolumn{7}{c}{Fatty acid composition of triglycerides (% of total fatty acids)} |
|---|---|---|---|---|---|---|---|---|---|
|  | (% of tissue weight) |  | 16:0 | 16:1 | 18:0 | 18:1 | 18:2w6 | 18:3w6 | 18:3w3 |
| White adipose tissue | | | | | | | | | |
| +/+ | 32.4 ± 7.9 | 0.06 ± 0.02 | 20.0 ± 0.6 | 8.4 ± 1.2 | 1.8 ± 0.2 | 37.3 ± 1.2 | 25.3 ± 1.9 | 0.3 ± 0.3 | 0.7 ± 0.1 |
| -/- | 20.3 ± 3.0$^A$ | 0.04 ± 0.1 | 26.4 ± 1.5$^B$ | 4.5 ± 1.4$^B$ | 3.8 ± 1.0$^B$ | 34.2 ± 1.3$^A$ | 25.3 ± 3.4 | 0.1 ± 0.3 | 0.9 ± 0.4 |
| Skeletal muscle | | | | | | | | | |
| +/+ | 4.3 ± 1.9 | 0.008 ± 0.002 | 21.0 ± 2.0 | 7.7 ± 1.1 | <0.001 | 38.0 ± 1.9 | 24.3 ± 2.8 | 0.2 ± 0.2 | 1.1 ± 0.6 |
| -/- | 2.4 ± 0.5$^A$ | 0.006 ± 0.003 | 27.3 ± 0.7$^B$ | 3.1 ± 1.1$^B$ | <0.001 | 33.5 ± 1.7$^A$ | 23.3 ± 2.8 | 0.3 ± 0.2 | 1.3 ± 0.4 |
| Liver | | | | | | | | | |
| +/+ | 0.2 ± 0.1 | 0.013 ± 0.003 | ND | ND | ND | ND | ND | ND | ND |
| -/- | 0.1 ± 0.0 | 0.003 ± 0.001$^A$ | | | | | | | |

Twelve- to sixteen-week-old male mice fed a chow diet were used.
ND, not determined.
$^A$P < 0.05,
$^B$P < 0.01 versus Dgat1$^{+/+}$.
n = 3 per genotype.

Example III

Decreased Adipocyte Size in Dgat1$^{-/-}$ Mice

Concomitant with the decreased triglyceride levels in WAT, Dgat1$^{-/-}$ mice had smaller adipocytes than Dgat1$^{+/+}$ mice on both chow and high-fat diets (FIG. 1). Adipocytes from Dgat1$^{-/-}$ mice developed minimal hypertrophy in response to a high-fat diet, whereas those from Dgat1$^{+/+}$ mice doubled in size. This protection from diet-induced adipocyte hypertrophy in Dgat1$^{-/-}$ mice mirrored their weight response to a high-fat diet. In addition to having smaller adipocytes, male Dgat1$^{-/-}$ mice had a lower mean DNA content in reproductive fat pads than Dgat1$^{+/+}$ mice (169±36 versus 273±50 µg/fat pad, P<0.05), showing that Dgat1$^{-/-}$ mice also had fewer adipocytes.

Example IV

Increased Insulin Sensitivity in Dgat1$^{-/-}$ Mice

Figures 2A, 2B, 2C:
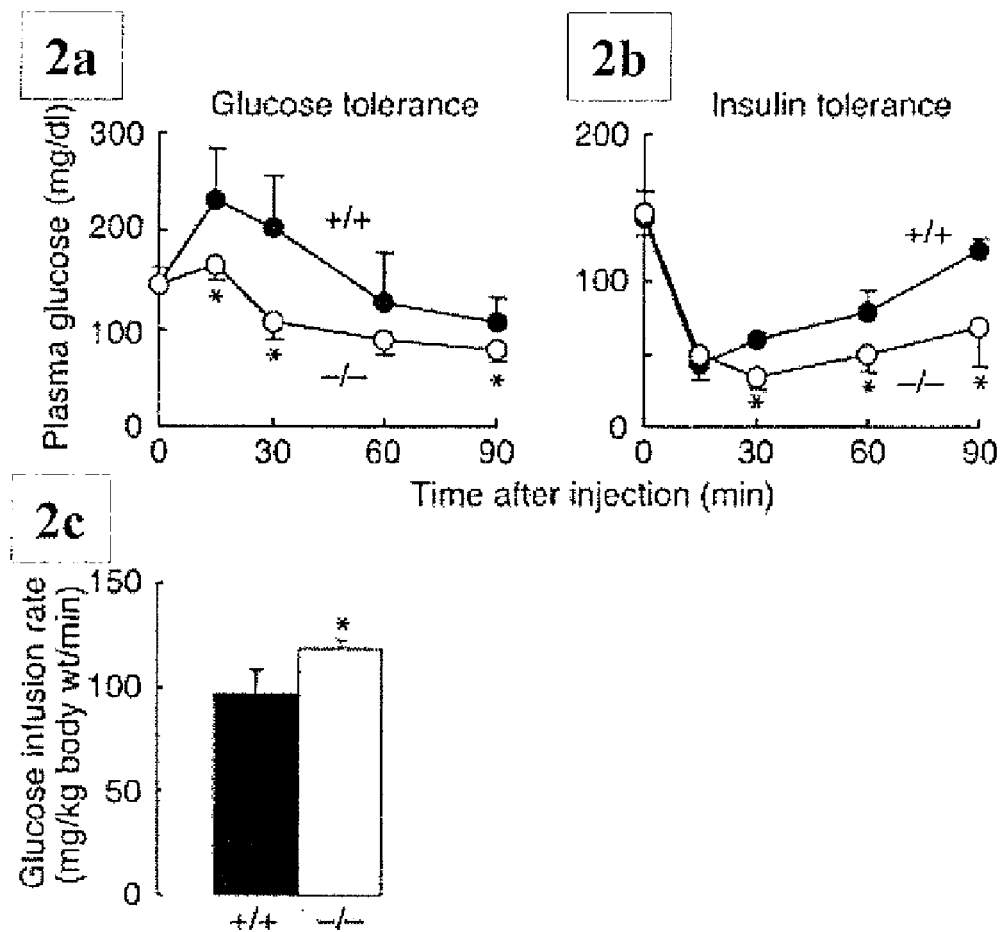
FIGS. 2a-2c are graphs showing increased insulin sensitivity in Dgat1$^{-/-}$ mice.

Glucose- and insulin-tolerance tests were performed. Dgat1$^{-/-}$ mice had lower plasma glucose concentrations than Dgat1$^{+/+}$ mice after a glucose load (FIG. 2a) or an insulin injection (FIG. 2b), showing that Dgat1$^{-/-}$ mice have increased insulin sensitivity. This was confirmed in hyperinsulinemic-euglycemic clamp studies, which showed that Dgat1$^{-/-}$ mice required an approximately 20% higher glucose infusion rate than Dgat1$^{+/+}$ mice to maintain euglycemia (FIG. 2c).

Example V

Increased Weight Loss in Response to Leptin Infusion in Dgat1$^{-/-}$ Mice

Figures 3A, 3B, 3C, 3D:
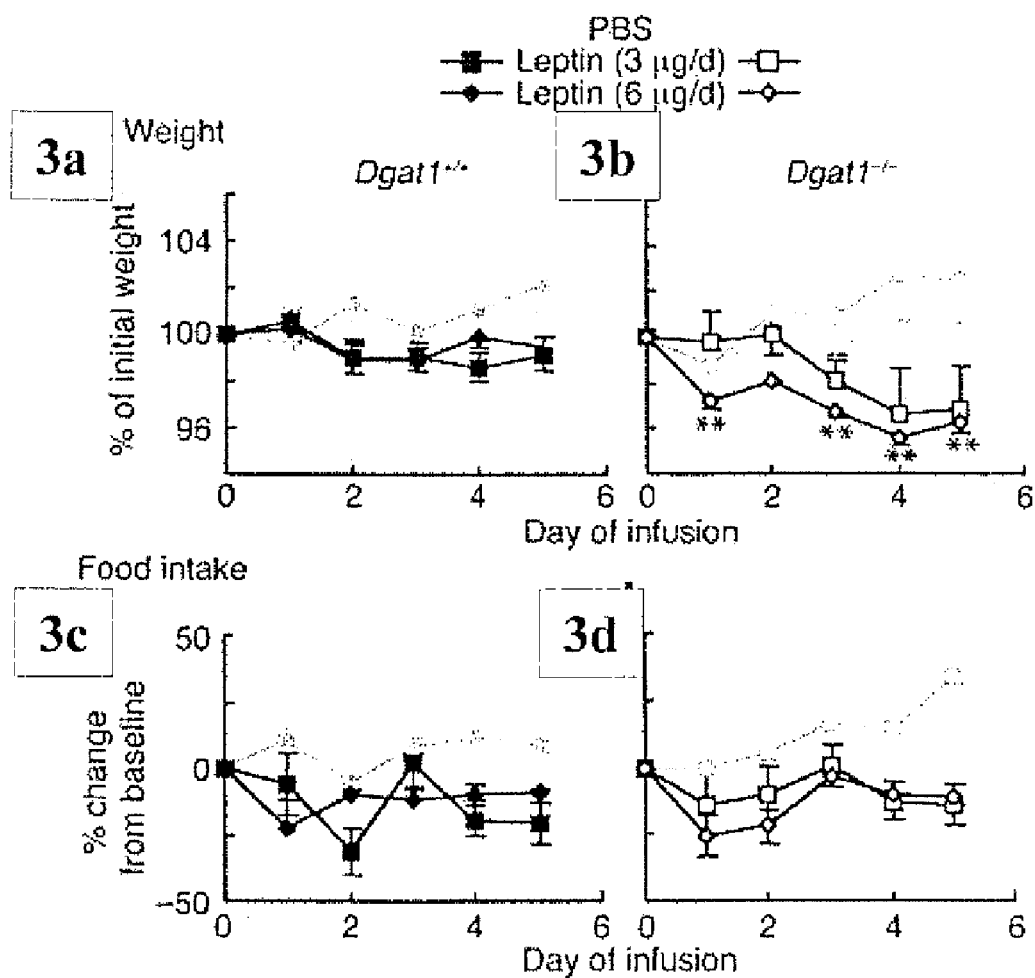
FIGS. 3a-3d are graphs showing increased weight loss in response to leptin infusion in Dgat1$^{-/-}$ mice.

Leptin was subcutaneously infused into Dgat1$^{+/+}$ mice and Dgat1$^{-/-}$ mice and measured their response in body weight and food intake. Leptin infusion achieved comparable levels of increase in plasma leptin levels in Dgat1$^{+/+}$ and Dgat1$^{-/-}$ (PBS-infused) mice (FIG. 3a). The same doses of leptin caused an additional 3% weight loss in age-matched Dgat1$^{-/-}$ mice (FIG. 3a), indicating all enhanced response to leptin.

Dgat1$^{-/-}$ mice consistently ate more than Dgat1$^{+/+}$ mice at baseline (25.3%±1.6% versus 19.5%±3.2% of body weight, P<0.05). During leptin infusion, Dgat1$^{-/-}$ mice continued to eat more than Dgat1$^{+/+}$ mice (19.8%±3% versus 15.8%±2.4% of body weight after 5 days of leptin (6 µg/day) infusion, P<0.05). Expressed as percentage of change from baseline, reduction in food intake in response to leptin infusion was comparable in Dgat1$^{-/-}$ and Dgat1$^{+/+}$ mice (FIGS. 3, c and d). Similarly, the absolute reduction in food intake per day was similar in Dgat1$^{+/+}$ and Dgat1$^{-/-}$ mice in response to leptin infusion in several different experiments (not shown). These results imply that the increased weight loss in leptin-treated Dgat1$^{-/-}$ mice resulted from increased energy expenditure rather than reduced food intake.

Example VI

Expression of Leptin-Regulated Genes in Dgat1$^{-/-}$ Mice

Figure 4:
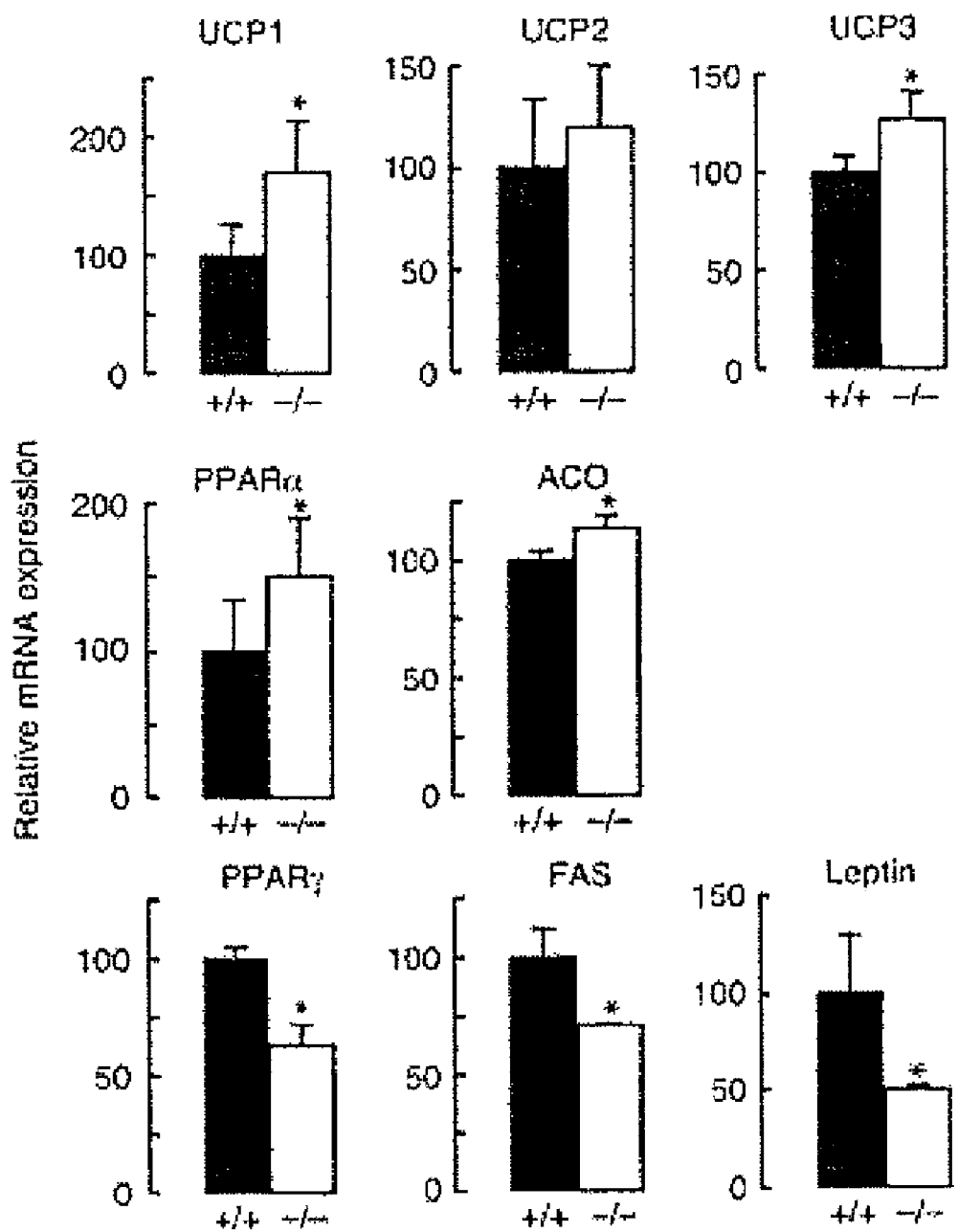
FIG. 4. is a panel of graphs showing expression of leptin-regulated genes in Dgat1$^{-/-}$ mice. The expression of UCP1 was examined in BAT. The expression of other genes was examined in WAT. For PPARα and leptin, results were obtained with real-time PCR. For other genes, results were obtained with Northern blotting. n=4-6 chow-fed male mice per genotype. *P<0.05 versus Dgat1$^{+/+}$ mice.

The expression of several leptin-regulated genes in BAT and WAT of Dgat1$^{-/-}$ mice was measured (FIG. 4). In Dgat1$^{-/-}$ BAT, UCP1 expression was increased by approximately 70% versus controls. In WAT, Dgat1$^{-/-}$ mice had increased levels of UCP3 expression, and UCP2 expression levels trended higher. The expression of genes involved in fatty acid oxidation (peroxisome proliferator-activated receptor α[PPARα] and acyl CoA oxidase) was also higher in Dgat1$^{-/-}$ WAT. In contrast, Dgat1$^{-/-}$ mice had decreased levels of expression for genes involved in adipogenesis (PPARγ) and lipid synthesis (fatty acid synthase) in WAT. Dgat1$^{-/-}$ mice also had an approximate 50% reduction in leptin (ob)

mRNA expression. These results show that Dgat1$^{-/-}$ mice have increased leptin sensitivity at baseline.

Example VII

Figures 5A, 5B, 5C, 5D, 5E, 5F, 5G, 5H, 5I, 5J:
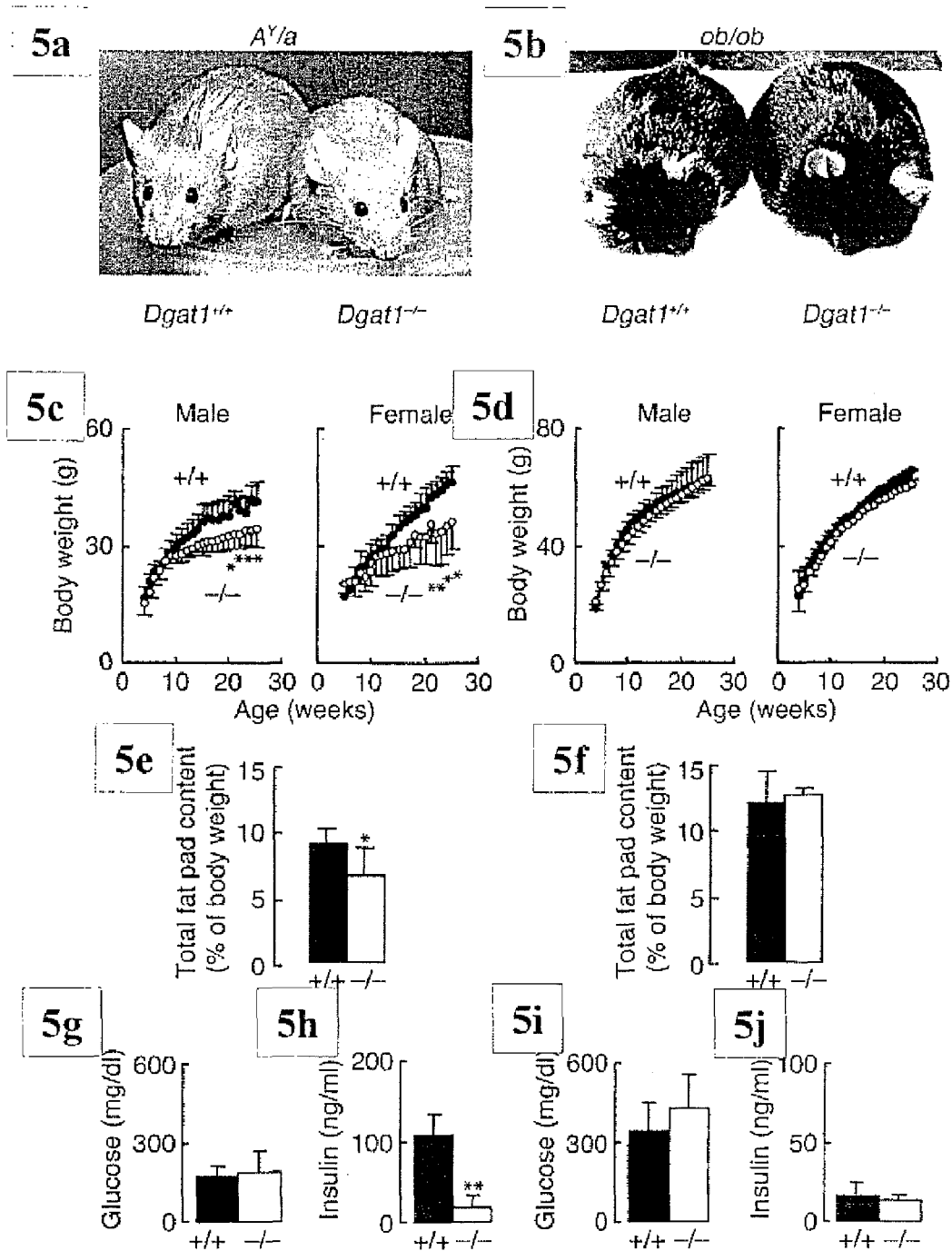
FIGS. 5a-5j are a series of figures showing the effects of DGAT1 deficiency on energy and glucose metabolism in Agouti yellow (A$^y$/a) and leptin-deficient (ob/ob) mice. n=8-12 mice per genotype for growth curves, n=5 chow-fed male mice per genotype for fat pad content, and n=4-6 chow-fed male mice per genotype for plasma glucose and insulin concentrations. *P<0.05, **P<0.01 versus Dgat1$^{+/+}$ mice.

DGAT1 Deficiency Protects Against Obesity and Insulin Resistance in A$^Y$/a Mice But Not in ob/ob Mice DGAT1 deficiency protects against obesity and insulin resistance induced by high-fat feeding. We introduced DGAT1 deficiency into A$^Y$/a and oh/oh mice through breeding. DGAT1 deficiency protected against obesity in A$^Y$/a mice (FIG. 5a), decreasing body weight (FIG. 5b) and fat pad content (FIG. 5c) by approximately 20% at 25 weeks. A$^Y$/a Dgat1$^{-/-}$ and A$^Y$/a Dgat1$^{+/+}$ mice had similar plasma glucose levels (FIG. 5d), but DGAT1 deficiency reduced plasma insulin levels by approximately 80% in A$^Y$/a mice (FIG. 5e), most likely by increasing their insulin sensitivity. In contrast, DGAT1 deficiency had no apparent effects in oh/ob mice. In the setting of leptin deficiency, both Dgat1$^{-/-}$ and Dgat1$^{+/+}$ mice became obese (FIG. 5f) and diabetic, with similar growth curves (FIG. 5g), fat pad content (FIG. 5h), and plasma glucose (FIG. 5i) and insulin (FIG. 5j) levels. DGAT1 deficiency also had no apparent effect on the obesity and diabetes of mice lacking functional leptin receptors (db/db mice, not shown).

Example VIII

Increased DGAT2 mRNA Expression in WAT of Leptin-Deficient Dgat1$^{-/-}$ Mice

Figure 6:
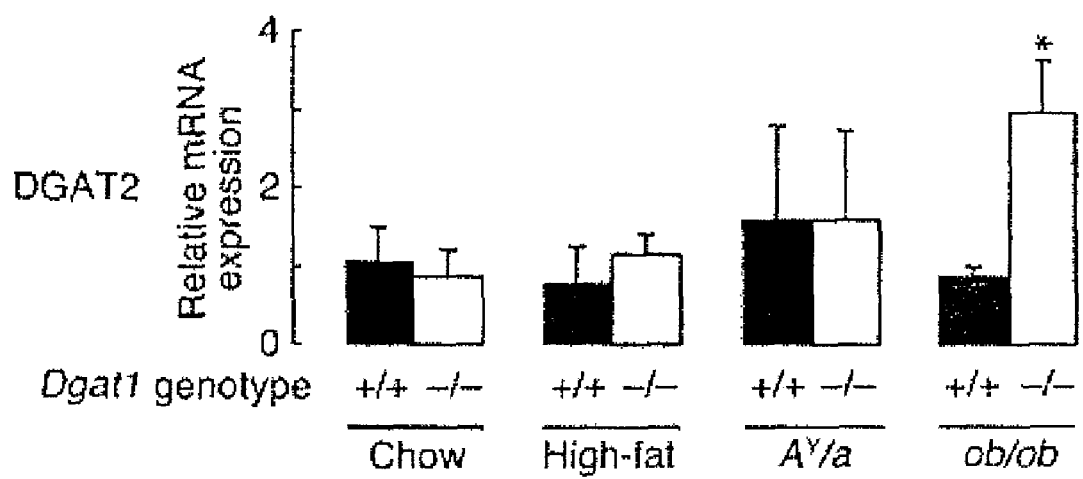
FIG. 6. is a graph showing increased DGAT2 mRNA expression in WAT of leptin-deficient Dgat1$^{-/-}$ mice. Results were obtained with real-time PCR. n=4-6 male mice per genotype. *P<0.05 versus oh/oh Dgat1$^{+/+}$ mice.

DGAT2 mRNA expression in WAT of Dgat1$^{-/-}$ mice in different backgrounds and conditions was measured (FIG. 6).

DGAT2 expression was not increased in Dgat1$^{-/-}$ mice at baseline (chow) or after 15 weeks of a high-fat diet. DGAT2 expression was also not increased in A$^Y$/a Dgat1$^{-/-}$ mice. In contrast, DGAT2 expression was elevated approximately threefold in leptin-deficient Dgat1$^{-/-}$ mice. This suggests that leptin normally downregulates DGAT2 expression in WAT and that the upregulation of DGAT2 expression may compensate for the loss of DGAT1 in leptin-deficient Dgat1$^{-/-}$ mice.

It is evident from the above results and discussion that the subject invention provides an important method for modulating sensitivity to insulin and/or leptin which method may be used for the treatment of diseases and conditions associated with altered sensitivity to leptin and/or insulin, e.g. conditions associated with abnormal carbohydrate metabolism such as diabetes and obesity. As such, the subject methods and systems find use in a variety of different applications, including research, industry, and medicine. Accordingly, the present invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A genetically modified mouse that comprises in its genome a homozygous insertion of a heterologous nucleic acid into the endogenous diacylglycerol acyltransferase-1 (DGAT-1) gene, resulting in a defect in the endogenous DGAT-1 gene, wherein the genetically modified mouse does not express DGAT-1 protein and wherein said genetically modified mouse has decreased DGAT activity levels and exhibits one or more of reduced triglyceride levels in white adipose tissue and skeletal muscle, smaller adipocytes, increased insulin sensitivity, and increased leptin sensitivity compared to a wild-type control mouse.

2. The genetically modified mouse according to claim 1, wherein the genetically modified mouse comprises an Agouti yellow ($A^y$/a) genotype.

3. A cell isolated from the genetically modified mouse of claim 1.

4. A method of screening a candidate agent for an activity that modulates sensitivity to insulin and/or leptin, said method comprising: (a) administering said candidate agent to a genetically modified mouse of claim 1; (b) determining insulin and/or leptin sensitivity in said genetically modified mouse administered the candidate agent and a genetically modified mouse of claim 1 that does not receive the candidate agent, wherein a difference in insulin and/or leptin sensitivity in the genetically modified mouse administered the candidate agent as compared to the genetically modified mouse that does not receive the candidate agent identifies the candidate agent as an agent that modulates insulin and/or leptin sensitivity.

5. The method of claim 4, wherein insulin and/or leptin sensitivity is determined by measuring one or more of blood glucose levels, glucose tolerance, and weight gain.

* * * * *

SEQUENCE LISTING

```
<160> NUMBER OF SEQ ID NOS: 35

<210> SEQ ID NO 1
<211> LENGTH: 1497
<212> TYPE: DNA
<213> ORGANISM: Mus musculus
<220> FEATURE:
<221> NAME/KEY: CDS
<222> LOCATION: (1)...(1497)
<223> OTHER INFORMATION: Mouse DGAT1 coding sequence

<400> SEQUENCE: 1 atg ggc gac cgc gga ggc gcg gga agc tct cgg cgt cgg agg acc ggc      48
Met Gly Asp Arg Gly Gly Ala Gly Ser Ser Arg Arg Arg Arg Thr Gly
1               5                   10                  15 tcg cgg gtt tcc gtc cag ggt ggt agt ggg ccc aag gta gaa gag gac      96
Ser Arg Val Ser Val Gln Gly Gly Ser Gly Pro Lys Val Glu Glu Asp
            20                  25                  30 gag gtg cga gac gcg gct gtg agc ccc gac ttg ggc gcc ggg ggt gac      144
Glu Val Arg Asp Ala Ala Val Ser Pro Asp Leu Gly Ala Gly Gly Asp
        35                  40                  45 gcg ccg gct ccg gct ccg gct cca gcc cat acc cgg gac aaa gac ggg      192
Ala Pro Ala Pro Ala Pro Ala Pro Ala His Thr Arg Asp Lys Asp Gly
    50                  55                  60 cgg acc agc gtg ggc gac ggc tac tgg gat ctg agg tgc cat cgt ctg      240
Arg Thr Ser Val Gly Asp Gly Tyr Trp Asp Leu Arg Cys His Arg Leu
65                  70                  75                  80
```

```
caa gat tct ttg ttc agc tca gac agt ggt ttc agc aat tat cgt ggt    288
Gln Asp Ser Leu Phe Ser Ser Asp Ser Gly Phe Ser Asn Tyr Arg Gly
             85                  90                  95 atc ctg aat tgg tgt gtg gtg atg ctg atc ctg agt aat gca agg tta    336
Ile Leu Asn Trp Cys Val Val Met Leu Ile Leu Ser Asn Ala Arg Leu
            100                 105                 110 ttt tta gag aac ctt atc aag tat ggc atc ctg gtg gat cct atc cag    384
Phe Leu Glu Asn Leu Ile Lys Tyr Gly Ile Leu Val Asp Pro Ile Gln
        115                 120                 125 gtg gtg tct ctg ttt ttg aag gac ccc tac agc tgg cct gcc cca tgc    432
Val Val Ser Leu Phe Leu Lys Asp Pro Tyr Ser Trp Pro Ala Pro Cys
130                 135                 140 gtg att att gca tcc aat att ttt gtt gtg gct gca ttt cag att gag    480
Val Ile Ile Ala Ser Asn Ile Phe Val Val Ala Ala Phe Gln Ile Glu
    145                 150                 155                 160 aag cgc ctg gca gtg ggt gcc ctg aca gag cag atg ggg ctg ctg cta    528
Lys Arg Leu Ala Val Gly Ala Leu Thr Glu Gln Met Gly Leu Leu Leu
                165                 170                 175 cat gtg gtt aac ctg gcc aca atc att tgc ttc cca gca gct gtg gcc    576
His Val Val Asn Leu Ala Thr Ile Ile Cys Phe Pro Ala Ala Val Ala
            180                 185                 190 tta ctg gtt gag tct atc act cca gtg ggt tcc gtg ttt gct ctg gca    624
Leu Leu Val Glu Ser Ile Thr Pro Val Gly Ser Val Phe Ala Leu Ala
        195                 200                 205 tca tac tcc atc atg ttc ctc aag ctt tat tcc tac cgg gat gtc aac    672
Ser Tyr Ser Ile Met Phe Leu Lys Leu Tyr Ser Tyr Arg Asp Val Asn
    210                 215                 220 ctg tgg tgc cgc cag cga agg gtc aag gcc aaa gct gtc tct aca ggg    720
Leu Trp Cys Arg Gln Arg Arg Val Lys Ala Lys Ala Val Ser Thr Gly
225                 230                 235                 240 aag aag gtc agt ggg gct gct gcc cag caa gct gtg agc tat cca gac    768
Lys Lys Val Ser Gly Ala Ala Ala Gln Gln Ala Val Ser Tyr Pro Asp
                245                 250                 255 aac ctg acc tac cga gat ctc tat tac ttc atc ttt gct cct act ttg    816
Asn Leu Thr Tyr Arg Asp Leu Tyr Tyr Phe Ile Phe Ala Pro Thr Leu
            260                 265                 270 tgt tat gaa ctc aac ttt cct cgg tcc ccc cga ata cga aag cgc ttt    864
Cys Tyr Glu Leu Asn Phe Pro Arg Ser Pro Arg Ile Arg Lys Arg Phe
        275                 280                 285 ctg cta cga cga gtt ctt gag atg ctc ttt ttt acc cag ctt caa gtg    912
Leu Leu Arg Arg Val Leu Glu Met Leu Phe Phe Thr Gln Leu Gln Val
    290                 295                 300 ggg ctg atc caa cag tgg atg gtc cct act atc cag aac tcc atg aag    960
Gly Leu Ile Gln Gln Trp Met Val Pro Thr Ile Gln Asn Ser Met Lys
305                 310                 315                 320 ccc ttc aag gat atg gac tat tca cgg atc att gag cgt ctc tta aag   1008
Pro Phe Lys Asp Met Asp Tyr Ser Arg Ile Ile Glu Arg Leu Leu Lys
                325                 330                 335 ctg gcg gtc ccc aac cat ctg atc tgg ctt atc ttc ttc tat tgg ttt   1056
Leu Ala Val Pro Asn His Leu Ile Trp Leu Ile Phe Phe Tyr Trp Phe
            340                 345                 350 ttc cac tcc tgt ctc aat gct gtg gca gag ctt ctg cag ttt gga gac   1104
Phe His Ser Cys Leu Asn Ala Val Ala Glu Leu Leu Gln Phe Gly Asp
        355                 360                 365 cgc gag ttc tac aga gat tgg tgg aat gct gag tct gtc acc tac ttt   1152
Arg Glu Phe Tyr Arg Asp Trp Trp Asn Ala Glu Ser Val Thr Tyr Phe
    370                 375                 380 tgg cag aac tgg aat atc ccc gtg cac aag tgg tgc atc aga cac ttc   1200
Trp Gln Asn Trp Asn Ile Pro Val His Lys Trp Cys Ile Arg His Phe
```

-continued

| | |
|---|---|
| tac aag cct atg ctc aga cat ggc agc agc aaa tgg gtg gcc agg aca<br>Tyr Lys Pro Met Leu Arg His Gly Ser Ser Lys Trp Val Ala Arg Thr<br>                                        405                          410                      415 | 1248 |
| gga gta ttt ttg acc tca gcc ttc ttc cat gag tac cta gtg agc gtt<br>Gly Val Phe Leu Thr Ser Ala Phe Phe His Glu Tyr Leu Val Ser Val<br>              420                          425                          430 | 1296 |
| ccc ctg cgg atg ttc cgc ctc tgg gca ttc aca gcc atg atg gct cag<br>Pro Leu Arg Met Phe Arg Leu Trp Ala Phe Thr Ala Met Met Ala Gln<br>                       435                          440                          445 | 1344 |
| gtc cca ctg gcc tgg att gtg ggc cga ttc ttc caa ggg aac tat ggc<br>Val Pro Leu Ala Trp Ile Val Gly Arg Phe Phe Gln Gly Asn Tyr Gly<br>         450                           455                          460 | 1392 |
| aat gca gct gtg tgg gtg aca ctc atc att ggg caa ccg gtg gct gtg<br>Asn Ala Ala Val Trp Val Thr Leu Ile Ile Gly Gln Pro Val Ala Val<br>465                        470                          475                          480 | 1440 |
| ctc atg tat gtc cac gac tac tac gtg ctc aac tac gat gcc cca gtg<br>Leu Met Tyr Val His Asp Tyr Tyr Val Leu Asn Tyr Asp Ala Pro Val<br>                       485                          490                          495 | 1488 |
| ggg gta tga<br>Gly Val  * | 1497 |

<210> SEQ ID NO 2
<211> LENGTH: 1467
<212> TYPE: DNA
<213> ORGANISM: Homo sapiens
<220> FEATURE:
<221> NAME/KEY: CDS
<222> LOCATION: (1)...(1467)
<223> OTHER INFORMATION: Homo sapiens diacylglycerol O-acyltransferase homolog 1

<400> SEQUENCE: 2

| | |
|---|---|
| atg ggc gac cgc ggc agc tcc cgg cgc cgg agg aca ggg tcg cgg ccc<br>Met Gly Asp Arg Gly Ser Ser Arg Arg Arg Thr Gly Ser Arg Pro<br>1                 5                       10                      15 | 48 |
| tcg agc cac ggc ggc ggc ggg cct gcg gcg gcg gaa gag gag gtg cgg<br>Ser Ser His Gly Gly Gly Gly Pro Ala Ala Ala Glu Glu Glu Val Arg<br>               20                       25                       30 | 96 |
| gac gcc gct gcg ggc ccc gac gtg gga gcc gcg ggg gac gcg cca gcc<br>Asp Ala Ala Ala Gly Pro Asp Val Gly Ala Ala Gly Asp Ala Pro Ala<br>              35                       40                       45 | 144 |
| ccg gcc ccc aac aag gac gga gac gcc ggc gtg ggc agc ggc cac tgg<br>Pro Ala Pro Asn Lys Asp Gly Asp Ala Gly Val Gly Ser Gly His Trp<br>         50                           55                          60 | 192 |
| gag ctg agg tgc cat cgc ctg cag gat tct tta ttc agc tct gac agt<br>Glu Leu Arg Cys His Arg Leu Gln Asp Ser Leu Phe Ser Ser Asp Ser<br>65                        70                          75                          80 | 240 |
| ggc ttc agc aac tac cgt ggc atc ctg aac tgg tgt gtg gtg atg ctg<br>Gly Phe Ser Asn Tyr Arg Gly Ile Leu Asn Trp Cys Val Val Met Leu<br>                      85                       90                       95 | 288 |
| atc ttg agc aat gcc cgg tta ttt ctg gag aac ctc atc aag tat ggc<br>Ile Leu Ser Asn Ala Arg Leu Phe Leu Glu Asn Leu Ile Lys Tyr Gly<br>               100                      105                      110 | 336 |
| atc ctg gtg gac ccc atc cag gtg gtt tct ctg ttc ctg aag gat ccc<br>Ile Leu Val Asp Pro Ile Gln Val Val Ser Leu Phe Leu Lys Asp Pro<br>             115                       120                      125 | 384 |
| tat agc tgg ccc gcc cca tgc ctg gtt att gcg gcc aat gtc ttt gct<br>Tyr Ser Trp Pro Ala Pro Cys Leu Val Ile Ala Ala Asn Val Phe Ala<br>         130                          135                          140 | 432 |
| gtg gct gca ttc cag gtt gag aag cgc ctg gcg gtg ggt gcc ctg acg | 480 |

-continued

```
        Val Ala Ala Phe Gln Val Glu Lys Arg Leu Ala Val Gly Ala Leu Thr
        145                 150                 155                 160 gag cag gcg gga ctg ctg ctg cac gtg gcc aac ctg gcc acc att ctg         528
Glu Gln Ala Gly Leu Leu Leu His Val Ala Asn Leu Ala Thr Ile Leu
                165                 170                 175 tgt ttc cca gcg gct gtg gtc tta ctg gtt gag tct atc act cca gtg         576
Cys Phe Pro Ala Ala Val Val Leu Leu Val Glu Ser Ile Thr Pro Val
                180                 185                 190 ggc tcc ctg ctg gcg ctg atg gcg cac acc atc ctc ttc ctc aag ctc         624
Gly Ser Leu Leu Ala Leu Met Ala His Thr Ile Leu Phe Leu Lys Leu
                195                 200                 205 ttc tcc tac cgc gac gtc aac tca tgg tgc cgc agg gcc agg gcc aag         672
Phe Ser Tyr Arg Asp Val Asn Ser Trp Cys Arg Arg Ala Arg Ala Lys
                210                 215                 220 gct gcc tct gca ggg aag aag gcc agc agt gct gct gcc ccg cac acc         720
Ala Ala Ser Ala Gly Lys Lys Ala Ser Ser Ala Ala Ala Pro His Thr
225                 230                 235                 240 gtg agc tac ccg gac aat ctg acc tac cgc gat ctc tac tac ttc ctc         768
Val Ser Tyr Pro Asp Asn Leu Thr Tyr Arg Asp Leu Tyr Tyr Phe Leu
                245                 250                 255 ttc gcc ccc acc ttg tgc tac gag ctc aac ttt ccc cgc tct ccc cgc         816
Phe Ala Pro Thr Leu Cys Tyr Glu Leu Asn Phe Pro Arg Ser Pro Arg
                260                 265                 270 atc cgg aag cgc ttt ctg ctg cga cgg atc ctt gag atg ctg ttc ttc         864
Ile Arg Lys Arg Phe Leu Leu Arg Arg Ile Leu Glu Met Leu Phe Phe
                275                 280                 285 acc cag ctc cag gtg ggg ctg atc cag cag tgg atg gtc ccc acc atc         912
Thr Gln Leu Gln Val Gly Leu Ile Gln Gln Trp Met Val Pro Thr Ile
                290                 295                 300 cag aac tcc atg aag ccc ttc aag gac atg gac tac tca cgc atc atc         960
Gln Asn Ser Met Lys Pro Phe Lys Asp Met Asp Tyr Ser Arg Ile Ile
305                 310                 315                 320 gag cgc ctc ctg aag ctg gcg gtc ccc aat cac ctc atc tgg ctc atc        1008
Glu Arg Leu Leu Lys Leu Ala Val Pro Asn His Leu Ile Trp Leu Ile
                325                 330                 335 ttc ttc tac tgg ctc ttc cac tcc tgc ctg aat gcc gtg gct gag ctc        1056
Phe Phe Tyr Trp Leu Phe His Ser Cys Leu Asn Ala Val Ala Glu Leu
                340                 345                 350 atg cag ttt gga gac cgg gag ttc tac cgg gac tgg tgg aac tcc gag        1104
Met Gln Phe Gly Asp Arg Glu Phe Tyr Arg Asp Trp Trp Asn Ser Glu
                355                 360                 365 tct gtc acc tac ttc tgg cag aac tgg aac atc cct gtg cac aag tgg        1152
Ser Val Thr Tyr Phe Trp Gln Asn Trp Asn Ile Pro Val His Lys Trp
                370                 375                 380 tgc atc aga cac ttc tac aag ccc atg ctt cga cgg ggc agc agc aag        1200
Cys Ile Arg His Phe Tyr Lys Pro Met Leu Arg Arg Gly Ser Ser Lys
385                 390                 395                 400 tgg atg gcc agg aca ggg gtg ttc ctg gcc tcg gcc ttc ttc cac gag        1248
Trp Met Ala Arg Thr Gly Val Phe Leu Ala Ser Ala Phe Phe His Glu
                405                 410                 415 tac ctg gtg agc gtc cct ctg cga atg ttc cgc ctc tgg gcg ttc acg        1296
Tyr Leu Val Ser Val Pro Leu Arg Met Phe Arg Leu Trp Ala Phe Thr
                420                 425                 430 ggc atg atg gct cag atc cca ctg gcc tgg ttc gtg ggc cgc ttt ttc        1344
Gly Met Met Ala Gln Ile Pro Leu Ala Trp Phe Val Gly Arg Phe Phe
                435                 440                 445 cag ggc aac tat ggc aac gca gct gtg tgg ctg tcg ctc atc atc gga        1392
Gln Gly Asn Tyr Gly Asn Ala Ala Val Trp Leu Ser Leu Ile Ile Gly
450                 455                 460
```

```
cag cca ata gcc gtc ctc atg tac gtc cac gac tac tac gtg ctc aac      1440
Gln Pro Ile Ala Val Leu Met Tyr Val His Asp Tyr Tyr Val Leu Asn
465                 470                 475                 480 tat gag gcc cca gcg gca gag gcc tga                                  1467
Tyr Glu Ala Pro Ala Ala Glu Ala *
                485

<210> SEQ ID NO 3
<211> LENGTH: 1497
<212> TYPE: DNA
<213> ORGANISM: Rattus norvegicus
<220> FEATURE:
<221> NAME/KEY: CDS
<222> LOCATION: (1)...(1497)
<223> OTHER INFORMATION: s norvegicus diacylglycerol O-acyltransferase 1
      coding sequence

<400> SEQUENCE: 3 atg ggc gac cgc gga ggc gcg gga agc tct cgg cgt cgc agg acc ggc        48
Met Gly Asp Arg Gly Gly Ala Gly Ser Ser Arg Arg Arg Arg Thr Gly
1               5                   10                  15 tcg cgg gtt tcc gtc cag gga ggt agt ggg ccc aag gta gaa gag gac        96
Ser Arg Val Ser Val Gln Gly Gly Ser Gly Pro Lys Val Glu Glu Asp
            20                  25                  30 gag gtg cga gaa gcg gct gtg agc ccc gac ttg ggc gcc ggg ggt gac       144
Glu Val Arg Glu Ala Ala Val Ser Pro Asp Leu Gly Ala Gly Gly Asp
        35                  40                  45 gcg ccg gct ccg gct ccg gct cca gcc cat acc cgg gac aaa gac cgg       192
Ala Pro Ala Pro Ala Pro Ala Pro Ala His Thr Arg Asp Lys Asp Arg
    50                  55                  60 cag acc agc gtg ggc gac ggc cac tgg gag ctg agg tgc cat cgt ctg       240
Gln Thr Ser Val Gly Asp Gly His Trp Glu Leu Arg Cys His Arg Leu
65                  70                  75                  80 caa gac tct ttg ttc agc tca gac agc ggt ttc agc aat tac cgt ggt       288
Gln Asp Ser Leu Phe Ser Ser Asp Ser Gly Phe Ser Asn Tyr Arg Gly
                85                  90                  95 atc ctg aat tgg tgc gtg gtg atg ctg atc ctg agt aat gca agg tta       336
Ile Leu Asn Trp Cys Val Val Met Leu Ile Leu Ser Asn Ala Arg Leu
            100                 105                 110 tct tta gag aat ctt atc aag tat ggc atc ctg gtg gat ccc atc cag       384
Ser Leu Glu Asn Leu Ile Lys Tyr Gly Ile Leu Val Asp Pro Ile Gln
        115                 120                 125 gtg gtg tct ctg ttt ctg aag gac ccc tac agc tgg cct gcc cca tgc       432
Val Val Ser Leu Phe Leu Lys Asp Pro Tyr Ser Trp Pro Ala Pro Cys
    130                 135                 140 ttg atc att gca tcc aat atc ttt att gtg gct aca ttt cag att gag       480
Leu Ile Ile Ala Ser Asn Ile Phe Ile Val Ala Thr Phe Gln Ile Glu
145                 150                 155                 160 aag cgc ctg tca gtg ggt gcc ctg aca gag cag atg ggg ctg ctg cta       528
Lys Arg Leu Ser Val Gly Ala Leu Thr Glu Gln Met Gly Leu Leu Leu
                165                 170                 175 cat gtg gtt aac ctg gcc aca att atc tgc ttc cca gca gct gtg gcc       576
His Val Val Asn Leu Ala Thr Ile Ile Cys Phe Pro Ala Ala Val Ala
            180                 185                 190 tta ctg gtt gag tct atc act cca gtg ggt tcc ctg ttt gct ctg gca       624
Leu Leu Val Glu Ser Ile Thr Pro Val Gly Ser Leu Phe Ala Leu Ala
        195                 200                 205 tca tac tcc atc atc ttc ctc aag ctt tct tcc tac cgg gat gtc aat       672
Ser Tyr Ser Ile Ile Phe Leu Lys Leu Ser Ser Tyr Arg Asp Val Asn
    210                 215                 220 ctg tgg tgc cgc cag cga agg gtc aag gcc aaa gct gtg tct gca ggg       720
Leu Trp Cys Arg Gln Arg Arg Val Lys Ala Lys Ala Val Ser Ala Gly
```

```
                225                 230                 235                 240 aag aag gtc agt ggg gct gct gcc cag aac act gta agc tat ccg gac        768
Lys Lys Val Ser Gly Ala Ala Ala Gln Asn Thr Val Ser Tyr Pro Asp
            245                 250                 255 aac ctg acc tac cga gat ctc tat tac ttc atc ttt gct cct act ttg        816
Asn Leu Thr Tyr Arg Asp Leu Tyr Tyr Phe Ile Phe Ala Pro Thr Leu
            260                 265                 270 tgt tat gaa ctc aac ttt cct cga tcc ccc cga ata cga aag cgc ttt        864
Cys Tyr Glu Leu Asn Phe Pro Arg Ser Pro Arg Ile Arg Lys Arg Phe
        275                 280                 285 ctg cta cgg cgg gtt ctt gag atg ctc ttt ttc acc cag ctt caa gtg        912
Leu Leu Arg Arg Val Leu Glu Met Leu Phe Phe Thr Gln Leu Gln Val
        290                 295                 300 ggg ctg atc cag cag tgg atg gtc cct act atc cag aac tcc atg aag        960
Gly Leu Ile Gln Gln Trp Met Val Pro Thr Ile Gln Asn Ser Met Lys
305                 310                 315                 320 ccc ttc aag gac atg gac tat tca cga atc att gag cgt ctc tta aag       1008
Pro Phe Lys Asp Met Asp Tyr Ser Arg Ile Ile Glu Arg Leu Leu Lys
                325                 330                 335 ctg gcg gtc ccc aac cat ctg ata tgg ctc atc ttc ttc tat tgg ctt       1056
Leu Ala Val Pro Asn His Leu Ile Trp Leu Ile Phe Phe Tyr Trp Leu
                340                 345                 350 ttc cac tca tgt ctc aat gct gtg gca gag ctc ctg cag ttt gga gac       1104
Phe His Ser Cys Leu Asn Ala Val Ala Glu Leu Leu Gln Phe Gly Asp
            355                 360                 365 cgc gag ttc tac agg gac tgg tgg aat gct gag tct gtc acc tac ttt       1152
Arg Glu Phe Tyr Arg Asp Trp Trp Asn Ala Glu Ser Val Thr Tyr Phe
        370                 375                 380 tgg cag aac tgg aat atc ccc gtg cac aag tgg tgc atc aga cac ttt       1200
Trp Gln Asn Trp Asn Ile Pro Val His Lys Trp Cys Ile Arg His Phe
385                 390                 395                 400 tac aag cct atg ctc aga ctg ggc agc aac aaa tgg atg gcc agg act       1248
Tyr Lys Pro Met Leu Arg Leu Gly Ser Asn Lys Trp Met Ala Arg Thr
                405                 410                 415 ggg gtc ttt tgg gcg tca gct ttc ttt cat gag tac cta gtg agc att       1296
Gly Val Phe Trp Ala Ser Ala Phe Phe His Glu Tyr Leu Val Ser Ile
                420                 425                 430 ccc ctg agg atg ttc cgc ctt tgg gca ttc aca gca atg atg gct cag       1344
Pro Leu Arg Met Phe Arg Leu Trp Ala Phe Thr Ala Met Met Ala Gln
            435                 440                 445 gtc cca ctg gcc tgg att gtg aac cgc ttc ttc caa ggg aac tat ggc       1392
Val Pro Leu Ala Trp Ile Val Asn Arg Phe Phe Gln Gly Asn Tyr Gly
        450                 455                 460 aat gca gct gtg tgg gtg aca ctc atc att ggg caa ccg gtg gct gtg       1440
Asn Ala Ala Val Trp Val Thr Leu Ile Ile Gly Gln Pro Val Ala Val
465                 470                 475                 480 ctc atg tat gtc cac gac tac tac gtg ctc aac tat gat gcc cca gtg       1488
Leu Met Tyr Val His Asp Tyr Tyr Val Leu Asn Tyr Asp Ala Pro Val
                485                 490                 495 ggg gca tga                                                           1497
Gly Ala *

<210> SEQ ID NO 4
<211> LENGTH: 1470
<212> TYPE: DNA
<213> ORGANISM: Bos taurus
<220> FEATURE:
<221> NAME/KEY: CDS
<222> LOCATION: (1)...(1470)
<223> OTHER INFORMATION: Bos taurus dgat coding sequence
```

-continued

```
<400> SEQUENCE: 4 atg ggc gac cgc ggc ggc gcg ggc ggc tcc cgg cgc cgg agg acg ggg      48
Met Gly Asp Arg Gly Gly Ala Gly Gly Ser Arg Arg Arg Arg Thr Gly
1               5                   10                  15 tcg cgg cct tcg atc cag ggc ggc agt ggg ccc gcg gca gcg gaa gag      96
Ser Arg Pro Ser Ile Gln Gly Gly Ser Gly Pro Ala Ala Ala Glu Glu
            20                  25                  30 gag gtg cgg gat gtg ggc gcc gga ggg gac gcg ccg gtc cgg gac aca     144
Glu Val Arg Asp Val Gly Ala Gly Gly Asp Ala Pro Val Arg Asp Thr
        35                  40                  45 gac aag gac gga gac gta gac gtg ggc agc ggc cac tgg gac ctg agg     192
Asp Lys Asp Gly Asp Val Asp Val Gly Ser Gly His Trp Asp Leu Arg
    50                  55                  60 tgt cac cgc ctg cag gat tcc ctg ttc agt tct gac agt ggc ttc agc     240
Cys His Arg Leu Gln Asp Ser Leu Phe Ser Ser Asp Ser Gly Phe Ser
65                  70                  75                  80 aac tac cgt ggc atc ctg aat tgg tgt gtg gtg atg ctg atc tta agc     288
Asn Tyr Arg Gly Ile Leu Asn Trp Cys Val Val Met Leu Ile Leu Ser
                85                  90                  95 aac gca cgg tta ttt cta gag aac ctc atc aag tat ggc atc ctg gtg     336
Asn Ala Arg Leu Phe Leu Glu Asn Leu Ile Lys Tyr Gly Ile Leu Val
            100                 105                 110 gac ccc atc cag gtg gtg tct ctg ttc ctg aag gac ccc tac agc tgg     384
Asp Pro Ile Gln Val Val Ser Leu Phe Leu Lys Asp Pro Tyr Ser Trp
        115                 120                 125 cca gct ctg tgc ctg gtc att gtg gcc aat atc ttt gcc gtg gct gcg     432
Pro Ala Leu Cys Leu Val Ile Val Ala Asn Ile Phe Ala Val Ala Ala
    130                 135                 140 ttc cag gtg gag aag cgc ctg gcc gtg gga gct ctg acg gag cag gcg     480
Phe Gln Val Glu Lys Arg Leu Ala Val Gly Ala Leu Thr Glu Gln Ala
145                 150                 155                 160 ggg ctg ctg ctg cac ggg gtc aac ctg gcc acc att ctc tgc ttc cca     528
Gly Leu Leu Leu His Gly Val Asn Leu Ala Thr Ile Leu Cys Phe Pro
                165                 170                 175 gcg gcc gtg gcc ttt ctc ctc gag tct atc act cca gtg ggc tcc gtg     576
Ala Ala Val Ala Phe Leu Leu Glu Ser Ile Thr Pro Val Gly Ser Val
            180                 185                 190 ctg gcc ctg atg gtc tac acc atc ctc ttc ctc aag ctg ttc tcc tac     624
Leu Ala Leu Met Val Tyr Thr Ile Leu Phe Leu Lys Leu Phe Ser Tyr
        195                 200                 205 cgg gac gtc aac ctc tgg tgc cga gag cgc agg gct ggg gcc aag gcc     672
Arg Asp Val Asn Leu Trp Cys Arg Glu Arg Arg Ala Gly Ala Lys Ala
    210                 215                 220 aag gct gct ttg gca ggt aag gcg gcc aac ggg gga gct gcc cag cgc     720
Lys Ala Ala Leu Ala Gly Lys Ala Ala Asn Gly Gly Ala Ala Gln Arg
225                 230                 235                 240 acc gtg agc tac ccc gac aac ctg acc tac cgc gat ctc tac tac ttc     768
Thr Val Ser Tyr Pro Asp Asn Leu Thr Tyr Arg Asp Leu Tyr Tyr Phe
                245                 250                 255 ctc ttc gcc ccc acc ctg tgc tac gag ctc aac ttc ccc cgc tcc ccc     816
Leu Phe Ala Pro Thr Leu Cys Tyr Glu Leu Asn Phe Pro Arg Ser Pro
            260                 265                 270 cgc atc cga aag cgc ttc ctg ctg cgg cga ctc ctg gag atg ctg ttc     864
Arg Ile Arg Lys Arg Phe Leu Leu Arg Arg Leu Leu Glu Met Leu Phe
        275                 280                 285 ctc acc cag ctc cag gtg ggg ctg atc cag cag tgg atg gtc ccg gcc     912
Leu Thr Gln Leu Gln Val Gly Leu Ile Gln Gln Trp Met Val Pro Ala
    290                 295                 300 atc cag aac tcc atg aag ccc ttc aag gac atg gac tac tcc cgc atc     960
Ile Gln Asn Ser Met Lys Pro Phe Lys Asp Met Asp Tyr Ser Arg Ile
```

-continued

```
Ile Gln Asn Ser Met Lys Pro Phe Lys Asp Met Asp Tyr Ser Arg Ile
305                 310                 315                 320 gtg gag cgc ctc ctg aag ctg gcg gtc ccc aac cac ctc atc tgg ctc         1008
Val Glu Arg Leu Leu Lys Leu Ala Val Pro Asn His Leu Ile Trp Leu
            325                 330                 335 atc ttc ttc tac tgg ctc ttc cac tcc tgc ctg aac gcc gtg gct gag         1056
Ile Phe Phe Tyr Trp Leu Phe His Ser Cys Leu Asn Ala Val Ala Glu
        340                 345                 350 ctc atg cag ttt gga gac cgc gag ttc tac cgg gac tgg tgg aac tcc         1104
Leu Met Gln Phe Gly Asp Arg Glu Phe Tyr Arg Asp Trp Trp Asn Ser
    355                 360                 365 gag tcc atc acc tac ttc tgg cag aac tgg aac atc cct gtt cac aag         1152
Glu Ser Ile Thr Tyr Phe Trp Gln Asn Trp Asn Ile Pro Val His Lys
370                 375                 380 tgg tgc atc aga cac ttc tac aag ccc atg ctc cgg cgg ggc agc agc         1200
Trp Cys Ile Arg His Phe Tyr Lys Pro Met Leu Arg Arg Gly Ser Ser
385                 390                 395                 400 aag tgg gca gcc agg acg gca gtg ttt ctg gcc tcc gcc ttc ttc cac         1248
Lys Trp Ala Ala Arg Thr Ala Val Phe Leu Ala Ser Ala Phe Phe His
            405                 410                 415 gag tac ctg gtg agc atc ccc ctg gga atg ttc cgc ctc tgg gcc ttc         1296
Glu Tyr Leu Val Ser Ile Pro Leu Gly Met Phe Arg Leu Trp Ala Phe
        420                 425                 430 acc ggc atg atg gcg cag atc ccg ctg gcc tgg ata gtg ggc cgc ttc         1344
Thr Gly Met Met Ala Gln Ile Pro Leu Ala Trp Ile Val Gly Arg Phe
    435                 440                 445 ttc cgc ggc aac tac ggc aac gcg gcc gtg tgg ctg tca ctc atc atc         1392
Phe Arg Gly Asn Tyr Gly Asn Ala Ala Val Trp Leu Ser Leu Ile Ile
450                 455                 460 ggg cag ccg gtg gcc gtc ctg atg tac gtc cac gac tac tac gtg ctc         1440
Gly Gln Pro Val Ala Val Leu Met Tyr Val His Asp Tyr Tyr Val Leu
465                 470                 475                 480 aac cgt gag gcg ccg gca gcc ggc acc tga                                 1470
Asn Arg Glu Ala Pro Ala Ala Gly Thr *
            485

<210> SEQ ID NO 5
<211> LENGTH: 1497
<212> TYPE: DNA
<213> ORGANISM: Caenorhabditis elegans
<220> FEATURE:
<221> NAME/KEY: CDS
<222> LOCATION: (1)...(1497)
<223> OTHER INFORMATION: Caenorhabditis elegans diacylglycerol
      acyltransferase coding sequence

<400> SEQUENCE: 5 atg caa atg cgt caa caa acg gga cga cgg cgg cgt cag cct tcg gaa         48
Met Gln Met Arg Gln Gln Thr Gly Arg Arg Arg Arg Gln Pro Ser Glu
1               5                   10                  15 aca tct aat ggt tct ttg gct tcc agt aga cgc tcc tca ttt gca caa         96
Thr Ser Asn Gly Ser Leu Ala Ser Ser Arg Arg Ser Ser Phe Ala Gln
            20                  25                  30 aat ggt aat tcg tca agg aaa agt tca gaa atg aga ggg cct tgc gag         144
Asn Gly Asn Ser Ser Arg Lys Ser Ser Glu Met Arg Gly Pro Cys Glu
        35                  40                  45 aaa gtg gta cat act gct caa gat tca ttg ttt tcg acg agt tct gga         192
Lys Val Val His Thr Ala Gln Asp Ser Leu Phe Ser Thr Ser Ser Gly
    50                  55                  60 tgg aca aat ttc cgt gga ttc ttc aat ttg tct att tta ctt ttg gta         240
Trp Thr Asn Phe Arg Gly Phe Phe Asn Leu Ser Ile Leu Leu Leu Val
65                  70                  75                  80
```

```
ctt tca aat gga cgc gtg gca ctt gaa aat gtg atc aaa tat ggt att      288
Leu Ser Asn Gly Arg Val Ala Leu Glu Asn Val Ile Lys Tyr Gly Ile
            85                  90                  95 ttg ata aca ccc ctt cag tgg atc tca acg ttt gtt gag cat cac tac      336
Leu Ile Thr Pro Leu Gln Trp Ile Ser Thr Phe Val Glu His His Tyr
        100                 105                 110 tca att tgg agc tgg cca aat ctt gct ctc atc cta tgc tca aat att      384
Ser Ile Trp Ser Trp Pro Asn Leu Ala Leu Ile Leu Cys Ser Asn Ile
            115                 120                 125 cag att ctc tcg gtt ttt gga atg gaa aaa att ctt gaa cgt gga tgg      432
Gln Ile Leu Ser Val Phe Gly Met Glu Lys Ile Leu Glu Arg Gly Trp
130                 135                 140 ctt gga aac gga ttc gct gca gtg ttc tac acc tcg ctt gtg att gca      480
Leu Gly Asn Gly Phe Ala Ala Val Phe Tyr Thr Ser Leu Val Ile Ala
145                 150                 155                 160 cat ctg aca att cca gtt gtg gtc act ctt acc cac aaa tgg aag aat      528
His Leu Thr Ile Pro Val Val Val Thr Leu Thr His Lys Trp Lys Asn
                165                 170                 175 cct ttg tgg tca gtc gta atg atg ggt gtt tat gtt att gaa gct ctc      576
Pro Leu Trp Ser Val Val Met Met Gly Val Tyr Val Ile Glu Ala Leu
            180                 185                 190 aaa ttc atc tca tat ggc cac gtc aac tac tgg gct cgt gat gct cgg      624
Lys Phe Ile Ser Tyr Gly His Val Asn Tyr Trp Ala Arg Asp Ala Arg
        195                 200                 205 cga aaa atc aca gag ctc aaa aca caa gtc acc gat ttg gca aag aaa      672
Arg Lys Ile Thr Glu Leu Lys Thr Gln Val Thr Asp Leu Ala Lys Lys
    210                 215                 220 aca tgt gat ccg aaa caa ttt tgg gat ttg aaa gat gaa tta tca atg      720
Thr Cys Asp Pro Lys Gln Phe Trp Asp Leu Lys Asp Glu Leu Ser Met
225                 230                 235                 240 cat cag atg gct gct caa tat cct gcc aat ttg aca ctt tcc aat atc      768
His Gln Met Ala Ala Gln Tyr Pro Ala Asn Leu Thr Leu Ser Asn Ile
                245                 250                 255 tac tac ttc atg gct gca cca aca ttg tgc tac gaa ttc aaa ttt cca      816
Tyr Tyr Phe Met Ala Ala Pro Thr Leu Cys Tyr Glu Phe Lys Phe Pro
            260                 265                 270 aga ttg ttg cga att cgg aag cac ttt ttg att aaa aga acc gtg gag      864
Arg Leu Leu Arg Ile Arg Lys His Phe Leu Ile Lys Arg Thr Val Glu
        275                 280                 285 ctt atc ttt cta tcg ttt ttg ata gct gca ctt gtt caa caa tgg gtt      912
Leu Ile Phe Leu Ser Phe Leu Ile Ala Ala Leu Val Gln Gln Trp Val
    290                 295                 300 gtt ccg act gtc cga aat agt atg aaa cct tta agt gaa atg gaa tac      960
Val Pro Thr Val Arg Asn Ser Met Lys Pro Leu Ser Glu Met Glu Tyr
305                 310                 315                 320 tct aga tgt ttg gaa cga ctc ttg aaa ctt gca att cca aat cat ctc     1008
Ser Arg Cys Leu Glu Arg Leu Leu Lys Leu Ala Ile Pro Asn His Leu
                325                 330                 335 atc tgg ctt cta ttc ttc tac aca ttc ttc cat tca ttt ttg aac ttg     1056
Ile Trp Leu Leu Phe Phe Tyr Thr Phe Phe His Ser Phe Leu Asn Leu
            340                 345                 350 atc gcc gag ctg ctt cga ttt gcc gat cgt gag ttc tac aga gac ttt     1104
Ile Ala Glu Leu Leu Arg Phe Ala Asp Arg Glu Phe Tyr Arg Asp Phe
        355                 360                 365 tgg aat gca gag acg ata gga tat ttc tgg aaa tca tgg aac atc cca     1152
Trp Asn Ala Glu Thr Ile Gly Tyr Phe Trp Lys Ser Trp Asn Ile Pro
    370                 375                 380 gtt cac cga ttt gct gtt cgc cac atc tac agt cca atg atg cgt aac     1200
Val His Arg Phe Ala Val Arg His Ile Tyr Ser Pro Met Met Arg Asn
```

```
                385                 390                 395                 400
aat ttc tca aaa atg agc gca ttc ttc gtt gtg ttc ttc gtg tcg gca         1248
Asn Phe Ser Lys Met Ser Ala Phe Phe Val Val Phe Phe Val Ser Ala
                405                 410                 415 ttc ttc cat gaa tat ctg gtt tct gtg cca tta aag att ttc cga ttg         1296
Phe Phe His Glu Tyr Leu Val Ser Val Pro Leu Lys Ile Phe Arg Leu
                420                 425                 430 tgg tcc tac tat gga atg atg gga caa att cct cta tcc att atc act         1344
Trp Ser Tyr Tyr Gly Met Met Gly Gln Ile Pro Leu Ser Ile Ile Thr
                435                 440                 445 gat aaa gtg gtg aga ggt gga cgt aca gga aac atc atc gtc tgg ctc         1392
Asp Lys Val Val Arg Gly Gly Arg Thr Gly Asn Ile Ile Val Trp Leu
                450                 455                 460 tca ctg att gtt ggc caa cct ctt gca att ctc atg tac gga cat gat         1440
Ser Leu Ile Val Gly Gln Pro Leu Ala Ile Leu Met Tyr Gly His Asp
465                 470                 475                 480 tgg tac att ttg aac ttt ggt gtt tca gca gtt caa aac caa acc gtt         1488
Trp Tyr Ile Leu Asn Phe Gly Val Ser Ala Val Gln Asn Gln Thr Val
                485                 490                 495 ggt att tga                                                             1497
Gly Ile *

<210> SEQ ID NO 6
<211> LENGTH: 1698
<212> TYPE: DNA
<213> ORGANISM: Drosophila melanogaster
<220> FEATURE:
<221> NAME/KEY: CDS
<222> LOCATION: (1)...(1698)
<223> OTHER INFORMATION: Drosophila melanogaster clone 12 acyl coenzyme
      A:diacylglycerol
      acyltransferase coding sequence

<400> SEQUENCE: 6 atg act acc aat aag gat ccc caa gat aag gag ccc ggg aaa gca gaa           48
Met Thr Thr Asn Lys Asp Pro Gln Asp Lys Glu Pro Gly Lys Ala Glu
1               5                   10                  15 caa ccg acc aag aat agc gga tcc agc gga gtg ggt atc atg aag cgc           96
Gln Pro Thr Lys Asn Ser Gly Ser Ser Gly Val Gly Ile Met Lys Arg
                20                  25                  30 ttg aga aga tcg gcg tcc gcc aca gag cat aat ctt agc agt ctg cga          144
Leu Arg Arg Ser Ala Ser Ala Thr Glu His Asn Leu Ser Ser Leu Arg
            35                  40                  45 aac cgc aag tca aca caa aat cta ttc gat cag cac ggg aat ccc ata          192
Asn Arg Lys Ser Thr Gln Asn Leu Phe Asp Gln His Gly Asn Pro Ile
        50                  55                  60 gat ctg cga cag tat cgt aaa gtt ttg gat aag gat gaa aat ggt aat          240
Asp Leu Arg Gln Tyr Arg Lys Val Leu Asp Lys Asp Glu Asn Gly Asn
65                  70                  75                  80 gga acc aac gga tcc gag aag aag ctt aga tac agg aga aca caa agt          288
Gly Thr Asn Gly Ser Glu Lys Lys Leu Arg Tyr Arg Arg Thr Gln Ser
                85                  90                  95 gtg act cgt gct gag gag att tcc aat aaa gag gag aag cag aga aga          336
Val Thr Arg Ala Glu Glu Ile Ser Asn Lys Glu Glu Lys Gln Arg Arg
                100                 105                 110 gct cag cct ggc aga cca atc cat cgg cca aga gat tct ctg ttt tct          384
Ala Gln Pro Gly Arg Pro Ile His Arg Pro Arg Asp Ser Leu Phe Ser
            115                 120                 125 tgg agc tct gga ttt acc aat ttt tct gga ctg gtg aac tgg gga ttt          432
Trp Ser Ser Gly Phe Thr Asn Phe Ser Gly Leu Val Asn Trp Gly Phe
        130                 135                 140
```

```
cta ctg ctc tgc att gga ggt ctg cgt ttg ggc ttg gag aat ctc cta      480
Leu Leu Leu Cys Ile Gly Gly Leu Arg Leu Gly Leu Glu Asn Leu Leu
145                 150                 155                 160 aag tat ggc att cgc atc aat cca ctg gat tgg ttc ttc ttc ata agc      528
Lys Tyr Gly Ile Arg Ile Asn Pro Leu Asp Trp Phe Phe Phe Ile Ser
                165                 170                 175 gga cac aac gaa ggc gaa gga cat aac gcc cta atc ctg agc att tac      576
Gly His Asn Glu Gly Glu Gly His Asn Ala Leu Ile Leu Ser Ile Tyr
            180                 185                 190 tct tta gtg cat atc tcg ctc tgt ttg gct gtg gag aag ggt cta gcc      624
Ser Leu Val His Ile Ser Leu Cys Leu Ala Val Glu Lys Gly Leu Ala
        195                 200                 205 atg gaa ata att gca gag ggc ttg ggc ttg ttc atc cag ata gtg aac      672
Met Glu Ile Ile Ala Glu Gly Leu Gly Leu Phe Ile Gln Ile Val Asn
    210                 215                 220 att gtt gtc ttg gtt tgc cta ccg gtg gta aca att cac cta aaa gga      720
Ile Val Val Leu Val Cys Leu Pro Val Val Thr Ile His Leu Lys Gly
225                 230                 235                 240 cat gct ttt agt ttg atg ggc gct tca aca gtt tgc ttc ttt tac tct      768
His Ala Phe Ser Leu Met Gly Ala Ser Thr Val Cys Phe Phe Tyr Ser
                245                 250                 255 gtg ttg ttc cta aaa cta tgg tcc tat gtg cag acg aat atg tgg tgc      816
Val Leu Phe Leu Lys Leu Trp Ser Tyr Val Gln Thr Asn Met Trp Cys
            260                 265                 270 cgt cag act tat tat caa aag aat ccg cgg gag cgt cga cca agc ata      864
Arg Gln Thr Tyr Tyr Gln Lys Asn Pro Arg Glu Arg Arg Pro Ser Ile
        275                 280                 285 act ttg gcg gaa cta aaa aaa gga gtt ttg aat gga ggt gaa gaa gac      912
Thr Leu Ala Glu Leu Lys Lys Gly Val Leu Asn Gly Gly Glu Glu Asp
    290                 295                 300 gag gac gtt tcc aag ctg gtg caa tat cct gat aat ctc aca tac aat      960
Glu Asp Val Ser Lys Leu Val Gln Tyr Pro Asp Asn Leu Thr Tyr Asn
305                 310                 315                 320 gat ctc ctg tac ttc ctt tgc gcg ccc act ctc tgc tat gag ttg aat     1008
Asp Leu Leu Tyr Phe Leu Cys Ala Pro Thr Leu Cys Tyr Glu Leu Asn
                325                 330                 335 ttc ccg cga act tct cgc gtg cgc aaa cgc ttt ttg ctg aag cgt tta     1056
Phe Pro Arg Thr Ser Arg Val Arg Lys Arg Phe Leu Leu Lys Arg Leu
            340                 345                 350 ttg gag gtg gtg att gga gtg aat gtg gtt atg gcc ttg ttt caa caa     1104
Leu Glu Val Val Ile Gly Val Asn Val Val Met Ala Leu Phe Gln Gln
        355                 360                 365 tgg atc att cca tcg gtt cgg aac tcc ctg att ccg ttc tcc aat atg     1152
Trp Ile Ile Pro Ser Val Arg Asn Ser Leu Ile Pro Phe Ser Asn Met
    370                 375                 380 gac gtg gcc tta gcc act gag cga ctt ctt aaa ctt gcg cta ccc aat     1200
Asp Val Ala Leu Ala Thr Glu Arg Leu Leu Lys Leu Ala Leu Pro Asn
385                 390                 395                 400 cat ctt tgc tgg ctc tgc ttt ttc tat cta atg ttc cac tct ttt ctt     1248
His Leu Cys Trp Leu Cys Phe Phe Tyr Leu Met Phe His Ser Phe Leu
                405                 410                 415 aat gcg gtc ggc gaa ctg ctg aac ttt gca gat cgc aat ttt tat tgt     1296
Asn Ala Val Gly Glu Leu Leu Asn Phe Ala Asp Arg Asn Phe Tyr Cys
            420                 425                 430 gat tgg tgg aat gcg aat aac att gac acc ttc tgg cgt aca tgg aac     1344
Asp Trp Trp Asn Ala Asn Asn Ile Asp Thr Phe Trp Arg Thr Trp Asn
        435                 440                 445 atg cca gtt cat agg tgg tgc gtg cgt cat ctc tac atc cct gtg gtc     1392
Met Pro Val His Arg Trp Cys Val Arg His Leu Tyr Ile Pro Val Val
    450                 455                 460
```

| | | | | | | | | | | | | | | | | |
|---|---|---|---|---|---|---|---|---|---|---|---|---|---|---|---|---|
| caa | atg | gga | tat | tcc | tca | aga | cag | gcc | tct | act | att | gtc | ttt | ctt | ttc | 1440 |
| Gln | Met | Gly | Tyr | Ser | Ser | Arg | Gln | Ala | Ser | Thr | Ile | Val | Phe | Leu | Phe | |
| 465 | | | | | 470 | | | | | 475 | | | | | 480 | |

| | | | | | | | | | | | | | | | | |
|---|---|---|---|---|---|---|---|---|---|---|---|---|---|---|---|---|
| agt | gcc | gtc | ttc | cat | gaa | tat | ttg | gtt | tca | gtt | cct | ttg | caa | ata | tac | 1488 |
| Ser | Ala | Val | Phe | His | Glu | Tyr | Leu | Val | Ser | Val | Pro | Leu | Gln | Ile | Tyr | |
| | | | | | 485 | | | | | 490 | | | | | 495 | |

| | | | | | | | | | | | | | | | | |
|---|---|---|---|---|---|---|---|---|---|---|---|---|---|---|---|---|
| aag | atc | tgg | gca | ttt | atg | ggc | atg | atg | ggt | cag | att | ccc | cta | tcg | gcc | 1536 |
| Lys | Ile | Trp | Ala | Phe | Met | Gly | Met | Met | Gly | Gln | Ile | Pro | Leu | Ser | Ala | |
| | | | | 500 | | | | | 505 | | | | | 510 | | |

| | | | | | | | | | | | | | | | | |
|---|---|---|---|---|---|---|---|---|---|---|---|---|---|---|---|---|
| ata | tcc | aaa | tcc | att | gaa | aag | aaa | ctg | ggt | ccc | cga | atg | ggc | aat | ata | 1584 |
| Ile | Ser | Lys | Ser | Ile | Glu | Lys | Lys | Leu | Gly | Pro | Arg | Met | Gly | Asn | Ile | |
| | | | | 515 | | | | | 520 | | | | | 525 | | |

| | | | | | | | | | | | | | | | | |
|---|---|---|---|---|---|---|---|---|---|---|---|---|---|---|---|---|
| atc | gtg | tgg | gct | tcc | att | att | ctt | ggt | cag | cct | ctg | tgc | ata | atg | gcc | 1632 |
| Ile | Val | Trp | Ala | Ser | Ile | Ile | Leu | Gly | Gln | Pro | Leu | Cys | Ile | Met | Ala | |
| | | 530 | | | | | 535 | | | | | 540 | | | | |

| | | | | | | | | | | | | | | | | |
|---|---|---|---|---|---|---|---|---|---|---|---|---|---|---|---|---|
| tat | tat | cac | gat | tat | gtc | gtc | cag | cat | ttc | aaa | aac | tcg | ctc | aac | ggc | 1680 |
| Tyr | Tyr | His | Asp | Tyr | Val | Val | Gln | His | Phe | Lys | Asn | Ser | Leu | Asn | Gly | |
| 545 | | | | | 550 | | | | | 555 | | | | | 560 | |

| | | | | | |
|---|---|---|---|---|---|
| acc | gac | tac | agt | agt | tag | 1698 |
| Thr | Asp | Tyr | Ser | Ser | * | |
| | | | 565 | | | |

<210> SEQ ID NO 7
<211> LENGTH: 1470
<212> TYPE: DNA
<213> ORGANISM: Sus scrofa
<220> FEATURE:
<221> NAME/KEY: CDS
<222> LOCATION: (1)...(1470)
<223> OTHER INFORMATION: Sus scrofa diacylglycerol acyltransferase
      (DGAT) coding sequence

<400> SEQUENCE: 7

| | | | | | | | | | | | | | | | | |
|---|---|---|---|---|---|---|---|---|---|---|---|---|---|---|---|---|
| atg | ggt | gac | cgc | agc | ggc | gcg | ggc | ggc | tcc | cgg | cgc | cgg | agg | acg | ggg | 48 |
| Met | Gly | Asp | Arg | Ser | Gly | Ala | Gly | Gly | Ser | Arg | Arg | Arg | Arg | Thr | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tcg | cgg | ccc | tcc | agc | cag | agc | ggc | agc | ggg | ttc | gcg | gcc | gca | gaa | gag | 96 |
| Ser | Arg | Pro | Ser | Ser | Gln | Ser | Gly | Ser | Gly | Phe | Ala | Ala | Ala | Glu | Glu | |
| | | | 20 | | | | | 25 | | | | | 30 | | | |

| | | | | | | | | | | | | | | | | |
|---|---|---|---|---|---|---|---|---|---|---|---|---|---|---|---|---|
| gag | gtg | cgg | gac | gta | ggc | gcc | ggg | ggg | gac | gca | ccg | acg | ccg | gac | aag | 144 |
| Glu | Val | Arg | Asp | Val | Gly | Ala | Gly | Gly | Asp | Ala | Pro | Thr | Pro | Asp | Lys | |
| | | 35 | | | | | 40 | | | | | 45 | | | | |

| | | | | | | | | | | | | | | | | |
|---|---|---|---|---|---|---|---|---|---|---|---|---|---|---|---|---|
| gac | aag | gac | gga | cac | gac | gat | gtg | agc | agc | ggc | cac | tgg | gat | ctg | agg | 192 |
| Asp | Lys | Asp | Gly | His | Asp | Asp | Val | Ser | Ser | Gly | His | Trp | Asp | Leu | Arg | |
| | 50 | | | | | 55 | | | | | 60 | | | | | |

| | | | | | | | | | | | | | | | | |
|---|---|---|---|---|---|---|---|---|---|---|---|---|---|---|---|---|
| tgc | cac | cgc | ctg | cag | gat | tct | ttg | ttc | agt | tca | gac | agt | ggt | tcc | agc | 240 |
| Cys | His | Arg | Leu | Gln | Asp | Ser | Leu | Phe | Ser | Ser | Asp | Ser | Gly | Phe | Ser | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| aac | tac | cgt | ggc | atc | ctg | aat | tgg | tgt | gtg | gtc | atg | ctg | gtc | ttg | agc | 288 |
| Asn | Tyr | Arg | Gly | Ile | Leu | Asn | Trp | Cys | Val | Val | Met | Leu | Val | Leu | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| aat | gca | cgg | ctg | ttt | cta | gag | aac | ctc | atc | aag | tac | ggc | atc | ctg | gta | 336 |
| Asn | Ala | Arg | Leu | Phe | Leu | Glu | Asn | Leu | Ile | Lys | Tyr | Gly | Ile | Leu | Val | |
| | | | 100 | | | | | 105 | | | | | 110 | | | |

| | | | | | | | | | | | | | | | | |
|---|---|---|---|---|---|---|---|---|---|---|---|---|---|---|---|---|
| gac | ccc | atc | cag | gtg | gtg | tct | ctg | ttc | ctg | aag | gac | ccc | tat | agc | tgg | 384 |
| Asp | Pro | Ile | Gln | Val | Val | Ser | Leu | Phe | Leu | Lys | Asp | Pro | Tyr | Ser | Trp | |
| | | 115 | | | | | 120 | | | | | 125 | | | | |

| | | | | | | | | | | | | | | | | |
|---|---|---|---|---|---|---|---|---|---|---|---|---|---|---|---|---|
| cct | gcc | ctg | tgc | ctg | gtt | att | gtg | gcc | aat | gtc | ttt | gct | gtg | act | gcg | 432 |
| Pro | Ala | Leu | Cys | Leu | Val | Ile | Val | Ala | Asn | Val | Phe | Ala | Val | Thr | Ala | |
| | 130 | | | | | 135 | | | | | 140 | | | | | |

| | | | | | | | | | | | | | | | | |
|---|---|---|---|---|---|---|---|---|---|---|---|---|---|---|---|---|
| ttc | cag | gtg | gag | aag | cgc | ctg | gcc | gtg | ggt | gcc | ctg | acc | gag | cag | gcg | 480 |

-continued

| | | |
|---|---|---|
| Phe Gln Val Glu Lys Arg Leu Ala Val Gly Ala Leu Thr Glu Gln Ala<br>145                          150                             155                          160 | |
| ggg ctg ctg atc cac gtg gcc aac ctg gcc acc atc ctc tgc ttc cca<br>Gly Leu Leu Ile His Val Ala Asn Leu Ala Thr Ile Leu Cys Phe Pro<br>                          165                             170                          175 | 528 |
| gcg gcc gtg gct ttc ctg ctg gag tcc atc act cca gtg ggc tcc ctg<br>Ala Ala Val Ala Phe Leu Leu Glu Ser Ile Thr Pro Val Gly Ser Leu<br>                        180                             185                          190 | 576 |
| ctg gct ctg atg gtc tac gcc atc ctc ttc ctc aag ctg ttc tcc tac<br>Leu Ala Leu Met Val Tyr Ala Ile Leu Phe Leu Lys Leu Phe Ser Tyr<br>               195                             200                          205 | 624 |
| cgg gac gtc aac ctg tgg tgc cga gag cgc agg gct act gcc aag gcc<br>Arg Asp Val Asn Leu Trp Cys Arg Glu Arg Arg Ala Thr Ala Lys Ala<br>   210                            215                             220 | 672 |
| aag gcc gct tct gca ggt aag aag gcc aac ggg ggc gcc gcc cag cac<br>Lys Ala Ala Ser Ala Gly Lys Lys Ala Asn Gly Gly Ala Ala Gln His<br>225                          230                             235                          240 | 720 |
| agc gtg agc tac ccc gac aac ctg acc tac cgc gat ctc tac tac ttc<br>Ser Val Ser Tyr Pro Asp Asn Leu Thr Tyr Arg Asp Leu Tyr Tyr Phe<br>                        245                             250                          255 | 768 |
| ctc ctg gcc ccg act ctg tgc tac gag ctc aac ttt tcc cgc ttc ccg<br>Leu Leu Ala Pro Thr Leu Cys Tyr Glu Leu Asn Phe Ser Arg Phe Pro<br>               260                             265                          270 | 816 |
| cgc atc cga aag cgc ttc ctg ctg cgg cgg ctg ctg gag atg ctg ttc<br>Arg Ile Arg Lys Arg Phe Leu Leu Arg Arg Leu Leu Glu Met Leu Phe<br>   275                            280                             285 | 864 |
| ctc atc cag ctg cag gtg ggg ctg atc cag cag tgg atg gtc ccc acc<br>Leu Ile Gln Leu Gln Val Gly Leu Ile Gln Gln Trp Met Val Pro Thr<br>290                          295                             300 | 912 |
| atc cag aac tcc atg aag ccc ttc aag gac atg gac tac tca cgc atc<br>Ile Gln Asn Ser Met Lys Pro Phe Lys Asp Met Asp Tyr Ser Arg Ile<br>305                          310                             315                          320 | 960 |
| atc gag cgc ctc ctg aag ctg gcg gtg ccc aac cac ctc atc tgg ctc<br>Ile Glu Arg Leu Leu Lys Leu Ala Val Pro Asn His Leu Ile Trp Leu<br>                        325                             330                          335 | 1008 |
| atc ttc ttc tac tgg ctc ttc cac tcc tgc ctg aac gct gtg gct gag<br>Ile Phe Phe Tyr Trp Leu Phe His Ser Cys Leu Asn Ala Val Ala Glu<br>               340                             345                          350 | 1056 |
| ctc atg cag ttt gga gac cgg gag ttc tac cgg gac tgg tgg aac tcg<br>Leu Met Gln Phe Gly Asp Arg Glu Phe Tyr Arg Asp Trp Trp Asn Ser<br>                        355                             360                          365 | 1104 |
| gag tct gtc acc tac ttc tgg cag aac tgg aac atc cct gta cac aag<br>Glu Ser Val Thr Tyr Phe Trp Gln Asn Trp Asn Ile Pro Val His Lys<br>   370                            375                             380 | 1152 |
| tgg tgc ctc aga cac ttc tac aag ccc atg ctc cgg cgg ggc agc agc<br>Trp Cys Leu Arg His Phe Tyr Lys Pro Met Leu Arg Arg Gly Ser Ser<br>385                          390                             395                          400 | 1200 |
| aag tgg gta gcc agg atg ggg gtg ttc ctg gct tca gcc ttc ttc cac<br>Lys Trp Val Ala Arg Met Gly Val Phe Leu Ala Ser Ala Phe Phe His<br>                        405                             410                          415 | 1248 |
| gag tac ctg gtg agc atc cct ctg cgc atg ttc cgc ctc tgg gcc ttc<br>Glu Tyr Leu Val Ser Ile Pro Leu Arg Met Phe Arg Leu Trp Ala Phe<br>               420                             425                          430 | 1296 |
| acg ggc atg atg gct cag atc ccg ctg gct tgg ata gtg ggc cgc ttc<br>Thr Gly Met Met Ala Gln Ile Pro Leu Ala Trp Ile Val Gly Arg Phe<br>                        435                             440                          445 | 1344 |
| ttc cgt ggc aac tac ggc aac gcg gct gtg tgg ctg tcg ctc atc atc<br>Phe Arg Gly Asn Tyr Gly Asn Ala Ala Val Trp Leu Ser Leu Ile Ile<br>   450                            455                             460 | 1392 |

```
ggg cag ccg gtg gcc gtg ctc atg tac gtc cat gac tac tac gtg ctc    1440
Gly Gln Pro Val Ala Val Leu Met Tyr Val His Asp Tyr Tyr Val Leu
465                 470                 475                 480 cac cac gag gcc ccg aca gcg ggg gcc tga                            1470
His His Glu Ala Pro Thr Ala Gly Ala  *
                485

<210> SEQ ID NO 8
<211> LENGTH: 1167
<212> TYPE: DNA
<213> ORGANISM: Homo sapiens
<220> FEATURE:
<221> NAME/KEY: CDS
<222> LOCATION: (1)...(1167)
<223> OTHER INFORMATION: Homo sapiens DGAT 2 coding sequence

<400> SEQUENCE: 8 atg aag acc ctc ata gcc gcc tac tcc ggg gtc ctg cgc ggc gag cgt     48
Met Lys Thr Leu Ile Ala Ala Tyr Ser Gly Val Leu Arg Gly Glu Arg
1               5                   10                  15 cag gcc gag gct gac cgg agc cag cgc tct cac gga gga cct gcg ctg     96
Gln Ala Glu Ala Asp Arg Ser Gln Arg Ser His Gly Gly Pro Ala Leu
                20                  25                  30 tcg cgc gag ggg tct ggg aga tgg ggc act gga tcc agc atc ctc tcc    144
Ser Arg Glu Gly Ser Gly Arg Trp Gly Thr Gly Ser Ser Ile Leu Ser
            35                  40                  45 gcc ctc cag gac ctc ttc tct gtc acc tgg ctc aat agg tcc aag gtg    192
Ala Leu Gln Asp Leu Phe Ser Val Thr Trp Leu Asn Arg Ser Lys Val
        50                  55                  60 gaa aag cag cta cag gtc atc tca gtg ctc cag tgg gtc ctg tcc ttc    240
Glu Lys Gln Leu Gln Val Ile Ser Val Leu Gln Trp Val Leu Ser Phe
65                  70                  75                  80 ctt gta ctg gga gtg gcc tgc agt gcc atc ctc atg tac ata ttc tgc    288
Leu Val Leu Gly Val Ala Cys Ser Ala Ile Leu Met Tyr Ile Phe Cys
                85                  90                  95 act gat tgc tgg ctc atc gct gtg ctc tac ttc act tgg ctg gtg ttt    336
Thr Asp Cys Trp Leu Ile Ala Val Leu Tyr Phe Thr Trp Leu Val Phe
            100                 105                 110 gac tgg aac aca ccc aag aaa ggt ggc agg agg tca cag tgg gtc cga    384
Asp Trp Asn Thr Pro Lys Lys Gly Gly Arg Arg Ser Gln Trp Val Arg
        115                 120                 125 aac tgg gct gtg tgg cgc tac ttt cga gac tac ttt ccc atc cag ctg    432
Asn Trp Ala Val Trp Arg Tyr Phe Arg Asp Tyr Phe Pro Ile Gln Leu
    130                 135                 140 gtg aag aca cac aac ctg ctg acc acc agg aac tat atc ttt gga tac    480
Val Lys Thr His Asn Leu Leu Thr Thr Arg Asn Tyr Ile Phe Gly Tyr
145                 150                 155                 160 cac ccc cat ggt atc atg ggc ctg ggt gcc ttc tgc aac ttc agc aca    528
His Pro His Gly Ile Met Gly Leu Gly Ala Phe Cys Asn Phe Ser Thr
                165                 170                 175 gag gcc aca gaa gtg agc aag aag ttc cca ggc ata cgg cct tac ctg    576
Glu Ala Thr Glu Val Ser Lys Lys Phe Pro Gly Ile Arg Pro Tyr Leu
            180                 185                 190 gct aca ctg gca ggc aac ttc cga atg cct gtg ttg agg gag tac ctg    624
Ala Thr Leu Ala Gly Asn Phe Arg Met Pro Val Leu Arg Glu Tyr Leu
        195                 200                 205 atg tct gga ggt atc tgc cct gtc agc cgg gac acc ata gac tat ttg    672
Met Ser Gly Gly Ile Cys Pro Val Ser Arg Asp Thr Ile Asp Tyr Leu
    210                 215                 220 ctt tca aag aat ggg agt ggc aat gct atc atc atc gtg gtc ggg ggt    720
Leu Ser Lys Asn Gly Ser Gly Asn Ala Ile Ile Ile Val Val Gly Gly
225                 230                 235                 240
```

-continued

```
gcg gct gag tct ctg agc tcc atg cct ggc aag aat gca gtc acc ctg        768
Ala Ala Glu Ser Leu Ser Ser Met Pro Gly Lys Asn Ala Val Thr Leu
                245                 250                 255 cgg aac cgc aag ggc ttt gtg aaa ctg gcc ctg cgt cat gga gct gac        816
Arg Asn Arg Lys Gly Phe Val Lys Leu Ala Leu Arg His Gly Ala Asp
            260                 265                 270 ctg gtt ccc atc tac tcc ttt gga gag aat gaa gtg tac aag cag gtg        864
Leu Val Pro Ile Tyr Ser Phe Gly Glu Asn Glu Val Tyr Lys Gln Val
        275                 280                 285 atc ttc gag gag ggc tcc tgg ggc cga tgg gtc cag aag aag ttc cag        912
Ile Phe Glu Glu Gly Ser Trp Gly Arg Trp Val Gln Lys Lys Phe Gln
    290                 295                 300 aaa tac att ggt ttc gcc cca tgc atc ttc cat ggt cga ggc ctc ttc        960
Lys Tyr Ile Gly Phe Ala Pro Cys Ile Phe His Gly Arg Gly Leu Phe
305                 310                 315                 320 tcc tcc gac acc tgg ggg ctg gtg ccc tac tcc aag ccc atc acc act       1008
Ser Ser Asp Thr Trp Gly Leu Val Pro Tyr Ser Lys Pro Ile Thr Thr
                325                 330                 335 gtt gtg gga gag ccc atc acc atc ccc aag ctg gag cac cca acc cag       1056
Val Val Gly Glu Pro Ile Thr Ile Pro Lys Leu Glu His Pro Thr Gln
            340                 345                 350 caa gac atc gac ctg tac cac acc atg tac atg gag gcc ctg gtg aag       1104
Gln Asp Ile Asp Leu Tyr His Thr Met Tyr Met Glu Ala Leu Val Lys
        355                 360                 365 ctc ttc gac aag cac aag acc aag ttc ggc ctc ccg gag act gag gtc       1152
Leu Phe Asp Lys His Lys Thr Lys Phe Gly Leu Pro Glu Thr Glu Val
    370                 375                 380 ctg gag gtg aac tga                                                    1167
Leu Glu Val Asn *
385

<210> SEQ ID NO 9
<211> LENGTH: 1467
<212> TYPE: DNA
<213> ORGANISM: Homo sapiens
<220> FEATURE:
<221> NAME/KEY: CDS
<222> LOCATION: (1)...(1467)
<223> OTHER INFORMATION: Homo sapiens diacylglycerol O-acyltransferase
      homolog 1 (DGAT1), coding sequence

<400> SEQUENCE: 9 atg ggc gac cgc ggc agc tcc cgg cgc cgg agg aca ggg tcg cgg ccc         48
Met Gly Asp Arg Gly Ser Ser Arg Arg Arg Arg Thr Gly Ser Arg Pro
1               5                   10                  15 tcg agc cac ggc ggc ggg cct gcg gcg gcg gaa gaa gag gtg cgg          96
Ser Ser His Gly Gly Gly Gly Pro Ala Ala Ala Glu Glu Glu Val Arg
                20                  25                  30 gac gcc gct gcg ggc ccc gac gtg gga gcc gcg ggg gac gcg cca gcc        144
Asp Ala Ala Ala Gly Pro Asp Val Gly Ala Ala Gly Asp Ala Pro Ala
            35                  40                  45 ccg gcc ccc aac aag gac gga gac gcc ggc gtg ggc agc ggc cac tgg        192
Pro Ala Pro Asn Lys Asp Gly Asp Ala Gly Val Gly Ser Gly His Trp
        50                  55                  60 gag ctg agg tgc cat cgc ctg cag gat tct tta ttc agc tct gac agt        240
Glu Leu Arg Cys His Arg Leu Gln Asp Ser Leu Phe Ser Ser Asp Ser
65                  70                  75                  80 ggc ttc agc aac tac cgt ggc atc ctg aac tgg tgt gtg gtg atg ctg        288
Gly Phe Ser Asn Tyr Arg Gly Ile Leu Asn Trp Cys Val Val Met Leu
                85                  90                  95 atc ttg agc aat gcc cgg tta ttt ctg gag aac ctc atc aag tat ggc        336
```

-continued

```
Ile Leu Ser Asn Ala Arg Leu Phe Leu Glu Asn Leu Ile Lys Tyr Gly
                100                 105                 110 atc ctg gtg gac ccc atc cag gtg gtt tct ctg ttc ctg aag gat ccc    384
Ile Leu Val Asp Pro Ile Gln Val Val Ser Leu Phe Leu Lys Asp Pro
        115                 120                 125 cat agc tgg ccc gcc cca tgc ctg gtt att gcg gcc aat gtc ttt gct    432
His Ser Trp Pro Ala Pro Cys Leu Val Ile Ala Ala Asn Val Phe Ala
130                 135                 140 gtg gct gca ttc cag gtt gag aag cgc ctg gcg gtt ggt gcc ctg acg    480
Val Ala Ala Phe Gln Val Glu Lys Arg Leu Ala Val Gly Ala Leu Thr
145                 150                 155                 160 gag cag gcg gga ctg ctg ctg cac gta gcc aac ctg gcc acc att ctg    528
Glu Gln Ala Gly Leu Leu Leu His Val Ala Asn Leu Ala Thr Ile Leu
                165                 170                 175 tgt ttc cca gcg gct gtg gtc tta ctg gtt gag tct atc act cca gtg    576
Cys Phe Pro Ala Ala Val Val Leu Leu Val Glu Ser Ile Thr Pro Val
            180                 185                 190 ggc tcc ctg ctg gcg ctg atg gcg cac acc atc ctc ttc ctc aag ctc    624
Gly Ser Leu Leu Ala Leu Met Ala His Thr Ile Leu Phe Leu Lys Leu
        195                 200                 205 ttc tcc tac cgc gac gtc aac tca tgg tgc cgc agg gcc agg gcc aag    672
Phe Ser Tyr Arg Asp Val Asn Ser Trp Cys Arg Arg Ala Arg Ala Lys
210                 215                 220 gct gcc tct gca ggg aag aag gcc agc agt gct gct gcc ccg cac acc    720
Ala Ala Ser Ala Gly Lys Lys Ala Ser Ser Ala Ala Ala Pro His Thr
225                 230                 235                 240 gtg agc tac ccg gac aat ctg acc tac cgc gat ctc tac tac ttc ctc    768
Val Ser Tyr Pro Asp Asn Leu Thr Tyr Arg Asp Leu Tyr Tyr Phe Leu
                245                 250                 255 ttc gcc ccc acc ttg tgc tac gag ctc aac ttt ccc cgc tct ccc cgc    816
Phe Ala Pro Thr Leu Cys Tyr Glu Leu Asn Phe Pro Arg Ser Pro Arg
            260                 265                 270 atc cgg aag cgc ttt ctg ctg cga cgg atc ctt gag atg ctg ttc ttc    864
Ile Arg Lys Arg Phe Leu Leu Arg Arg Ile Leu Glu Met Leu Phe Phe
        275                 280                 285 acc cag ctc cag gtg ggg ctg atc cag cag tgg atg gtc ccc acc atc    912
Thr Gln Leu Gln Val Gly Leu Ile Gln Gln Trp Met Val Pro Thr Ile
290                 295                 300 cag aac tcc atg aag ccc ttc aag gac atg gac tac tca cgc atc atc    960
Gln Asn Ser Met Lys Pro Phe Lys Asp Met Asp Tyr Ser Arg Ile Ile
305                 310                 315                 320 gag cgc ctc ctg aag ctg gcg gtc ccc aat cac ctc atc tgg ctc atc   1008
Glu Arg Leu Leu Lys Leu Ala Val Pro Asn His Leu Ile Trp Leu Ile
                325                 330                 335 ttc ttc tac tgg ctc ttc cac tcc tgc ctg aat gcc gtg gct gag ctc   1056
Phe Phe Tyr Trp Leu Phe His Ser Cys Leu Asn Ala Val Ala Glu Leu
            340                 345                 350 atg cag ttt gga gac cgg gag ttc tac cgg gac tgg tgg aac tcc gag   1104
Met Gln Phe Gly Asp Arg Glu Phe Tyr Arg Asp Trp Trp Asn Ser Glu
        355                 360                 365 tct gtc acc tac ttc tgg cag aac tgg aac atc cct gtg cac aag tgg   1152
Ser Val Thr Tyr Phe Trp Gln Asn Trp Asn Ile Pro Val His Lys Trp
370                 375                 380 tgc atc aga cac ttc tac aag ccc atg ctt cga cgg ggc agc agc aag   1200
Cys Ile Arg His Phe Tyr Lys Pro Met Leu Arg Arg Gly Ser Ser Lys
385                 390                 395                 400 tgg atg gcc agg aca ggg gtg ttc ctg gcc tcg gct ttc ttc cac gag   1248
Trp Met Ala Arg Thr Gly Val Phe Leu Ala Ser Ala Phe Phe His Glu
                405                 410                 415
```

```
tac ctg gtg agc gtc cct ctg cga atg ttc cgc ctc tgg gct ttc acg      1296
Tyr Leu Val Ser Val Pro Leu Arg Met Phe Arg Leu Trp Ala Phe Thr
            420                 425                 430 ggc atg atg gct cag atc cca ctg gcc tgg ttc gtg ggc cgc ttt ttc      1344
Gly Met Met Ala Gln Ile Pro Leu Ala Trp Phe Val Gly Arg Phe Phe
        435                 440                 445 cag ggc aac tat ggc aac gca gct gtg tgg ctg tcg ctc atc atc gga      1392
Gln Gly Asn Tyr Gly Asn Ala Ala Val Trp Leu Ser Leu Ile Ile Gly
    450                 455                 460 cag cca ata gcc gtc ctc atg tac gtc cac gac tac tac gtg ctc aac      1440
Gln Pro Ile Ala Val Leu Met Tyr Val His Asp Tyr Tyr Val Leu Asn
465                 470                 475                 480 tat gag gcc cca gcg gca gag gcc tga                                  1467
Tyr Glu Ala Pro Ala Ala Glu Ala *
                485

<210> SEQ ID NO 10
<211> LENGTH: 1005
<212> TYPE: DNA
<213> ORGANISM: Homo sapiens
<220> FEATURE:
<221> NAME/KEY: CDS
<222> LOCATION: (1)...(1005)
<223> OTHER INFORMATION: Homo sapiens diacylglycerol acyltransferase
      2-like protein coding sequence

<400> SEQUENCE: 10 atg aag gta gag ttt gca ccg ctc aac atc cag ctg gcg cgg cgg ctg       48
Met Lys Val Glu Phe Ala Pro Leu Asn Ile Gln Leu Ala Arg Arg Leu
1               5                   10                  15 cag acg gtg gcc gtg ctg cag tgg gtc ctt tct ttt ctt aca ggg ccg       96
Gln Thr Val Ala Val Leu Gln Trp Val Leu Ser Phe Leu Thr Gly Pro
            20                  25                  30 atg tcc att gga atc act gtg atg ctg atc ata cac aac tat ttg ttc      144
Met Ser Ile Gly Ile Thr Val Met Leu Ile Ile His Asn Tyr Leu Phe
        35                  40                  45 ctt tac atc cct tat ttg atg tgg ctt tac ttt gac tgg cat acc cca      192
Leu Tyr Ile Pro Tyr Leu Met Trp Leu Tyr Phe Asp Trp His Thr Pro
    50                  55                  60 gag cga gga ggc agg aga tcc agc tgg atc aaa aat tgg act ctt tgg      240
Glu Arg Gly Gly Arg Arg Ser Ser Trp Ile Lys Asn Trp Thr Leu Trp
65                  70                  75                  80 aaa cac ttt aag gac tat ttt cca att cat ctt atc aaa act caa gat      288
Lys His Phe Lys Asp Tyr Phe Pro Ile His Leu Ile Lys Thr Gln Asp
                85                  90                  95 ttg gat cca agt cac aac tat ata ttt ggg ttt cac ccc cat gga ata      336
Leu Asp Pro Ser His Asn Tyr Ile Phe Gly Phe His Pro His Gly Ile
            100                 105                 110 atg gca gtt gga gcc ttt ggg aat ttt tct gta aat tat tct gac ttc      384
Met Ala Val Gly Ala Phe Gly Asn Phe Ser Val Asn Tyr Ser Asp Phe
        115                 120                 125 aag gac ctg ttt cct ggc ttt act tca tat ctt cac gtg ctg cca ctt      432
Lys Asp Leu Phe Pro Gly Phe Thr Ser Tyr Leu His Val Leu Pro Leu
    130                 135                 140 tgg ttc tgg tgt cct gtc ttt cga gaa tat gtg atg agt gtt ggg ctg      480
Trp Phe Trp Cys Pro Val Phe Arg Glu Tyr Val Met Ser Val Gly Leu
145                 150                 155                 160 gtt tca gtt tcc aag aaa agt gtg tcc tac atg gta agc aag gag gga      528
Val Ser Val Ser Lys Lys Ser Val Ser Tyr Met Val Ser Lys Glu Gly
                165                 170                 175 ggt gga aac atc tct gtc att gtc ctt ggg ggt gca aaa gaa tca ctg      576
Gly Gly Asn Ile Ser Val Ile Val Leu Gly Gly Ala Lys Glu Ser Leu
```

```
gat gct cat cct gga aag ttc act ctg ttc atc cgc cag cgg aaa gga    624
Asp Ala His Pro Gly Lys Phe Thr Leu Phe Ile Arg Gln Arg Lys Gly
        195                 200                 205 ttt gtt aaa att gct ttg acc cat ggc gcc tct ctg gtc cca gtg gtt    672
Phe Val Lys Ile Ala Leu Thr His Gly Ala Ser Leu Val Pro Val Val
    210                 215                 220 tct ttt ggt gaa aat gaa ctg ttt aaa caa act gac aac cct gaa gga    720
Ser Phe Gly Glu Asn Glu Leu Phe Lys Gln Thr Asp Asn Pro Glu Gly
225                 230                 235                 240 tca tgg att aga act gtt cag aat aaa ctg cag aag atc atg ggg ttt    768
Ser Trp Ile Arg Thr Val Gln Asn Lys Leu Gln Lys Ile Met Gly Phe
                245                 250                 255 gct ttg ccc ctg ttt cat gcc agg gga gtt ttt cag tac aat ttt ggc    816
Ala Leu Pro Leu Phe His Ala Arg Gly Val Phe Gln Tyr Asn Phe Gly
            260                 265                 270 cta atg acc tat agg aaa gcc atc cac act gtt gtt ggc cgc ccg atc    864
Leu Met Thr Tyr Arg Lys Ala Ile His Thr Val Val Gly Arg Pro Ile
        275                 280                 285 cct gtt cgt cag act ctg aac ccg acc cag gag cag att gag gag tta    912
Pro Val Arg Gln Thr Leu Asn Pro Thr Gln Glu Gln Ile Glu Glu Leu
    290                 295                 300 cat cag acc tat atg gag gaa ctt agg aaa ttg ttt gag gaa cac aaa    960
His Gln Thr Tyr Met Glu Glu Leu Arg Lys Leu Phe Glu Glu His Lys
305                 310                 315                 320 gga aag tat ggc att cca gag cac gag act ctt gtt tta aaa tga       1005
Gly Lys Tyr Gly Ile Pro Glu His Glu Thr Leu Val Leu Lys *
                325                 330

<210> SEQ ID NO 11
<211> LENGTH: 1008
<212> TYPE: DNA
<213> ORGANISM: Mus musculus
<220> FEATURE:
<221> NAME/KEY: CDS
<222> LOCATION: (1)...(1008)
<223> OTHER INFORMATION: Mus musculus diacylglycerol acyltransferase
      2-like protein coding sequence

<400> SEQUENCE: 11 atg atg gtc gag ttc gcg cca ctc aac acc ccg ctg gca cgt tgc cta     48
Met Met Val Glu Phe Ala Pro Leu Asn Thr Pro Leu Ala Arg Cys Leu
1               5                   10                  15 cag acc gct gcg gtg ctg cag tgg gtc ctg tcc ttc ctc ctg ctc gtg     96
Gln Thr Ala Ala Val Leu Gln Trp Val Leu Ser Phe Leu Leu Leu Val
            20                  25                  30 cag gtg tgc att gga att atg gtg atg ctg gtc ctg tac aac tat tgg    144
Gln Val Cys Ile Gly Ile Met Val Met Leu Val Leu Tyr Asn Tyr Trp
        35                  40                  45 ttc ctt tac atc cca tat ctg gtc tgg ttt tac tat gac tgg aga acc    192
Phe Leu Tyr Ile Pro Tyr Leu Val Trp Phe Tyr Tyr Asp Trp Arg Thr
    50                  55                  60 cca gag caa gga ggc aga aga tgg aac tgg gtc caa agc tgg cct gtg    240
Pro Glu Gln Gly Gly Arg Arg Trp Asn Trp Val Gln Ser Trp Pro Val
65                  70                  75                  80 tgg aag tat ttt aag gag tat ttt cca atc tgt ctt gtc aaa acg cag    288
Trp Lys Tyr Phe Lys Glu Tyr Phe Pro Ile Cys Leu Val Lys Thr Gln
                85                  90                  95 gat ttg gat ccg ggt cac aat tat ata ttt ggg ttt cac cct cat gga    336
Asp Leu Asp Pro Gly His Asn Tyr Ile Phe Gly Phe His Pro His Gly
            100                 105                 110
```

| | | | | | | | | | | | | | | | | |
|---|---|---|---|---|---|---|---|---|---|---|---|---|---|---|---|---|
| ata | ttc | gtg | cct | gga | gcc | ttt | gga | aat | ttt | tgt | aca | aaa | tac | tcg | gac | 384 |
| Ile | Phe | Val | Pro | Gly | Ala | Phe | Gly | Asn | Phe | Cys | Thr | Lys | Tyr | Ser | Asp | |
| | | | 115 | | | | | 120 | | | | | 125 | | | |
| ttc | aag | aag | cta | ttt | cct | ggc | ttt | aca | tcg | tat | ctc | cac | gtg | gcc | aag | 432 |
| Phe | Lys | Lys | Leu | Phe | Pro | Gly | Phe | Thr | Ser | Tyr | Leu | His | Val | Ala | Lys | |
| | | 130 | | | | | 135 | | | | | 140 | | | | |
| atc | tgg | ttc | tgt | ttc | ccg | ttg | ttc | cga | gaa | tat | ctg | atg | agt | aac | ggg | 480 |
| Ile | Trp | Phe | Cys | Phe | Pro | Leu | Phe | Arg | Glu | Tyr | Leu | Met | Ser | Asn | Gly | |
| 145 | | | | | 150 | | | | | 155 | | | | | 160 | |
| ccg | gtt | tca | gtg | tct | aag | gag | agt | ttg | tct | cat | gtg | ctg | agc | aag | gat | 528 |
| Pro | Val | Ser | Val | Ser | Lys | Glu | Ser | Leu | Ser | His | Val | Leu | Ser | Lys | Asp | |
| | | | | 165 | | | | | 170 | | | | | 175 | | |
| gga | ggt | ggc | aat | gtc | tca | atc | att | gtc | ctc | gga | ggt | gca | aag | gag | gcg | 576 |
| Gly | Gly | Gly | Asn | Val | Ser | Ile | Ile | Val | Leu | Gly | Gly | Ala | Lys | Glu | Ala | |
| | | | 180 | | | | | 185 | | | | | 190 | | | |
| ctg | gag | gct | cac | cca | gga | aca | ttc | acc | ctg | tgc | atc | cgc | cag | cgc | aaa | 624 |
| Leu | Glu | Ala | His | Pro | Gly | Thr | Phe | Thr | Leu | Cys | Ile | Arg | Gln | Arg | Lys | |
| | | 195 | | | | | 200 | | | | | 205 | | | | |
| ggg | ttt | gtt | aag | atg | gcc | ttg | acc | cat | ggt | gcc | agt | ttg | gtt | cca | gta | 672 |
| Gly | Phe | Val | Lys | Met | Ala | Leu | Thr | His | Gly | Ala | Ser | Leu | Val | Pro | Val | |
| | 210 | | | | | 215 | | | | | 220 | | | | | |
| ttt | tct | ttt | ggt | gaa | aat | gat | cta | tat | aag | caa | att | aac | aac | ccc | aaa | 720 |
| Phe | Ser | Phe | Gly | Glu | Asn | Asp | Leu | Tyr | Lys | Gln | Ile | Asn | Asn | Pro | Lys | |
| 225 | | | | | 230 | | | | | 235 | | | | | 240 | |
| ggc | tcc | tgg | cta | cga | act | ata | caa | gac | gca | atg | tat | gat | tca | atg | gga | 768 |
| Gly | Ser | Trp | Leu | Arg | Thr | Ile | Gln | Asp | Ala | Met | Tyr | Asp | Ser | Met | Gly | |
| | | | | 245 | | | | | 250 | | | | | 255 | | |
| gta | gcc | ttg | cca | ctg | ata | tat | gcc | aga | gga | att | ttc | cag | cac | tac | ttt | 816 |
| Val | Ala | Leu | Pro | Leu | Ile | Tyr | Ala | Arg | Gly | Ile | Phe | Gln | His | Tyr | Phe | |
| | | | 260 | | | | | 265 | | | | | 270 | | | |
| ggc | ata | atg | ccc | tat | cgg | aag | ctg | atc | tac | act | gtt | gtt | ggc | cgc | cct | 864 |
| Gly | Ile | Met | Pro | Tyr | Arg | Lys | Leu | Ile | Tyr | Thr | Val | Val | Gly | Arg | Pro | |
| | | 275 | | | | | 280 | | | | | 285 | | | | |
| atc | cct | gtt | cag | cag | att | ctg | aac | ccg | acc | tca | gag | cag | att | gaa | gag | 912 |
| Ile | Pro | Val | Gln | Gln | Ile | Leu | Asn | Pro | Thr | Ser | Glu | Gln | Ile | Glu | Glu | |
| | 290 | | | | | 295 | | | | | 300 | | | | | |
| ctg | cat | cag | aca | tac | cta | gag | gag | cta | aag | aaa | cta | ttc | aat | gaa | cac | 960 |
| Leu | His | Gln | Thr | Tyr | Leu | Glu | Glu | Leu | Lys | Lys | Leu | Phe | Asn | Glu | His | |
| 305 | | | | | 310 | | | | | 315 | | | | | 320 | |
| aaa | ggg | aaa | tat | ggg | att | ccg | gag | cac | gaa | act | ctg | gta | ttt | aaa | taa | 1008 |
| Lys | Gly | Lys | Tyr | Gly | Ile | Pro | Glu | His | Glu | Thr | Leu | Val | Phe | Lys | * | |
| | | | | 325 | | | | | 330 | | | | | 335 | | |

```
<210> SEQ ID NO 12
<211> LENGTH: 1497
<212> TYPE: DNA
<213> ORGANISM: Mus musculus
<220> FEATURE:
<221> NAME/KEY: CDS
<222> LOCATION: (1)...(1497)
<223> OTHER INFORMATION: Mus musculus diacylglycerol acyltransferase
      (Dgat) coding sequence

<400> SEQUENCE: 12
```

| | | | | | | | | | | | | | | | | |
|---|---|---|---|---|---|---|---|---|---|---|---|---|---|---|---|---|
| atg | ggc | gac | cgc | gga | ggc | gcg | gga | agc | tct | cgg | cgt | cgg | agg | acc | ggc | 48 |
| Met | Gly | Asp | Arg | Gly | Gly | Ala | Gly | Ser | Ser | Arg | Arg | Arg | Arg | Thr | Gly | |
| 1 | | | | 5 | | | | | 10 | | | | | 15 | | |
| tcg | cgg | gtt | tcc | gtc | cag | ggt | ggt | agt | ggg | ccc | aag | gta | gaa | gag | gac | 96 |
| Ser | Arg | Val | Ser | Val | Gln | Gly | Gly | Ser | Gly | Pro | Lys | Val | Glu | Glu | Asp | |
| | | | 20 | | | | | 25 | | | | | 30 | | | |
| gag | gtg | cga | gac | gcg | gct | gtg | agc | ccc | gac | ttg | ggc | gcc | ggg | ggt | gac | 144 |
| Glu | Val | Arg | Asp | Ala | Ala | Val | Ser | Pro | Asp | Leu | Gly | Ala | Gly | Gly | Asp | |

-continued

```
                    35                    40                    45
gcg ccg gct ccg gct ccg gct cca gcc cat acc cgg gac aaa gac ggg    192
Ala Pro Ala Pro Ala Pro Ala Pro Ala His Thr Arg Asp Lys Asp Gly
 50                  55                  60 cgg acc agc gtg ggc gac ggc tac tgg gat ctg agg tgc cat cgt ctg    240
Arg Thr Ser Val Gly Asp Gly Tyr Trp Asp Leu Arg Cys His Arg Leu
 65                  70                  75                  80 caa gat tct ttg ttc agc tca gac agt ggt ttc agc aat tat cgt ggt    288
Gln Asp Ser Leu Phe Ser Ser Asp Ser Gly Phe Ser Asn Tyr Arg Gly
                     85                  90                  95 atc ctg aat tgg tgt gtg gtg atg ctg atc ctg agt aat gca agg tta    336
Ile Leu Asn Trp Cys Val Val Met Leu Ile Leu Ser Asn Ala Arg Leu
                100                 105                 110 ttt tta gag aac ctt atc aag tat ggc atc ctg gtg gat cct atc cag    384
Phe Leu Glu Asn Leu Ile Lys Tyr Gly Ile Leu Val Asp Pro Ile Gln
            115                 120                 125 gtg gtg tct ctg ttt ttg aag gac ccc tac agc tgg cct gcc cca tgc    432
Val Val Ser Leu Phe Leu Lys Asp Pro Tyr Ser Trp Pro Ala Pro Cys
        130                 135                 140 gtg att att gca tcc aat att ttt gtt gtg gct gca ttt cag att gag    480
Val Ile Ile Ala Ser Asn Ile Phe Val Val Ala Ala Phe Gln Ile Glu
145                 150                 155                 160 aag cgc ctg gca gtg ggt gcc ctg aca gag cag atg ggg ctg ctg cta    528
Lys Arg Leu Ala Val Gly Ala Leu Thr Glu Gln Met Gly Leu Leu Leu
                165                 170                 175 cat gtg gtt aac ctg gcc aca atc att tgc ttc cca gca gct gtg gcc    576
His Val Val Asn Leu Ala Thr Ile Ile Cys Phe Pro Ala Ala Val Ala
            180                 185                 190 tta ctg gtt gag tct atc act cca gtg ggt tcc gtg ttt gct ctg gca    624
Leu Leu Val Glu Ser Ile Thr Pro Val Gly Ser Val Phe Ala Leu Ala
        195                 200                 205 tca tac tcc atc atg ttc ctc aag ctt tat tcc tac cgg gat gtc aac    672
Ser Tyr Ser Ile Met Phe Leu Lys Leu Tyr Ser Tyr Arg Asp Val Asn
210                 215                 220 ctg tgg tgc cgc cag cga agg gtc aag gcc aaa gct gtc tct aca ggg    720
Leu Trp Cys Arg Gln Arg Arg Val Lys Ala Lys Ala Val Ser Thr Gly
225                 230                 235                 240 aag aag gtc agt ggg gct gct gcc cag caa gct gtg agc tat cca gac    768
Lys Lys Val Ser Gly Ala Ala Ala Gln Gln Ala Val Ser Tyr Pro Asp
                245                 250                 255 aac ctg acc tac cga gat ctc tat tac ttc atc ttt gct cct act ttg    816
Asn Leu Thr Tyr Arg Asp Leu Tyr Tyr Phe Ile Phe Ala Pro Thr Leu
            260                 265                 270 tgt tat gaa ctc aac ttt cct cgg tcc ccc cga ata cga aag cgc ttt    864
Cys Tyr Glu Leu Asn Phe Pro Arg Ser Pro Arg Ile Arg Lys Arg Phe
        275                 280                 285 ctg cta cga cga gtt ctt gag atg ctc ttt ttt acc cag ctt caa gtg    912
Leu Leu Arg Arg Val Leu Glu Met Leu Phe Phe Thr Gln Leu Gln Val
290                 295                 300 ggg ctg atc caa cag tgg atg gtc cct act atc cag aac tcc atg aag    960
Gly Leu Ile Gln Gln Trp Met Val Pro Thr Ile Gln Asn Ser Met Lys
305                 310                 315                 320 ccc ttc aag gat atg gac tat tca cgg atc att gag cgt ctc tta aag    1008
Pro Phe Lys Asp Met Asp Tyr Ser Arg Ile Ile Glu Arg Leu Leu Lys
                325                 330                 335 ctg gcg gtc ccc aac cat ctg atc tgg ctt atc ttc ttc tat tgg ttt    1056
Leu Ala Val Pro Asn His Leu Ile Trp Leu Ile Phe Phe Tyr Trp Phe
            340                 345                 350 ttc cac tcc tgt ctc aat gct gtg gca gag ctt ctg cag ttt gga gac    1104
Phe His Ser Cys Leu Asn Ala Val Ala Glu Leu Leu Gln Phe Gly Asp
```

```
                Phe His Ser Cys Leu Asn Ala Val Ala Glu Leu Leu Gln Phe Gly Asp
                            355                 360                 365 cgc gag ttc tac aga gat tgg tgg aat gct gag tct gtc acc tac ttt      1152
Arg Glu Phe Tyr Arg Asp Trp Trp Asn Ala Glu Ser Val Thr Tyr Phe
    370                 375                 380 tgg cag aac tgg aat atc ccc gtg cac aag tgg tgc atc aga cac ttc      1200
Trp Gln Asn Trp Asn Ile Pro Val His Lys Trp Cys Ile Arg His Phe
385                 390                 395                 400 tac aag cct atg ctc aga cat ggc agc agc aaa tgg gtg gcc agg aca      1248
Tyr Lys Pro Met Leu Arg His Gly Ser Ser Lys Trp Val Ala Arg Thr
                405                 410                 415 gga gta ttt ttg acc tca gcc ttc ttc cat gag tac cta gtg agc gtt      1296
Gly Val Phe Leu Thr Ser Ala Phe Phe His Glu Tyr Leu Val Ser Val
            420                 425                 430 ccc ctg cgg atg ttc cgc ctc tgg gca ttc aca gcc atg atg gct cag      1344
Pro Leu Arg Met Phe Arg Leu Trp Ala Phe Thr Ala Met Met Ala Gln
        435                 440                 445 gtc cca ctg gcc tgg att gtg ggc cga ttc ttc caa ggg aac tat ggc      1392
Val Pro Leu Ala Trp Ile Val Gly Arg Phe Phe Gln Gly Asn Tyr Gly
    450                 455                 460 aat gca gct gtg tgg gtg aca ctc atc att ggg caa ccg gtg gct gtg      1440
Asn Ala Ala Val Trp Val Thr Leu Ile Ile Gly Gln Pro Val Ala Val
465                 470                 475                 480 ctc atg tat gtc cac gac tac tac gtg ctc aac tac gat gcc cca gtg      1488
Leu Met Tyr Val His Asp Tyr Tyr Val Leu Asn Tyr Asp Ala Pro Val
                485                 490                 495 ggg gta tga                                                          1497
Gly Val *

<210> SEQ ID NO 13
<211> LENGTH: 19
<212> TYPE: DNA
<213> ORGANISM: mus musculus

<400> SEQUENCE: 13 gtc gat tcc gcc ctc ggt g                                             19

<210> SEQ ID NO 14
<211> LENGTH: 20
<212> TYPE: DNA
<213> ORGANISM: Mus musculus

<400> SEQUENCE: 14
gagggaaagt gatgagatct                                                 20

<210> SEQ ID NO 15
<211> LENGTH: 19
<212> TYPE: DNA
<213> ORGANISM: Mus musculus

<400> SEQUENCE: 15
gtcggacaca gccttctgc                                                  19

<210> SEQ ID NO 16
<211> LENGTH: 19
<212> TYPE: DNA
<213> ORGANISM: Mus musculus

<400> SEQUENCE: 16
accttggacc gccagccgg                                                  19
```

```
<210> SEQ ID NO 17
<211> LENGTH: 20
<212> TYPE: DNA
<213> ORGANISM: Mus musculus

<400> SEQUENCE: 17
catcttggcc tcactgtcca                                              20

<210> SEQ ID NO 18
<211> LENGTH: 19
<212> TYPE: DNA
<213> ORGANISM: Mus musculus

<400> SEQUENCE: 18
gggccggact catcgtact                                               19

<210> SEQ ID NO 19
<211> LENGTH: 26
<212> TYPE: DNA
<213> ORGANISM: Mus musculus
<220> FEATURE:
<223> OTHER INFORMATION: Synthetic oligonucleotide primer

<400> SEQUENCE: 19
cttccagcag atgtggatca gcaagc                                       26

<210> SEQ ID NO 20
<211> LENGTH: 23
<212> TYPE: DNA
<213> ORGANISM: Mus musculus

<400> SEQUENCE: 20
agtggcaatg ctatcatcat cgt                                          23

<210> SEQ ID NO 21
<211> LENGTH: 25
<212> TYPE: DNA
<213> ORGANISM: Mus musculus

<400> SEQUENCE: 21
aaggaataag tgggaaccca gatca                                        25

<210> SEQ ID NO 22
<211> LENGTH: 24
<212> TYPE: DNA
<213> ORGANISM: Mus musculus

<400> SEQUENCE: 22
cctggcaaga acgcagtcac cctg                                         24

<210> SEQ ID NO 23
<211> LENGTH: 21
<212> TYPE: DNA
<213> ORGANISM: Mus musculus

<400> SEQUENCE: 23
tctccgagac ctcctccatc t                                            21

<210> SEQ ID NO 24
<211> LENGTH: 18
<212> TYPE: DNA
<213> ORGANISM: Mus musculus

<400> SEQUENCE: 24
```

-continued ttccaggacg ccatccag                                                18

<210> SEQ ID NO 25
<211> LENGTH: 23
<212> TYPE: DNA
<213> ORGANISM: Mus musculus

<400> SEQUENCE: 25
tccctgcctc agaccagtgg cct                                          23

<210> SEQ ID NO 26
<211> LENGTH: 20
<212> TYPE: DNA
<213> ORGANISM: Mus musculus

<400> SEQUENCE: 26
caggagagca gggatttgca                                              20

<210> SEQ ID NO 27
<211> LENGTH: 21
<212> TYPE: DNA
<213> ORGANISM: Mus musculus

<400> SEQUENCE: 27
cctacgctca gccctcttca t                                            21

<210> SEQ ID NO 28
<211> LENGTH: 24
<212> TYPE: DNA
<213> ORGANISM: Mus musculus

<400> SEQUENCE: 28
agagggcctc cctcctacgc ttgg                                         24

<210> SEQ ID NO 29
<211> LENGTH: 488
<212> TYPE: PRT
<213> ORGANISM: Homo sapiens

<400> SEQUENCE: 29

Met Gly Asp Arg Gly Ser Ser Arg Arg Arg Thr Gly Ser Arg Pro
1               5                   10                  15

Ser Ser His Gly Gly Gly Pro Ala Ala Glu Glu Val Arg
                20                  25                  30

Asp Ala Ala Ala Gly Pro Asp Val Gly Ala Ala Gly Asp Ala Pro Ala
            35                  40                  45

Pro Ala Pro Asn Lys Asp Gly Asp Ala Gly Val Gly Ser Gly His Trp
        50                  55                  60

Glu Leu Arg Cys His Arg Leu Gln Asp Ser Leu Phe Ser Ser Asp Ser
65                  70                  75                  80

Gly Phe Ser Asn Tyr Arg Gly Ile Leu Asn Trp Cys Val Val Met Leu
                85                  90                  95

Ile Leu Ser Asn Ala Arg Leu Phe Leu Glu Asn Leu Ile Lys Tyr Gly
                100                 105                 110

Ile Leu Val Asp Pro Ile Gln Val Val Ser Leu Phe Leu Lys Asp Pro
            115                 120                 125

His Ser Trp Pro Ala Pro Cys Leu Val Ile Ala Ala Asn Val Phe Ala
        130                 135                 140

Val Ala Ala Phe Gln Val Glu Lys Arg Leu Ala Val Gly Ala Leu Thr
145                 150                 155                 160

```
Glu Gln Ala Gly Leu Leu His Val Ala Asn Leu Ala Thr Ile Leu
            165                 170                 175

Cys Phe Pro Ala Ala Val Val Leu Val Glu Ser Ile Thr Pro Val
            180                 185                 190

Gly Ser Leu Leu Ala Leu Met Ala His Thr Ile Leu Phe Leu Lys Leu
            195                 200                 205

Phe Ser Tyr Arg Asp Val Asn Ser Trp Cys Arg Ala Arg Ala Lys
            210                 215                 220

Ala Ala Ser Ala Gly Lys Lys Ala Ser Ser Ala Ala Pro His Thr
225                 230                 235                 240

Val Ser Tyr Pro Asp Asn Leu Thr Tyr Arg Asp Leu Tyr Tyr Phe Leu
            245                 250                 255

Phe Ala Pro Thr Leu Cys Tyr Glu Leu Asn Phe Pro Arg Ser Pro Arg
            260                 265                 270

Ile Arg Lys Arg Phe Leu Leu Arg Arg Ile Leu Glu Met Leu Phe Phe
            275                 280                 285

Thr Gln Leu Gln Val Gly Leu Ile Gln Gln Trp Met Val Pro Thr Ile
290                 295                 300

Gln Asn Ser Met Lys Pro Phe Lys Asp Met Asp Tyr Ser Arg Ile Ile
305                 310                 315                 320

Glu Arg Leu Leu Lys Leu Ala Val Pro Asn His Leu Ile Trp Leu Ile
            325                 330                 335

Phe Phe Tyr Trp Leu Phe His Ser Cys Leu Asn Ala Val Ala Glu Leu
            340                 345                 350

Met Gln Phe Gly Asp Arg Glu Phe Tyr Arg Asp Trp Trp Asn Ser Glu
            355                 360                 365

Ser Val Thr Tyr Phe Trp Gln Asn Trp Asn Ile Pro Val His Lys Trp
            370                 375                 380

Cys Ile Arg His Phe Tyr Lys Pro Met Leu Arg Arg Gly Ser Ser Lys
385                 390                 395                 400

Trp Met Ala Arg Thr Gly Val Phe Leu Ala Ser Ala Phe Phe His Glu
            405                 410                 415

Tyr Leu Val Ser Val Pro Leu Arg Met Phe Arg Leu Trp Ala Phe Thr
            420                 425                 430

Gly Met Met Ala Gln Ile Pro Leu Ala Trp Phe Val Gly Arg Phe Phe
            435                 440                 445

Gln Gly Asn Tyr Gly Asn Ala Ala Val Trp Leu Ser Leu Ile Ile Gly
            450                 455                 460

Gln Pro Ile Ala Val Leu Met Tyr Val His Asp Tyr Tyr Val Leu Asn
465                 470                 475                 480

Tyr Glu Ala Pro Ala Ala Glu Ala
            485

<210> SEQ ID NO 30
<211> LENGTH: 29
<212> TYPE: DNA
<213> ORGANISM: Artificial Sequence
<220> FEATURE:
<223> OTHER INFORMATION: synthetic primer

<400> SEQUENCE: 30
gttcatcgat ctttattcct accgggatg                                      29

<210> SEQ ID NO 31
<211> LENGTH: 32
```

```
<212> TYPE: DNA
<213> ORGANISM: Artificial Sequence
<220> FEATURE:
<223> OTHER INFORMATION: synthetic primer

<400> SEQUENCE: 31
agaaggtcga ccacagcatt gagacaggag tg                                32

<210> SEQ ID NO 32
<211> LENGTH: 37
<212> TYPE: DNA
<213> ORGANISM: Artificial Sequence
<220> FEATURE:
<223> OTHER INFORMATION: synthetic primer

<400> SEQUENCE: 32
tgctttaggg cgcgcctgag gtactgccaa aggccag                           37

<210> SEQ ID NO 33
<211> LENGTH: 20
<212> TYPE: DNA
<213> ORGANISM: Artificial Sequence
<220> FEATURE:
<223> OTHER INFORMATION: synthetic primer

<400> SEQUENCE: 33
ctccatgaag cccttcaagg                                              20

<210> SEQ ID NO 34
<211> LENGTH: 20
<212> TYPE: DNA
<213> ORGANISM: Artificial Sequence
<220> FEATURE:
<223> OTHER INFORMATION: synthetic primer

<400> SEQUENCE: 34
tgtgcacggg gatattccag                                              20

<210> SEQ ID NO 35
<211> LENGTH: 25
<212> TYPE: DNA
<213> ORGANISM: Artificial Sequence
<220> FEATURE:
<223> OTHER INFORMATION: synthetic primer

<400> SEQUENCE: 35
taccggtgga tgtggaatgt gtgcg                                        25
```